US011958042B2

(12) United States Patent
Pederson et al.

(10) Patent No.: US 11,958,042 B2
(45) Date of Patent: *Apr. 16, 2024

(54) REACTIONS OF OLEFIN DERIVATIVES IN THE PRESENCE OF METATHESIS CATALYSTS

(71) Applicant: Umicore AG & Co. KG, Hanau-Wolfgang (DE)

(72) Inventors: Richard Pederson, San Gabriel, CA (US); Adam M. Johns, Claremont, CA (US)

(73) Assignee: Umicore AG & Co. KG, Hanau-Wolfgang (DE)

( * ) Notice: Subject to any disclaimer, the term of this patent is extended or adjusted under 35 U.S.C. 154(b) by 158 days.

This patent is subject to a terminal disclaimer.

(21) Appl. No.: 17/515,910

(22) Filed: Nov. 1, 2021

(65) Prior Publication Data

US 2022/0055025 A1 Feb. 24, 2022

Related U.S. Application Data

(63) Continuation of application No. 16/969,379, filed as application No. PCT/EP2019/053336 on Feb. 11, 2019, now Pat. No. 11,161,104.

(60) Provisional application No. 62/629,857, filed on Feb. 13, 2018.

(51) Int. Cl.
*B01J 31/22* (2006.01)
*C07D 313/00* (2006.01)
*C07F 15/00* (2006.01)

(52) U.S. Cl.
CPC ........ *B01J 31/2273* (2013.01); *C07D 313/00* (2013.01); *C07F 15/0046* (2013.01); *B01J 2231/543* (2013.01); *B01J 2531/821* (2013.01)

(58) Field of Classification Search
None
See application file for complete search history.

(56) References Cited

U.S. PATENT DOCUMENTS

| 7,039,565 | B1 | 5/2006 | Jin et al. |
| 11,065,609 | B2 * | 7/2021 | Johns ................... B01J 31/2273 |
| 11,161,104 | B2 * | 11/2021 | Pederson ................ C07C 67/08 |
| 2013/0079575 | A1 | 3/2013 | Schertzer et al. |
| 2013/0171071 | A1 | 7/2013 | Kuehl |
| 2014/0371454 | A1 | 12/2014 | Hoveyda et al. |
| 2016/0368888 | A1 * | 12/2016 | Davey ................... C07D 313/00 |
| 2019/0184385 | A1 * | 6/2019 | Johns ................... B01J 31/1875 |
| 2022/0379292 | A1 * | 12/2022 | Johns ................... C07F 15/0046 |

FOREIGN PATENT DOCUMENTS

| CN | 102123979 A | 7/2011 |
| EP | 3115368 A1 | 1/2017 |
| WO | 2017/100585 A1 | 6/2017 |
| WO | 2018/038928 A1 | 3/2018 |
| WO | 2018/191373 A1 | 10/2018 |
| WO | 2018/208501 A1 | 11/2018 |

OTHER PUBLICATIONS

Skowerski et al. "Tube-In-Tube Reactor as a Useful Tool for Homo- and Heterogeneous Olefin Metathesis under Continuous Flow Mode" ChemSusChem, 2014, vol. 7, No. 2, pp. 536-542.*
Wuts et al., "Greene's Protective Groups in Organic Synthesis," 4th Edition, Apr. 2006, 1264 Pages.
Andre et al., Accessible ring opening metathesis and atom transfer radical polymerization catalysts based on dimethyl sulfoxide ruthenium(II) complexes bearing N-heterocyclic carbene ligands, Mol. Cat., vol. 448, 2018 pp. 135-143.
Calligaris et al., "Structure and bonding in metal sulfoxide complexes", Coordination Chemistry Reviews, vol. 153, 1996, pp. 83-154.
Goldring et al., Synthesis of macrocyclic lactams and lactones via ring-closing olefin metathesis, Tetrahedron Letters, vol. 39, No. 28, 1998 pp. 4955-4958.
International Preliminary Report on Patentability received for PCT Patent Application No. PCT/EP2019/053336, dated Aug. 27, 2020, 10 pages.
International Search Report and Written Opinion received for PCT Patent Application No. PCT/EP2019/053336, dated Apr. 18, 2019, 13 pages.
Skowerski et al. "Tube-In-Tube Reactor as a Useful Tool for Homo- and Heterogeneous Olefin Metathesis under Continuous Flow Mode" ChemSusChem, 2014, vol. 7, No. 2, 2014, pp. 536-542.

* cited by examiner

*Primary Examiner* — Joseph R Kosack
(74) *Attorney, Agent, or Firm* — Faegre Drinker Biddle & Reath LLP

(57) ABSTRACT

The invention provides a method for synthesizing musk macrocycles comprising contacting an easily accessible diene starting materials bearing a Z-olefin moiety and performing a ring closing metathesis reaction in the presence of a Group 8 olefin metathesis catalyst.

7 Claims, No Drawings

REACTIONS OF OLEFIN DERIVATIVES IN THE PRESENCE OF METATHESIS CATALYSTS

CROSS-REFERENCE TO RELATED APPLICATIONS

This application is a continuation of U.S. application Ser. No. 16/969,379, filed Aug. 12, 2020, which is a national stage application (under 35 U.S.C. § 371) of PCT/EP2019/053336, filed Feb. 11, 2019, which claims benefit of U.S. Application No. 62/629,857, filed Feb. 13, 2018, all of which are incorporated herein by reference in their entirety.

BACKGROUND

Since its discovery in the 1950s, olefin metathesis has emerged as a valuable synthetic method for the formation of carbon-carbon double bonds. Recent advances in applications to organic syntheses and polymer syntheses mostly rely on developments of well-defined olefin metathesis catalysts.

The technology of ruthenium metathesis catalysts has enabled the development of several research platforms including: ring opening metathesis polymerization (ROMP), ring opening cross metathesis (ROCM), cross metathesis (CM), ring closing metathesis (RCM).

In another embodiment, the invention provides methods for the synthesis of macrocyclic compounds utilized in the fragrance industry.

The odor of musk is perhaps the most universally appreciated fragrance. The natural macrocyclic musk compounds turned out to be ketones (animal sources) and lactones (plant materials). They are 15- or 17-membered ring systems. The type of odor is influenced by the ring size. Starting from 14 ring atoms, a weak musk scent is perceived. Compounds with 15-16 ring atoms exhibit strong musk odor.

Macrocyclic musk compounds are expected to be of increasing importance in the future, especially because many of them are naturally occurring and even the synthetic representatives closely resemble the natural counterparts. In addition, the progress in synthetic chemistry contributes to declining prices and will stimulate increased use of this type of musk compounds.

Synthetic musk compounds can be divided into three major classes: aromatic nitro musk compounds, polycyclic musk compounds, and macrocyclic musk compounds. As such, macrocyclic musk compounds have increased in importance in recent years.

The synthesis of macrocyclic musk compounds is difficult, and, in many cases, it is a multi-step procedure. Due to the relatively high production costs, their economic importance is still limited. However, there is a constant demand for these musk compounds in bulk in perfumery industry.

There is a need for effective processes for preparing cyclic compounds based on medium and specifically based on large rings which have at least one keto group. Medium rings generally have 8 to 11 carbon atoms, above 12 carbon atoms one talks of large rings, and compounds based on large rings are also referred to as macrocyclic compounds. Macrocyclic ketones, lactones and epoxides as well as further functionalized macrocycles are aroma chemicals valued in the fragrance industry. There is a need to create new synthetic routes into the highly valued and valuable macrocyclic musk compounds.

The present invention addresses the problems of the prior art and provides an efficient and high-yielding synthesis of macrocyclic musk compounds and their open-chain intermediates, utilizing cross metathesis reactions in the presence of Group 8 metal olefin metathesis catalysts.

The stereochemistry of the alkene, E or Z, in these cyclic structures is often crucial to the biological activity of a molecule or its olfactory characteristics, and small amounts of impurity of the other stereoisomer in chemical mixtures can drastically decrease their potency. It is particularly difficult to separate E- and Z-isomers as techniques for their separation are not general. As such, methods for producing stereochemically pure cyclic compounds are of paramount importance.

Controlling olefin stereochemistry in RCM reactions can be difficult. When using common non-selective metathesis catalysts, selectivity is controlled by the thermodynamic stability of the olefin products and can vary depending on ring size and double bond position.

Furthermore, high catalyst loadings are often needed for macrocyclization reactions using RCM. In these instances, removal of residual metals, the presence of which can be undesirable in the end product or could potentially isomerize products, can be difficult. For some applications, this requires further purification with additives or with multiple chromatographic columns followed by treatment with charcoal.

Common macrocyclic musk compounds include ambrettolide (9-ambrettolide and 7-ambrettolide), nirvanolide, habanolide, cosmone, muscenone, velvione, dihydrocivetone, exaltone, civetone and globanone.

The invention provides a method of forming macrocyclic musk compounds comprising the steps of cross metathesizing a first olefin and a second olefin in the presence of at least one Group 8 metal olefin metathesis catalyst, to form a cross-metathesis product and then cyclizing the cross-metathesis product to form the desired macrocyclic musk compounds.

The macrocyclic musk compounds can be formed by ring closing metathesis of a diene, in the presence of at least one Group 8 metal olefin metathesis catalyst. More particularly the invention is concerned with novel methods for obtaining musk macrocycles in the Z configuration, via cross metathesis reactions, in the presence of at least one Group 8 metal Z-stereoretentive olefin metathesis catalyst.

Using easily accessible diene starting materials bearing a Z-olefin moiety, macrocyclization reactions generated products with significantly higher Z-selectivity in appreciably shorter reaction times, in higher yield, and with much lower catalyst loadings than in previously reported systems. Macrocyclic lactones ranging in size from twelve-membered to seventeen-membered rings are synthesized in moderate to high yields (68-79% yield) with excellent Z-selectivity (95%→99% Z).

SUMMARY OF THE INVENTION

Musk Macrocycles

The present invention relates to a process, involving ring closing metathesis in the presence of at least one Group 8 metal olefin metathesis catalyst, for preparing cyclic compounds having at least eight carbon atoms and at least one keto group, used in the fragrance industry.

Ring closing metathesis reactions were achieved, using the catalysts of the invention and it was shown on a variety of substrates. Using a standard catalyst loading of 6 mol % often used in macrocyclization reactions, reactions were completed within 1 h in dichloromethane under static vacuum (30 mTorr) at 40° C. Twelve- to seventeen-membered rings were all synthesized with high Z-selectivity (95-99% Z) in moderate to high yields (68-79% isolated yield). Yuzu lactone, (Z)-Oxacyclotridec-10-en-2-one, for example, is in high demand by the perfume industry and can be synthesized more rapidly and selectively using ruthenium olefin metathesis catalysts than in previous reports. Larger macrocyclic lactones, fifteen-membered to seventeen-membered rings, were synthesized in slightly higher yields than with smaller twelve- to fourteen-membered.

In summary, highly active, ruthenium-based olefin metathesis catalysts were used for generating highly Z-macrocycles (95-99% Z) from easily available diene substrates with a Z-olefin moiety.

In another aspect, the macrocyclic musk compounds can be synthesized via ring closing olefin metathesis reactions of bis-olefins in the presence of at least one Group 8 metal olefin metathesis catalyst.

In another embodiment, the ring-closing metathesis reaction product has a carbon-carbon double bond in a Z-configuration and is represented by the structure of Formula (A):

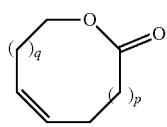

Formula (A)

wherein:
q is 1, 2, 3, or 4; and
p is 4, 5, 6, or 7.

In another embodiment, the ring-closing metathesis reaction product has a carbon-carbon double bond in a Z-configuration and is represented by the structure of Formula (B):

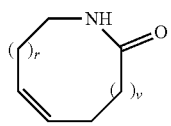

Formula (B)

wherein:
r is 1, 2, 3, or 4; and
v is 4, 5, 6, or 7.

In another embodiment, the ring-closing metathesis reaction product has a carbon-carbon double bond in a Z-configuration and is represented by the structure of Formula (C):

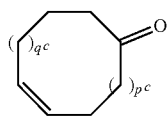

Formula (C)

wherein:
$q^c$ is 1, 2, 3, or 4; and
$p^c$ is 4, 5, 6, or 7.

In another embodiment, the ring-closing metathesis reaction product has a carbon-carbon double bond and is represented by the structure of Formula (K):

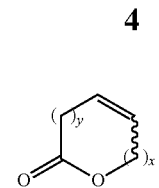

Formula (K)

wherein:
x is 2, 3, 4 or 5;
y is 5, 6, 7, or 8.

In another aspect the invention provides a method of forming a macrocyclic musk compound comprising the steps of cross metathesizing a first olefin and a second olefin in the presence of at least one Group 8 metal olefin metathesis catalyst, to form an intermediate of said first and second olefin and cyclizing the intermediate to form the macrocyclic musk compound.

These and other aspects of the present invention will be apparent to one of skill in the art, in light of the following detailed description and examples. Furthermore, it is to be understood that none of the embodiments or examples of the invention described herein are to be interpreted as being limiting.

DETAILED DESCRIPTION

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an olefin" includes a single olefin as well as a combination or mixture of two or more olefins, reference to "a substituent" encompasses a single substituent as well as two or more substituents, and the like.

As used in the specification and the appended claims, the terms "for example", "for instance", "such as", or "including" are meant to introduce examples that further clarify more general subject matter. Unless otherwise specified, these examples are provided only as an aid for understanding the invention and are not meant to be limiting in any fashion.

In this specification and in the claims, that follow, reference will be made to a number of terms, which shall be defined to have the following meanings:

The term "alkyl" as used herein refers to a linear, branched, or cyclic saturated hydrocarbon group typically although not necessarily containing 1 to 30 carbon atoms, generally containing 1 to 24 carbon atoms, typically 1 to 12 carbon atoms, such as methyl, ethyl, n-propyl, iso-propyl, n-butyl, iso-butyl, t-butyl, octyl, decyl, and the like, as well as cycloalkyl groups such as cyclopentyl, cyclohexyl and the like. The term "lower alkyl" intends an alkyl group of 1 to 6 carbon atoms, and the specific term "cycloalkyl" intends a cyclic alkyl group, typically having 3 to 12, or 4 to 12, or 3 to 10, or 3 to 8, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a divalent linear, branched, or cyclic alkyl group, where "alkyl" is as defined herein.

The term "alkenyl" as used herein refers to a linear, branched, or cyclic hydrocarbon group of 2 to 30 carbon atoms containing at least one double bond, such as ethenyl, n-propenyl, iso-propenyl, n-butenyl, iso-butenyl, octenyl, decenyl, tetradecenyl, hexadecenyl, eicosenyl, tetracosenyl, and the like. Generally, "alkenyl" groups herein contain 2 to 24 carbon atoms, typically "alkenyl" groups herein contain 2 to 12 carbon atoms. The term "lower alkenyl" intends an "alkenyl" group of 2 to 6 carbon atoms, and the specific term "cycloalkenyl" intends a cyclic "alkenyl" group, typically having 5 to 8 carbon atoms. The term "substituted alkenyl" refers to "alkenyl" substituted with one or more substituent groups, and the terms "heteroatom-containing alkenyl" and "heteroalkenyl" refer to "alkenyl" in which at least one carbon atom is replaced with a heteroatom. If not otherwise indicated, the terms "alkenyl" and "lower alkenyl" include linear, branched, cyclic, unsubstituted, substituted, and/or heteroatom-containing "alkenyl" and lower "alkenyl", respectively. The term "alkenyl" is used interchangeably with the term "olefin" herein.

The term "alkenylene" as used herein refers to a divalent linear, branched, or cyclic alkenyl group, where "alkenyl" is as defined herein.

The term "alkynyl" as used herein refers to a linear or branched hydrocarbon group of 2 to 30 carbon atoms containing at least one triple bond, such as ethynyl, n-propynyl, and the like. Generally, "alkynyl" groups herein contain 2 to 24 carbon atoms; typical "alkynyl" groups described herein contain 2 to 12 carbon atoms. The term "lower alkynyl" intends an "alkynyl" group of 2 to 6 carbon atoms. The term "substituted alkynyl" refers to "alkynyl" substituted with one or more substituent groups, and the terms "heteroatom-containing alkynyl" and "heteroalkynyl" refer to "alkynyl" in which at least one carbon atom is replaced with a heteroatom. If not otherwise indicated, the terms "alkynyl" and "lower alkynyl" include linear, branched, unsubstituted, substituted, and/or heteroatom-containing "alkynyl" and lower "alkynyl" respectively.

The term "alkoxy" as used herein intends an alkyl group bound through a single, terminal ether linkage; that is, an "alkoxy" group can be represented as —O-alkyl where alkyl is as defined herein. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). "Aryl" groups contain 5 to 30 carbon atoms, generally "aryl" groups contain 5 to 20 carbon atoms; and typically, "aryl" groups contain 5 to 14 carbon atoms. Exemplary "aryl" groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups; for example, 2,4,6-trimethylphenyl (i.e., mesityl or Mes), 2-methyl-phenyl, 2,6-di-iso-propylphenyl (i.e., DIPP or DiPP), 2-isopropyl-phenyl (i.e., IPP, Ipp or ipp), 2-iso-propyl-6-methylphenyl (i.e., MIPP or Mipp or MiPP). The terms "heteroatom-containing aryl" and "heteroaryl" refer to "aryl" substituents in which at least one carbon atom is replaced with a heteroatom, as will be described in further detail infra.

The term "aryloxy" as used herein refers to an aryl group bound through a single, terminal ether linkage, wherein "aryl" is as defined herein. An "aryloxy" group can be represented as —O-aryl where aryl is as defined herein. Preferred "aryloxy" groups contain 5 to 24 carbon atoms, and particularly preferred "aryloxy" groups contain 5 to 14 carbon atoms. Examples of "aryloxy" groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined herein. "Alkaryl" and "aralkyl" groups contain 6 to 30 carbon atoms; generally, "alkaryl" and "aralkyl" groups contain 6 to 20 carbon atoms; and typically, "alkaryl" and "aralkyl" groups contain 6 to 16 carbon atoms. "Alkaryl" groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of "aralkyl" groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is "alkaryl" or "aralkyl", respectively, as defined herein.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined herein.

The terms "cyclic" and "ring" refer to alicyclic or aromatic groups that may or may not be substituted and/or heteroatom containing, and that can be monocyclic, bicyclic, or polycyclic. The term "alicyclic" is used in the conventional sense to refer to an aliphatic cyclic moiety, as opposed to an aromatic cyclic moiety, and can be monocyclic, bicyclic, or polycyclic.

The terms "halo", "halogen" and "halide" are used in the conventional sense to refer to a chloro, bromo, fluoro, or iodo substituent.

The term "hydrocarbyl" refers to univalent "hydrocarbyl" moieties containing 1 to 30 carbon atoms, typically containing 1 to 24 carbon atoms, specifically containing 1 to 12 carbon atoms, including linear, branched, cyclic, saturated, and unsaturated species, such as alkyl groups, alkenyl groups, aryl groups, and the like. The term "lower hydrocarbyl" intends a "hydrocarbyl" group of 1 to 6 carbon atoms, typically 1 to 4 carbon atoms, and the term "hydrocarbylene" intends a divalent "hydrocarbyl" moiety containing 1 to 30 carbon atoms, typically 1 to 24 carbon atoms, specifically 1 to 12 carbon atoms, including linear, branched, cyclic, saturated and unsaturated species. The term "lower hydrocarbylene" intends a "hydrocarbylene" group of 1 to 6 carbon atoms. "Substituted hydrocarbyl" refers to "hydrocarbyl" substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to "hydrocarbylene" substituted with one or more substituent groups, and the terms "heteroatom-containing hydrocarbylene" and heterohydrocarbylene" refer to "hydrocarbylene" in which at least one carbon atom is replaced with a heteroatom. Unless otherwise indicated, the term "hydrocarbyl" and "hydrocarbylene" are to be interpreted as including substituted and/or heteroatom-containing "hydrocarbyl" and "hydrocarbylene" moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" can be monocyclic, bicyclic, or polycyclic as described herein with respect to the term "aryl." Examples of heteroalkyl groups include alkoxyaryl-, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{24}$ arylcarbonato (—O—(CO)—O-aryl), carboxyl (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, ($C_1$-$C_{24}$ alkyl)($C_5$-$C_{24}$ aryl)-substituted amino, ($C_2$-$C_{24}$ alkyl)-amido (—NH—(CO)-alkyl), ($C_6$-$C_{24}$ aryl)-amido (—NH—(CO)-aryl), imino (—CR=NH where R is hydrogen, $C_1$-$C_{24}$ alkyl, $C_5$-$C_{24}$ aryl, $C_6$-$C_{24}$ alkaryl, $C_6$-$C_{24}$ aralkyl, etc.), ($C_2$-$C_{20}$ alkyl)-imino (—CR=N(alkyl), where R is hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R is hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), ($C_1$-$C_{24}$ alkyl)-sulfanyl (—S-alkyl; also termed "alkylthio"), ($C_5$-$C_{24}$ aryl)-sulfanyl (—S-aryl; also termed "arylthio"), ($C_1$-$C_{24}$ alkyl)-sulfinyl (—(SO)-alkyl), ($C_5$-$C_{24}$ aryl)-sulfinyl (—(SO)-aryl), ($C_1$-$C_{24}$ alkyl)-sulfonyl (—SO$_2$-alkyl), mono-($C_1$-$C_{24}$ alkyl)-aminosulfonyl —SO$_2$—N(H)alkyl), di-($C_1$-$C_{24}$ alkyl)-aminosulfonyl —SO$_2$—N(alkyl)$_2$, ($C_5$-$C_{24}$ aryl)-sulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

The term "NHC" ligand, refers to a N-heterocyclic carbene ligand.

The term "CAAC" ligand, refers to a cyclic alkyl amino carbene ligand also known as "Bertrand-type ligand".

Functional groups, such as ether, ester, hydroxyl, carbonate, may be protected in cases where the functional group interferes with the olefin metathesis catalyst, and any of the protecting groups commonly used in the art may be employed. Acceptable protecting groups may be found, for example, in Greene et al., Protective Groups in Organic Synthesis, 4rd Ed. (Published by John Wiley & Sons, Inc., Hoboken, N.J. 2007).

The geometry of the olefins described in this patent application may be of E-configuration, or of Z-configuration, or of a mixture of E- and Z-configurations. Applicants have represented a mixture of double-bond isomers by using a squiggly bond "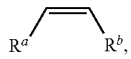". For example, as represented herein, structure

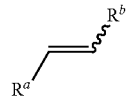

exemplifies either the E-configuration

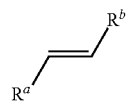

or the Z-configuration

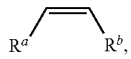

or can represent a mixture of E- and Z-configurations. Suitable ether protecting groups include a branched or non-branched alkyl moiety containing 1 to 5 carbon atoms, for example methyl, ethyl, propyl, i-propyl, t-Bu or t-amyl.

Suitable ester protecting groups include —C(O)R, wherein R=hydrogen, or a branched or non-branched alkyl moiety containing 1 to 7 carbon atoms, for example methyl, ethyl, propyl, i-propyl, t-butyl or t-amyl.

Suitable silyl ether protecting groups include —Si(R)$_3$; wherein R is a branched or unbranched alkyl moiety, which may include methyl, ethyl and propyl and t-butyl.

Suitable carbonate protecting groups include —C(O)OR, wherein R is a branched or non-branched alkyl moiety, for example methyl, ethyl or propyl.

By "sulfoxide group" is meant —[S(O)]—.

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described herein. The term "functional group" is meant to include any functional species that is suitable for the uses described herein. In particular, as used herein, a functional group would necessarily possess the ability to react with or bond to corresponding functional groups on a substrate surface.

In addition, the functional groups may, if a particular group permits, be further substituted with one or more additional functional groups or with one or more hydrocarbyl moieties such as those specifically enumerated herein. Analogously, the herein-mentioned hydrocarbyl moieties can be further substituted with one or more functional groups or additional hydrocarbyl moieties such as those specifically enumerated.

"Optional" or "optionally" means that the subsequently described circumstance can or cannot occur, so that the description includes instances where the circumstance occurs and instances where it does not. For example, the phrase "optionally substituted" means that a non-hydrogen substituent can or cannot be present on a given atom, and, thus, the description includes structures wherein a non-hydrogen substituent is present and structures wherein a non-hydrogen substituent is not present.

Group 8 Metal Olefin Metathesis Catalyst

The Group 8 metal olefin metathesis catalysts of the invention are represented by the general structure of Formula (1)

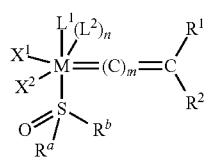

Formula (1)

wherein:

M is a Group 8 transition metal; generally, M is ruthenium or osmium; typically, M is ruthenium;

$L^1$ and $L^2$ are independently neutral electron donor ligands;

n is 0 or 1; typically, n is 0;

m is 0, 1 or 2; typically, m is 0;

$R^a$ is hydrogen, unsubstituted hydrocarbyl, substituted hydrocarbyl, unsubstituted heteroatom-containing hydrocarbyl, or substituted heteroatom-containing hydrocarbyl; generally, $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;

$R^b$ is hydrogen, unsubstituted hydrocarbyl, substituted hydrocarbyl, unsubstituted heteroatom-containing hydrocarbyl, or substituted heteroatom-containing hydrocarbyl; generally $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^b$ is methyl, ethyl, n-propyl, iso-propyl, n-butyl, tert-butyl, cyclohexyl or phenyl; or $R^a$ and $R^b$ are linked together to form a five or a six heterocyclic membered ring with the sulfoxide group [—S(O)—];

$X^1$ and $X^2$ are independently anionic ligands; generally, $X^1$ and $X^2$ are independently halogen, trifluoroacetate, per-fluorophenols or nitrate; typically, $X^1$ and $X^2$ are independently Cl, Br, I or F; and $R^1$ and $R^2$ are independently hydrogen, unsubstituted hydrocarbyl, substituted hydrocarbyl, unsubstituted heteroatom-containing hydrocarbyl, or substituted heteroatom-containing hydrocarbyl; typically, $R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene.

In some embodiments of Formula (1),

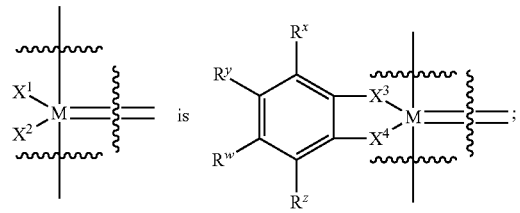

wherein:

M, $X^1$ and $X^2$ are as defined herein;

$X^3$ and $X^4$ are independently O or S; and $R^x$, $R^y$, $R^w$ and $R^z$ are independently hydrogen, halogen, unsubstituted hydrocarbyl, substituted hydrocarbyl, unsubstituted heteroatom-containing hydrocarbyl, or substituted heteroatom-containing hydrocarbyl; or $R^x$ and $R^y$ are linked together to form an unsubstituted bicyclic or polycyclic aryl or a substituted bicyclic or polycyclic aryl; or $R^w$ and $R^z$ are linked together to form an unsubstituted bicyclic or polycyclic aryl or a substituted bicyclic or polycyclic aryl; or $R^y$ and $R^w$ are linked together to form an unsubstituted bicyclic or polycyclic aryl or a substituted bicyclic or polycyclic aryl.

The Group 8 metal olefin metathesis catalysts used in the invention can be represented by the structure of Formula (2):

Formula (2)

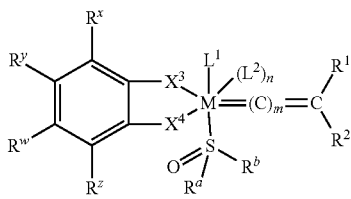

wherein:
M is a Group 8 transition metal; generally, M is ruthenium or osmium; typically, M is ruthenium;
$L^1$ and $L^2$ are independently a neutral electron donor ligand;
n is 0 or 1; typically, n is 0;
m is 0, 1 or 2; typically, m is 0;
$R^a$ is hydrogen, unsubstituted hydrocarbyl, substituted hydrocarbyl, unsubstituted heteroatom-containing hydrocarbyl, or substituted heteroatom-containing hydrocarbyl; generally, $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;
$R^b$ is hydrogen, unsubstituted hydrocarbyl, substituted hydrocarbyl, unsubstituted heteroatom-containing hydrocarbyl, or substituted heteroatom-containing hydrocarbyl; generally $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^b$ is methyl, ethyl, n-propyl, iso-propyl, n-butyl, tert-butyl, cyclohexyl or phenyl; or $R^a$ and $R^b$ are linked together to form a five or a six heterocyclic membered ring with the sulfoxide group;
$R^1$ and $R^2$ are independently hydrogen, unsubstituted hydrocarbyl, substituted hydrocarbyl, unsubstituted heteroatom-containing hydrocarbyl, or substituted heteroatom-containing hydrocarbyl; typically, $R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene;
$X^3$ and $X^4$ are independently O or S; typically, $X^3$ and $X^4$ are independently S; and
$R^x$, $R^y$, $R^w$ and $R^z$ are independently hydrogen, halogen, unsubstituted hydrocarbyl, substituted hydrocarbyl, unsubstituted heteroatom-containing hydrocarbyl, or substituted heteroatom-containing hydrocarbyl; generally $R^x$, $R^y$, $R^w$ and $R^z$ are independently hydrogen, halogen, unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^x$, $R^y$, $R^w$ and $R^z$ are independently $C_1$-$C_6$ alkyl, hydrogen, unsubstituted phenyl, substituted phenyl or halogen; or $R^x$ and $R^y$ are linked together to form an unsubstituted bicyclic or polycyclic aryl or a substituted bicyclic or polycyclic aryl; or $R^w$ and $R^z$ are linked together to form an unsubstituted bicyclic or polycyclic aryl or a substituted bicyclic or polycyclic aryl; or $R^y$ and $R^w$ are linked together to form an unsubstituted bicyclic or polycyclic aryl or a substituted bicyclic or polycyclic aryl.

The Group 8 metal olefin metathesis catalysts used in the invention are represented by the structure of Formula (3), Formula (3)

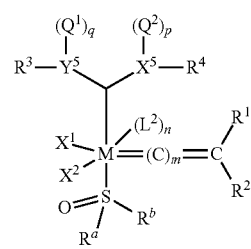

wherein:
M is a Group 8 transition metal; generally, M is ruthenium or osmium; typically, M is ruthenium;
$L^2$ is a neutral electron donor ligand;
n is 0 or 1; typically, n is 0;
m is 0, 1 or 2; typically, m is 0;
$R^a$ is hydrogen, unsubstituted hydrocarbyl, substituted hydrocarbyl, unsubstituted heteroatom-containing hydrocarbyl, or substituted heteroatom-containing hydrocarbyl; generally, $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;
$R^b$ is hydrogen, unsubstituted hydrocarbyl, substituted hydrocarbyl, unsubstituted heteroatom-containing hydrocarbyl, or substituted heteroatom-containing hydrocarbyl; generally $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^b$ is methyl, ethyl, n-propyl, iso-propyl, n-butyl, tert-butyl, cyclohexyl or phenyl; or $R^a$ and $R^b$ are linked together to form a five or a six heterocyclic membered ring with the sulfoxide group;
$X^1$ and $X^2$ are independently anionic ligands; generally, $X^1$ and $X^2$ are independently halogen, trifluoroacetate, per-fluorophenols or nitrate; typically, $X^1$ and $X^2$ are independently Cl, Br, I or F;
$R^1$ and $R^2$ are independently hydrogen, unsubstituted hydrocarbyl, substituted hydrocarbyl, unsubstituted heteroatom-containing hydrocarbyl, or substituted heteroatom-containing hydrocarbyl; typically, $R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene;
$X^5$ and $Y^5$ are independently C, $CR^{3A}$, N, O, S, or P; only one of $X^5$ or $Y^5$ can be C or $CR^{3A}$; typically, $X^5$ and $Y^5$ are independently N;
$Q^1$, $Q^2$, $R^3$, $R^{3A}$ and $R^4$ are independently hydrogen, unsubstituted hydrocarbyl, substituted hydrocarbyl, unsubstituted heteroatom-containing hydrocarbyl, or substituted heteroatom-containing hydrocarbyl; generally, $Q^1$, $Q^2$, $R^3$, $R^{3A}$ and $R^4$ are optionally linked to $X^5$ or $Y^5$ via a linker such as unsubstituted hydrocarbylene, substituted hydrocarbylene, unsubstituted heteroatom-containing hydrocarbylene, substituted heteroatom-containing hydrocarbylene, or —(CO)—; typically $Q^1$, $Q^2$, $R^3$, $R^{3A}$ and $R^4$ are directly linked to $X^5$ or $Y^5$; and p is 0 when $X^5$ is O or S, p is 1 when $X^5$ is N, P or $CR^{3A}$, and p is 2 when $X^5$ is C; q is 0 when $Y^5$ is O or S, q is 1 when $Y^5$ is N, P or $CR^{3A}$, and q is 2 when $X^5$ is C.

The Group 8 metal olefin metathesis catalysts used in the invention are represented by the structure of Formula (4):

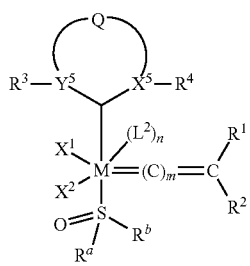

Formula (4)

wherein:
M is a Group 8 transition metal; generally, M is ruthenium or osmium; typically, M is ruthenium;
n is 0 or 1; typically, n is 0;
m is 0, 1 or 2; typically, m is 0;
$R^a$ is hydrogen, unsubstituted hydrocarbyl, substituted hydrocarbyl, unsubstituted heteroatom-containing hydrocarbyl, or substituted heteroatom-containing hydrocarbyl; generally, $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;
$R^b$ is hydrogen, unsubstituted hydrocarbyl, substituted hydrocarbyl, unsubstituted heteroatom-containing hydrocarbyl, or substituted heteroatom-containing hydrocarbyl; generally, $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^b$ is methyl, ethyl, n-propyl, iso-propyl, n-butyl, tert-butyl, cyclohexyl or phenyl; or $R^a$ and $R^b$ are linked together to form a five or a six-heterocyclic membered ring with the sulfoxide group;
$X^1$ and $X^2$ are independently anionic ligands; generally, $X^1$ and $X^2$ are independently halogen, trifluoroacetate, per-fluorophenols or nitrate; typically, $X^1$ and $X^2$ are independently Cl, Br, I or F;
$R^1$ and $R^2$ are independently hydrogen, unsubstituted hydrocarbyl, substituted hydrocarbyl, unsubstituted heteroatom-containing hydrocarbyl, or substituted heteroatom-containing hydrocarbyl; typically, $R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene;
$X^5$ and $Y^5$ are independently C, $CR^{3A}$, or N; only one of $X^5$ or $Y^5$ can be C or $CR^{3A}$; typically, $X^5$ and $Y^5$ are independently N;
$R^{3A}$ is hydrogen, unsubstituted hydrocarbyl, substituted hydrocarbyl, unsubstituted heteroatom-containing hydrocarbyl, or substituted heteroatom-containing hydrocarbyl; Q is a linker, typically unsubstituted hydrocarbylene, substituted hydrocarbylene, unsubstituted heteroatom-containing hydrocarbylene, or substituted heteroatom-containing hydrocarbylene; generally Q is a two-atom linkage having the structure —[$CR^{11}R^{12}$]$_s$—[$CR^{13}R^{14}$]$_t$— or —[$CR^{11}$=$CR^3$]—; typically Q is —[$CR^{11}R^{12}$]$_s$—[$CR^{13}R^{14}$]$_t$—, wherein $R^{11}$, $R^{12}$, $R^{13}$, and $R^{14}$ are independently hydrogen, unsubstituted hydrocarbyl, substituted hydrocarbyl, unsubstituted heteroatom-containing hydrocarbyl, or substituted heteroatom-containing hydrocarbyl; typically $R^{11}$, $R^{12}$, $R^{13}$ and $R^{14}$ are independently hydrogen, unsubstituted $C_1$-$C_{12}$ alkyl, substituted $C_1$-$C_{12}$ alkyl, unsubstituted $C_1$-$C_{12}$ heteroalkyl, substituted $C_1$-$C_{12}$ heteroalkyl, unsubstituted $C_5$-$C_{14}$ aryl, or substituted $C_5$-$C_{14}$ aryl;

"s" and "t" are independently 1 or 2; typically, "s" and "t" are independently 1; or any two of $R^{11}$, $R^{12}$, $R^{13}$, and $R^{14}$ are optionally linked together to form a substituted or unsubstituted, saturated or unsaturated ring structure;

$R^3$ is unsubstituted hydrocarbyl, substituted hydrocarbyl, unsubstituted heteroatom-containing hydrocarbyl, or substituted heteroatom-containing hydrocarbyl; generally, $R^3$ is unsubstituted $C_3$-$C_{10}$ cycloalkyl, substituted $C_3$-$C_{10}$ cycloalkyl, unsubstituted ($C_5$-$C_{24}$ aryl), ($C_5$-$C_{24}$ aryl) substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^3$ is adamantyl, 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 3,5-di-tert-butylphenyl, 2,4-dimethylphenyl, 2,6-difluorophenyl, 2-fluoro-6-methylphenyl or 2-methylphenyl; and $R^4$ is unsubstituted hydrocarbyl, substituted hydrocarbyl, unsubstituted heteroatom-containing hydrocarbyl, or substituted heteroatom-containing hydrocarbyl; generally, $R^4$ is unsubstituted $C_3$-$C_{10}$ cycloalkyl, substituted $C_3$-$C_{10}$ cycloalkyl, unsubstituted ($C_5$-$C_{24}$ aryl), or ($C_5$-$C_{24}$ aryl) substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^4$ is, 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 3,5-di-tert-butylphenyl, 2,4-dimethylphenyl, 2,6-difluorophenyl, 2-fluoro-6-methylphenyl or 2-methyl-phenyl; or when $X^5$ is $CR^{3A}$, then $R^{3A}$ and $R^4$ can from together a five to ten membered cycloalkyl or heterocyclic ring, with the carbon atom to which they are attached.

In some embodiments of Formula (4),

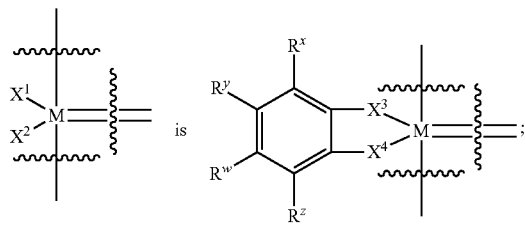

wherein: $X^1, X^2, X^3, X^4, M, R^x, R^y, R^w$ and $R^z$ are as defined herein.

When Q is $-[CR^{11}R^{12}]_s-[CR^{13}R^{14}]_t-$, s is 1, t is 1 and $R^{11}, R^{12}, R^{13}$, and $R^{14}$ are independently hydrogen, and M is ruthenium, then olefin metathesis catalyst of Formula (4), is represented by the structure of Formula (5)

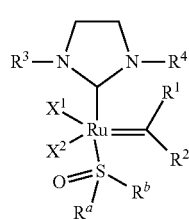

Formula (5)

wherein:
- $R^1$ is hydrogen;
- $R^2$ is unsubstituted hydrocarbyl, substituted hydrocarbyl, unsubstituted heteroatom-containing hydrocarbyl, or substituted heteroatom-containing hydrocarbyl; typically, $R^2$ is unsubstituted phenyl, substituted phenyl, $C_1$-$C_6$ alkyl or substituted 1-propenyl; or $R^1$ and $R^2$ are linked together to form an optionally substituted indenylidene;
- $R^a$ is hydrogen, unsubstituted hydrocarbyl, substituted hydrocarbyl, unsubstituted heteroatom-containing hydrocarbyl, or substituted heteroatom-containing hydrocarbyl; generally, $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;
- $R^b$ is hydrogen, unsubstituted hydrocarbyl, substituted hydrocarbyl, unsubstituted heteroatom-containing hydrocarbyl, or substituted heteroatom-containing hydrocarbyl; generally $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^b$ is methyl, ethyl, n-propyl, iso-propyl, n-butyl, tert-butyl, cyclohexyl or phenyl; or $R^a$ and $R^b$ are linked together to form a five or a six heterocyclic membered ring with the sulfoxide group; typically, $R^a$ and $R^b$ are linked together to form a tetrahydrothiophene oxide;
- $X^1$ and $X^2$ are independently halogen, trifluoroacetate, per-fluorophenols or nitrate; generally, $X^1$ and $X^2$ are independently Cl, Br, I or F; typically, $X^1$ and $X^2$ are independently Cl;
- $R^3$ is unsubstituted hydrocarbyl, substituted hydrocarbyl, unsubstituted heteroatom-containing hydrocarbyl, or substituted heteroatom-containing hydrocarbyl; generally, $R^3$ is unsubstituted $C_3$-$C_{10}$ cycloalkyl, substituted $C_3$-$C_{10}$ cycloalkyl, unsubstituted $C_5$-$C_{24}$ aryl, $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^3$ is adamantyl, 2,4,6-trimethylphenyl, 2,6-di-iso-propylphenyl, 2-iso-propyl-6-methylphenyl, 2-iso-propylphenyl or 2-methyl-phenyl; and
- $R^4$ is unsubstituted hydrocarbyl, substituted hydrocarbyl, unsubstituted heteroatom-containing hydrocarbyl, or substituted heteroatom-containing hydrocarbyl; generally, $R^4$ is unsubstituted $C_3$-$C_{10}$ cycloalkyl, substituted $C_3$-$C_{10}$ cycloalkyl, unsubstituted $C_5$-$C_{24}$ aryl, or $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^4$ is 2,4,6-trimethylphenyl, 2-iso-propyl-phenyl, 2,6-di-iso-propylphenyl, 2-iso-propyl-6-methylphenyl or 2-methyl-phenyl.

Non-limiting examples of olefin metathesis catalysts represented by the structure of Formula (5) are described in Table (1), wherein $X^1$ is Cl and $X^2$ is Cl.

TABLE 1

Olefin Metathesis Catalysts of Formula (5)

| Catalyst | $R^1$ | $R^2$ | $R^3$ | $R^4$ | $R^a$ | $R^b$ |
|---|---|---|---|---|---|---|
| 1 | H | Ph | 2-Me-$C_6H_5$ | 2-Me-$C_6H_5$ | Me | Me |
| 2 | H | Ph | Mes | Mes | Me | Me |
| 3 | H | Ph | Mipp | Mipp | Me | Me |
| 4 | H | Ph | adamantyl | Mes | Me | Me |
| 5 | H | Ph | DIPP | DIPP | Me | Me |
| 6 | H | Ph | IPP | IPP | Me | Me |
| 7 | H | (1-methylpropenyl) | 2-Me-$C_6H_5$ | 2-Me-$C_6H_5$ | Me | Me |

TABLE 1-continued

Olefin Metathesis Catalysts of Formula (5)

| Catalyst | R¹ | R² | R³ | R⁴ | Rᵃ | Rᵇ |
|---|---|---|---|---|---|---|
| 8 | H | 2-methyl-2-butenyl | Mes | Mes | Me | Me |
| 9 | H | 2-methyl-2-butenyl | Mipp | Mipp | Me | Me |
| 10 | H | 2-methyl-2-butenyl | adamantyl | Mes | Me | Me |
| 11 | H | 2-methyl-2-butenyl | DIPP | DIPP | Me | Me |
| 12 | H | 2-methyl-2-butenyl | IPP | IPP | Me | Me |
| 13 | H | 2-isopropoxyphenyl | 2-Me-C₆H₅ | 2-Me-C₆H₅ | Me | Me |
| 14 | H | 2-isopropoxyphenyl | Mes | Mes | Me | Me |
| 15 | H | 2-isopropoxyphenyl | Mipp | Mipp | Me | Me |
| 16 | H | 2-isopropoxyphenyl | adamantyl | Mes | Me | Me |
| 17 | H | 2-isopropoxyphenyl | DIPP | DIPP | Me | Me |

TABLE 1-continued

Olefin Metathesis Catalysts of Formula (5)

| Catalyst | R¹ | R² | R³ | R⁴ | Rᵃ | Rᵇ |
|---|---|---|---|---|---|---|
| 18 | H | 2-isopropoxyphenyl (with gem-dimethyl) | IPP | IPP | Me | Me |
| 19 | | 3-Ph-indenylidene | 2-Me-C₆H₅ | 2-Me-C₆H₅ | Me | Me |
| 20 | | 3-Ph-indenylidene | Mes | Mes | Me | Me |
| 21 | | 3-Ph-indenylidene | Mipp | Mipp | Me | Me |
| 22 | | 3-Ph-indenylidene | adamantyl | Mes | Me | Me |
| 23 | | 3-Ph-indenylidene | DIPP | DIPP | Me | Me |
| 24 | | 3-Ph-indenylidene | IPP | IPP | Me | Me |
| 25 | H | Ph | 2-Me-C₆H₅ | 2-Me-C₆H₅ | cyclopentyl | |
| 26 | H | Ph | Mes | Mes | cyclopentyl | |

TABLE 1-continued
Olefin Metathesis Catalysts of Formula (5)
| Catalyst | R¹ | R² | R³ | R⁴ | Rᵃ | Rᵇ |
|---|---|---|---|---|---|---|
| 27 | H | Ph | Mipp | Mipp | 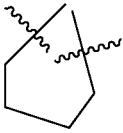 [SMILES: *CCCC*] | |
| 28 | H | Ph | adamantyl | Mes | 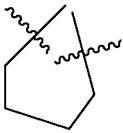 [SMILES: *CCCC*] | |
| 29 | H | Ph | DIPP | DIPP | 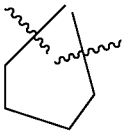 [SMILES: *CCCC*] | |
| 30 | H | Ph | IPP | IPP |  | |
| 31 | H | 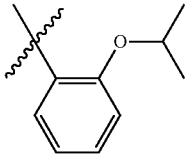 [SMILES: *c1ccccc1OC(C)C] | 2-Me-C₆H₅ | 2-Me-C₆H₅ | 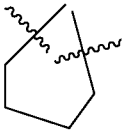 [SMILES: *CCCC*] | |
| 32 | H | 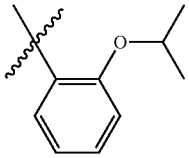 [SMILES: *c1ccccc1OC(C)C] | Mes | Mes | 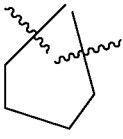 [SMILES: *CCCC*] | |
| 33 | H | 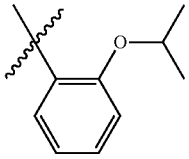 [SMILES: *c1ccccc1OC(C)C] | Mipp | Mipp | 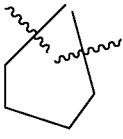 [SMILES: *CCCC*] | |
| 34 | H | 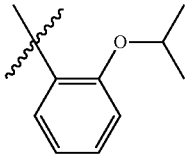 [SMILES: *c1ccccc1OC(C)C] | adamantyl | Mes | 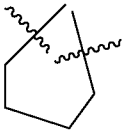 [SMILES: *CCCC*] | |
| 35 | H | 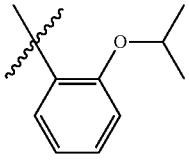 [SMILES: *c1ccccc1OC(C)C] | DIPP | DIPP | 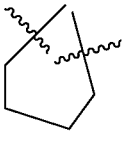 [SMILES: *CCCC*] | |

TABLE 1-continued

Olefin Metathesis Catalysts of Formula (5)

| Catalyst | R¹ | R² | R³ | R⁴ | Rᵃ | Rᵇ |
|---|---|---|---|---|---|---|
| 36 | H | 2-isopropoxyphenyl | IPP | IPP | cyclopentyl | |
| 37 | H | 2-methylpropenyl | 2-Me-C₆H₅ | 2-Me-C₆H₅ | cyclopentyl | |
| 38 | H | 2-methylpropenyl | Mes | Mes | cyclopentyl | |
| 39 | H | 2-methylpropenyl | Mipp | Mipp | cyclopentyl | |
| 40 | H | 2-methylpropenyl | adamantyl | Mes | cyclopentyl | |
| 41 | H | 2-methylpropenyl | DIPP | DIPP | cyclopentyl | |
| 42 | H | 2-methylpropenyl | IPP | IPP | cyclopentyl | |
| 43 | 3-Ph-indenylidene | | 2-Me-C₆H₅ | 2-Me-C₆H₅ | cyclopentyl | |
| 44 | 3-Ph-indenylidene | | Mes | Mes | cyclopentyl | |

TABLE 1-continued

Olefin Metathesis Catalysts of Formula (5)

| Catalyst | R¹ | R² | R³ | R⁴ | Rᵃ | Rᵇ |
|---|---|---|---|---|---|---|
| 45 | | 3-Ph-indenylidene | Mipp | Mipp | cyclopentyl ring | |
| 46 | | 3-Ph-indenylidene | adamantyl | Mes | cyclopentyl ring | |
| 47 | | 3-Ph-indenylidene | DIPP | DIPP | cyclopentyl ring | |
| 48 | | 3-Ph-indenylidene | IPP | IPP | cyclopentyl ring | |
| 49 | H | Ph | 2-Me-C₆H₅ | 2-Me-C₆H₅ | n-Bu | n-Bu |
| 50 | H | Ph | Mes | Mes | n-Bu | n-Bu |
| 51 | H | Ph | Mipp | Mipp | n-Bu | n-Bu |
| 52 | H | Ph | adamantyl | Mes | n-Bu | n-Bu |
| 53 | H | Ph | DIPP | DIPP | n-Bu | n-Bu |
| 54 | H | Ph | IPP | IPP | n-Bu | n-Bu |
| 55 | H | 2-methylpropenyl | 2-Me-C₆H₅ | 2-Me-C₆H₅ | n-Bu | n-Bu |
| 56 | H | 2-methylpropenyl | Mes | Mes | n-Bu | n-Bu |
| 57 | H | 2-methylpropenyl | Mipp | Mipp | n-Bu | n-Bu |
| 58 | H | 2-methylpropenyl | adamantyl | Mes | n-Bu | n-Bu |
| 59 | H | 2-methylpropenyl | DIPP | DIPP | n-Bu | n-Bu |
| 60 | H | 2-methylpropenyl | IPP | IPP | n-Bu | n-Bu |

TABLE 1-continued

Olefin Metathesis Catalysts of Formula (5)

| Catalyst | R¹ | R² | R³ | R⁴ | Rᵃ | Rᵇ |
|---|---|---|---|---|---|---|
| 61 | H | 2-isopropoxyphenyl | 2-Me-C₆H₅ | 2-Me-C₆H₅ | n-Bu | n-Bu |
| 62 | H | 2-isopropoxyphenyl | Mes | Mes | n-Bu | n-Bu |
| 63 | H | 2-isopropoxyphenyl | Mipp | Mipp | n-Bu | n-Bu |
| 64 | H | 2-isopropoxyphenyl | adamantyl | Mes | n-Bu | n-Bu |
| 65 | H | 2-isopropoxyphenyl | DIPP | DIPP | n-Bu | n-Bu |
| 66 | H | 2-isopropoxyphenyl | IPP | IPP | n-Bu | n-Bu |
| 67 | | 3-phenyl-1-indenylidene | 2-Me-C₆H₅ | 2-Me-C₆H₅ | n-Bu | n-Bu |
| 68 | | 3-phenyl-1-indenylidene | Mes | Mes | n-Bu | n-Bu |
| 69 | | 3-phenyl-1-indenylidene | Mipp | Mipp | n-Bu | n-Bu |

TABLE 1-continued

Olefin Metathesis Catalysts of Formula (5)

| Catalyst | R¹ | R² | R³ | R⁴ | Rᵃ | Rᵇ |
|---|---|---|---|---|---|---|
| 70 | | 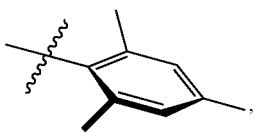 Ph | adamantyl | Mes | n-Bu | n-Bu |
| 71 | | 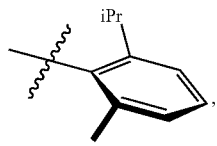 Ph | DIPP | n-Bu | | n-Bu |
| 72 | | 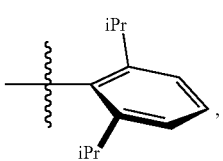 Ph | IPP | n-Bu | | n-Bu | wherein: Mes is

[structure of mesityl group]

Mipp is

[structure of Mipp group]

DIPP is

[structure of DIPP group]

adamantyl is

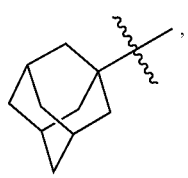 [SMILES: *C12CC3CC(CC(C3)C1)C2]

IPP is

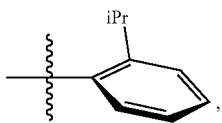

2-Me-C₆H₅ is

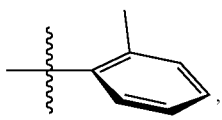

Me is $CH_3-$, n-Bu is $[CH_3-(CH_2)_3-]$, Ph is

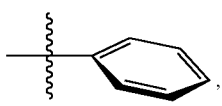

is $[-(CH_2)_4-]$.

When Q is a two-atom linkage having the structure $-[CR^{11}=CR^{13}]-$ and $R^{11}$ and $R^3$ are hydrogen, and M is ruthenium, then the olefin metathesis catalyst of Formula (4), is represented by the structure of Formula (6)

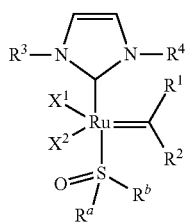

Formula (6)

wherein:
R¹ is hydrogen;
R² is unsubstituted phenyl, substituted phenyl, $C_1$-$C_6$ alkyl or substituted 1-propenyl; or R¹ and R² are linked together to form an optionally substituted indenylidene;
$R^a$ is hydrogen, unsubstituted hydrocarbyl, substituted hydrocarbyl, unsubstituted heteroatom-containing hydrocarbyl, or substituted heteroatom-containing hydrocarbyl; $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl;
$R^b$ is hydrogen, unsubstituted hydrocarbyl, substituted hydrocarbyl, unsubstituted heteroatom-containing hydrocarbyl, or substituted heteroatom-containing hydrocarbyl; $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; or $R^a$ and $R^b$ are linked together to form a five or a six-heterocyclic membered ring with the sulfoxide group;
X¹ and X² are independently halogen, trifluoroacetate, per-fluorophenols or nitrate; X¹ and X² are independently Cl, Br, I or F; typically, X¹ and X² are independently Cl;
R³ is unsubstituted hydrocarbyl, substituted hydrocarbyl, unsubstituted heteroatom-containing hydrocarbyl, or substituted heteroatom-containing hydrocarbyl; generally, R³ is unsubstituted $C_3$-$C_{10}$ cycloalkyl, substituted $C_3$-$C_{10}$ cycloalkyl, unsubstituted $C_5$-$C_{24}$ aryl, $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, R³ is adamantyl, 2,4,6-trimethylphenyl, 2,6-di-iso-propylphenyl, 2-iso-propyl-6-methylphenyl, 2-iso-propyl-phenyl or 2-methyl-phenyl; and
R⁴ is unsubstituted hydrocarbyl, substituted hydrocarbyl, unsubstituted heteroatom-containing hydrocarbyl, or substituted heteroatom-containing hydrocarbyl; generally, R⁴ is unsubstituted $C_3$-$C_{10}$ cycloalkyl, substituted $C_3$-$C_{10}$ cycloalkyl, unsubstituted $C_5$-$C_{24}$ aryl, or $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, R⁴ is 2,4,6-trimethylphenyl, 2-iso-propyl-phenyl, 2,6-di-iso-propylphenyl, 2-iso-propyl-6-methylphenyl or 2-methyl-phenyl.

Non-limiting examples of olefin metathesis catalysts represented by the structure of Formula (6) are described in Table (2), wherein X¹ is Cl and X² is Cl.

TABLE 2

| Olefin Metathesis Catalysts of Formula (6) | | | | | | |
|---|---|---|---|---|---|---|
| Catalyst | R¹ | R² | R³ | R⁴ | $R^a$ | $R^b$ |
| 73 | H | Ph | 2-Me-$C_6H_5$ | 2-Me-$C_6H_5$ | Me | Me |
| 74 | H | Ph | Mes | Mes | Me | Me |
| 75 | H | Ph | Mipp | Mipp | Me | Me |
| 76 | H | Ph | adamantyl | Mes | Me | Me |
| 77 | H | Ph | DIPP | DIPP | Me | Me |
| 78 | H | Ph | IPP | IPP | Me | Me |
| 79 | H | (isobutenyl) | 2-Me-$C_6H_5$ | 2-Me-$C_6H_5$ | Me | Me |
| 80 | H | (isobutenyl) | Mes | Mes | Me | Me |
| 81 | H | (isobutenyl) | Mipp | Mipp | Me | Me |
| 82 | H | (isobutenyl) | adamantyl | Mes | Me | Me |

TABLE 2-continued
Olefin Metathesis Catalysts of Formula (6)
| Catalyst | R¹ | R² | R³ | R⁴ | Rᵃ | Rᵇ |
|---|---|---|---|---|---|---|
| 83 | H | 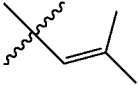 [SMILES: *C=C(C)C] | DIPP | DIPP | Me | Me |
| 84 | H | 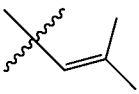 [SMILES: *C=C(C)C] | IPP | IPP | Me | Me |
| 85 | H | 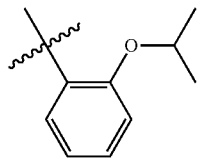 [SMILES: *c1ccccc1OC(C)C] | 2-Me-$C_6H_5$ | 2-Me-$C_6H_5$ | Me | Me |
| 86 | H | 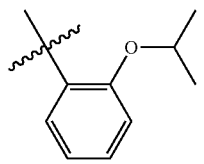 [SMILES: *c1ccccc1OC(C)C] | Mes | Mes | Me | Me |
| 87 | H | 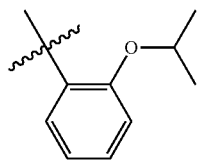 [SMILES: *c1ccccc1OC(C)C] | Mipp | Mipp | Me | Me |
| 88 | H | 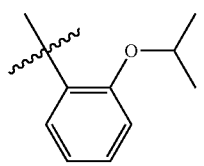 [SMILES: *c1ccccc1OC(C)C] | adamantyl | Mes | Me | Me |
| 89 | H | 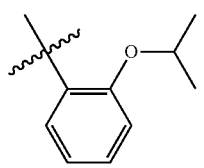 [SMILES: *c1ccccc1OC(C)C] | DIPP | DIPP | Me | Me |
| 90 | H | 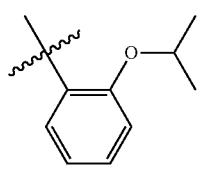 [SMILES: *c1ccccc1OC(C)C] | IPP | IPP | Me | Me |
| 91 | | 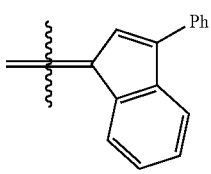 [SMILES: *=C1C=C(c2ccccc2)c2ccccc21] | 2-Me-$C_6H_5$ | 2-Me-$C_6H_5$ | Me | Me |

TABLE 2-continued

Olefin Metathesis Catalysts of Formula (6)

| Catalyst | R¹ | R² | R³ | R⁴ | Rᵃ | Rᵇ |
|---|---|---|---|---|---|---|
| 92 | | Ph-indenyl | Mes | Mes | Me | Me |
| 93 | | Ph-indenyl | Mipp | Mipp | Me | Me |
| 94 | | Ph-indenyl | adamantyl | Mes | Me | Me |
| 95 | | Ph-indenyl | DIPP | DIPP | Me | Me |
| 96 | | Ph-indenyl | IPP | IPP | Me | Me |
| 97 | H | Ph | 2-Me-C₆H₅ | 2-Me-C₆H₅ | cyclopentyl | |
| 98 | H | Ph | Mes | Mes | cyclopentyl | |
| 99 | H | Ph | Mipp | Mipp | cyclopentyl | |
| 100 | H | Ph | adamantyl | Mes | cyclopentyl | |

TABLE 2-continued

Olefin Metathesis Catalysts of Formula (6)

| Catalyst | R¹ | R² | R³ | R⁴ | Rᵃ, Rᵇ |
|---|---|---|---|---|---|
| 101 | H | Ph | DIPP | DIPP | (cyclopentane ring) |
| 102 | H | Ph | IPP | IPP | (cyclopentane ring) |
| 103 | H | 2-isopropoxyphenyl | 2-Me-C₆H₅ | 2-Me-C₆H₅ | (cyclopentane ring) |
| 104 | H | 2-isopropoxyphenyl | Mes | Mes | (cyclopentane ring) |
| 105 | H | 2-isopropoxyphenyl | Mipp | Mipp | (cyclopentane ring) |
| 106 | H | 2-isopropoxyphenyl | adamantyl | Mes | (cyclopentane ring) |
| 107 | H | 2-isopropoxyphenyl | DIPP | DIPP | (cyclopentane ring) |
| 108 | H | 2-isopropoxyphenyl | IPP | IPP | (cyclopentane ring) |
| 109 | H | 2-methylprop-1-enyl | 2-Me-C₆H₅ | 2-Me-C₆H₅ | (cyclopentane ring) |

TABLE 2-continued

Olefin Metathesis Catalysts of Formula (6)

| Catalyst | R¹ | R² | R³ | R⁴ | Rᵃ | Rᵇ |
|---|---|---|---|---|---|---|
| 110 | H | (prenyl) | Mes | Mes | (cyclopentyl) | |
| 111 | H | (prenyl) | Mipp | Mipp | (cyclopentyl) | |
| 112 | H | (prenyl) | adamantyl | Mes | (cyclopentyl) | |
| 113 | H | (prenyl) | DIPP | DIPP | (cyclopentyl) | |
| 114 | H | (prenyl) | IPP | IPP | (cyclopentyl) | |
| 115 | | (3-Ph-indenylidene) | 2-Me-C₆H₅ | 2-Me-C₆H₅ | (cyclopentyl) | |
| 116 | | (3-Ph-indenylidene) | Mes | Mes | (cyclopentyl) | |
| 117 | | (3-Ph-indenylidene) | Mipp | Mipp | (cyclopentyl) | |
| 118 | | (3-Ph-indenylidene) | adamantyl | Mes | (cyclopentyl) | |

TABLE 2-continued

Olefin Metathesis Catalysts of Formula (6)

| Catalyst | R¹ | R² | R³ | R⁴ | Rᵃ | Rᵇ |
|---|---|---|---|---|---|---|
| 119 | | (indene-Ph) | DIPP | DIPP | (cyclopentyl) | |
| 120 | | (indene-Ph) | IPP | IPP | (cyclopentyl) | |
| 121 | H | Ph | 2-Me-$C_6H_5$ | 2-Me-$C_6H_5$ | n-Bu | n-Bu |
| 122 | H | Ph | Mes | Mes | n-Bu | n-Bu |
| 123 | H | Ph | Mipp | Mipp | n-Bu | n-Bu |
| 124 | H | Ph | adamantyl | Mes | n-Bu | n-Bu |
| 125 | H | Ph | DIPP | DIPP | n-Bu | n-Bu |
| 126 | H | Ph | IPP | IPP | n-Bu | n-Bu |
| 127 | H | (isobutenyl) | 2-Me-$C_6H_5$ | 2-Me-$C_6H_5$ | n-Bu | n-Bu |
| 128 | H | (isobutenyl) | Mes | Mes | n-Bu | n-Bu |
| 129 | H | (isobutenyl) | Mipp | Mipp | n-Bu | n-Bu |
| 130 | H | (isobutenyl) | adamantyl | Mes | n-Bu | n-Bu |
| 131 | H | (isobutenyl) | DIPP | DIPP | n-Bu | n-Bu |
| 132 | H | (isobutenyl) | IPP | IPP | n-Bu | n-Bu |
| 133 | H | (2-isopropoxyphenyl) | 2-Me-$C_6H_5$ | 2-Me-$C_6H_5$ | n-Bu | n-Bu |
| 134 | H | (2-isopropoxyphenyl) | Mes | Mes | n-Bu | n-Bu |

TABLE 2-continued

Olefin Metathesis Catalysts of Formula (6)

| Catalyst | R¹ | R² | R³ | R⁴ | Rᵃ | Rᵇ |
|---|---|---|---|---|---|---|
| 135 | H | 2-isopropoxyphenyl | Mipp | Mipp | n-Bu | n-Bu |
| 136 | H | 2-isopropoxyphenyl | adamantyl | Mes | n-Bu | n-Bu |
| 137 | H | 2-isopropoxyphenyl | DIPP | DIPP | n-Bu | n-Bu |
| 138 | H | 2-isopropoxyphenyl | IPP | IPP | n-Bu | n-Bu |
| 139 | Ph | 3-phenylindenylidene | 2-Me-C₆H₅ | 2-Me-C₆H₅ | n-Bu | n-Bu |
| 140 | Ph | 3-phenylindenylidene | Mes | Mes | n-Bu | n-Bu |
| 141 | Ph | 3-phenylindenylidene | Mipp | Mipp | n-Bu | n-Bu |
| 142 | Ph | 3-phenylindenylidene | adamantyl | Mes | n-Bu | n-Bu |
| 143 | Ph | 3-phenylindenylidene | DIPP | DIPP | n-Bu | n-Bu |

TABLE 2-continued

Olefin Metathesis Catalysts of Formula (6)

| Catalyst | $R^1$ | $R^2$ | $R^3$ | $R^4$ | $R^a$ | $R^b$ |
|---|---|---|---|---|---|---|
| 144 | 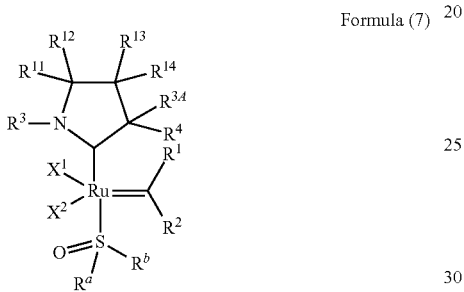 | Ph | IPP | IPP | n-Bu | n-Bu |

When, Y is N and $X^5$ is $CR^{3A}$ and M is ruthenium then, the olefin metathesis catalyst of Formula (4), is represented by the structure of Formula (7)

$$\text{Formula (7)}$$

wherein:
$R^1$ is hydrogen;
$R^2$ is unsubstituted hydrocarbyl, substituted hydrocarbyl, unsubstituted heteroatom-containing hydrocarbyl, or substituted heteroatom-containing hydrocarbyl; generally, $R^2$ is unsubstituted phenyl, substituted phenyl, $C_1$-$C_6$ alkyl or substituted 1-propenyl; or $R^1$ and $R^2$ are linked together to form an optionally substituted indenylidene;
$R^a$ is hydrogen, unsubstituted hydrocarbyl, substituted hydrocarbyl, unsubstituted heteroatom-containing hydrocarbyl, or substituted heteroatom-containing hydrocarbyl; generally, $R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;
$R^b$ is hydrogen, unsubstituted hydrocarbyl, substituted hydrocarbyl, unsubstituted heteroatom-containing hydrocarbyl, or substituted heteroatom-containing hydrocarbyl; generally $R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^b$ is methyl, ethyl, n-propyl, iso-propyl, n-butyl, tert-butyl, cyclohexyl or phenyl; or $R^a$ and $R^b$ are linked together to form a five or a six heterocyclic membered ring with the sulfoxide group;
$X^1$ and $X^2$ are independently halogen, trifluoroacetate, per-fluorophenols or nitrate; generally, $X^1$ and $X^2$ are independently Cl, Br, I or F; typically, $X^1$ and $X^2$ are independently Cl;
$R^3$ is unsubstituted hydrocarbyl, substituted hydrocarbyl, unsubstituted heteroatom containing hydrocarbyl, or substituted heteroatom-containing hydrocarbyl; generally, $R^3$ is unsubstituted $C_3$-$C_{10}$ cycloalkyl, substituted $C_3$-$C_{10}$ cycloalkyl, unsubstituted $C_5$-$C_{24}$ aryl, $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^3$ is adamantyl, 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl or 2-methyl-phenyl;
$R^{11}$, $R^{12}$, $R^{13}$ and $R^{14}$ are independently hydrogen, unsubstituted hydrocarbyl, substituted hydrocarbyl, unsubstituted heteroatom-containing hydrocarbyl, or substituted heteroatom-containing hydrocarbyl; generally, $R^{11}$, $R^{12}$, $R^{13}$ and $R^{14}$ are independently hydrogen, unsubstituted $C_1$-$C_{12}$ alkyl, substituted $C_1$-$C_{12}$ alkyl, unsubstituted $C_4$-$C_{12}$ cycloalkyl, substituted $C_4$-$C_{12}$ cycloalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ heteroaralkyl or substituted $C_6$-$C_{24}$ heteroaralkyl; typically, $R^{11}$ and $R^{12}$ are independently methyl and $R^{13}$ and $R^{14}$ are independently hydrogen;
$R^{3A}$ is hydrogen, unsubstituted hydrocarbyl, substituted hydrocarbyl, unsubstituted heteroatom-containing hydrocarbyl, or substituted heteroatom-containing hydrocarbyl; generally, $R^{3A}$ is unsubstituted $C_1$-$C_{12}$ alkyl, substituted $C_1$-$C_{12}$ alkyl, unsubstituted $C_4$-$C_{12}$ cycloalkyl, substituted $C_4$-$C_{12}$ cycloalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ heteroaralkyl or substituted $C_6$-$C_{24}$ heteroaralkyl; typically $R^{3A}$ is methyl, ethyl, n-propyl, or phenyl; or $R^{3A}$ together with $R^4$ can form a five to ten membered cycloalkyl or heterocyclic ring, with the carbon atom to which they are attached; and
$R^4$ is hydrogen, unsubstituted hydrocarbyl, substituted hydrocarbyl, unsubstituted heteroatom-containing hydrocarbyl, or substituted heteroatom-containing hydrocarbyl; generally, $R^4$ is unsubstituted $C_1$-$C_{12}$ alkyl, substituted $C_1$-$C_{12}$ alkyl, unsubstituted $C_4$-$C_{12}$ cycloalkyl, substituted $C_4$-$C_{12}$ cycloalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ heteroaralkyl or substituted $C_6$-$C_{24}$ heteroaralkyl; typically $R^4$ is methyl, ethyl, n-propyl, or phenyl.

Non-limiting examples of olefin metathesis catalysts represented by the structure of Formula (7) are described in Table (3), wherein $X^1$ is Cl, $X^2$ is Cl, $R^{11}$ is methyl, $R^{12}$ is methyl, $R^{13}$ is hydrogen and $R^{14}$ is hydrogen.

TABLE 3

Olefin Metathesis Catalysts of Formula (7)

| Catalyst | $R^1$ | $R^2$ | $R^a$ | $R^b$ | $R^3$ | $R^{3A}$ | $R^4$ |
|---|---|---|---|---|---|---|---|
| 145 | H | Ph | Me | Me | 2-Me-C$_6$H$_5$ | Me | Me |
| 146 | H | Ph | Me | Me | Mes | Me | Me |
| 147 | H | Ph | Me | Me | Mipp | Me | Me |
| 148 | H | Ph | Me | Me | EMP | Me | Me |
| 149 | H | Ph | Me | Me | DIPP | Me | Me |
| 150 | H | Ph | Me | Me | IPP | Me | Me |
| 151 | H | (2-methylpropenyl) | Me | Me | 2-Me-C$_6$H$_5$ | Me | Me |
| 152 | H | (2-methylpropenyl) | Me | Me | Mes | Me | Me |
| 153 | H | (2-methylpropenyl) | Me | Me | Mipp | Me | Me |
| 154 | H | (2-methylpropenyl) | Me | Me | EMP | Me | Me |
| 155 | H | (2-methylpropenyl) | Me | Me | DIPP | Me | Me |
| 156 | H | (2-methylpropenyl) | Me | Me | IPP | Me | Me |
| 157 | H | (2-isopropoxyphenyl) | Me | Me | 2-Me-C$_6$H$_5$ | Me | Me |
| 158 | H | (2-isopropoxyphenyl) | Me | Me | Mes | Me | Me |
| 159 | H | (2-isopropoxyphenyl) | Me | Me | Mipp | Me | Me |
| 160 | H | (2-isopropoxyphenyl) | Me | Me | EMP | Me | Me |

TABLE 3-continued
Olefin Metathesis Catalysts of Formula (7)
| Catalyst | R¹ | R² | Rᵃ | Rᵇ | R³ | R³,⁴ | R⁴ |
|---|---|---|---|---|---|---|---|
| 161 | H | 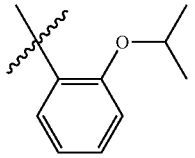 [SMILES: *c1ccccc1OC(C)C] | Me | Me | DIPP | Me | Me |
| 162 | H | 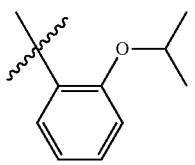 [SMILES: *c1ccccc1OC(C)C] | Me | Me | IPP | Me | Me |
| 163 | | 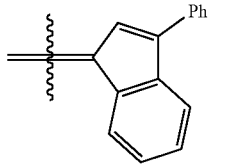 [SMILES: *=C1C=C(c2ccccc2)c2ccccc21] | Me | Me | 2-Me-C₆H₅ | Me | Me |
| 164 | | 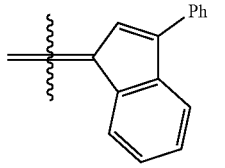 [SMILES: *=C1C=C(c2ccccc2)c2ccccc21] | Me | Me | Mes | Me | Me |
| 165 | | 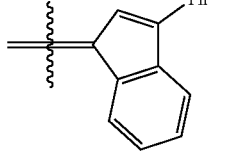 | Me | Me | Mipp | Me | Me |
| 166 | | 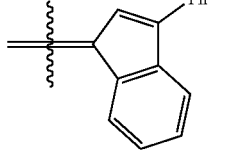 | Me | Me | EMP | Me | Me |
| 167 | | 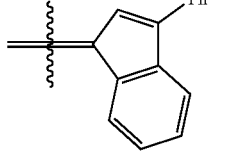 | Me | Me | DIPP | Me | Me |
| 168 | | 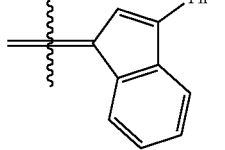 | Me | Me | IPP | Me | Me |
| 169 | H | Ph |  | | 2-Me-C₆H₅ | Me | Me |

TABLE 3-continued

Olefin Metathesis Catalysts of Formula (7)

| Catalyst | $R^1$ | $R^2$ | $R^a$, $R^b$ | $R^3$ | $R^{3A}$ | $R^4$ |
|---|---|---|---|---|---|---|
| 170 | H | Ph | (cyclohexyl ring) | Mes | Me | Me |
| 171 | H | Ph | (cyclohexyl ring) | Mipp | Me | Me |
| 172 | H | Ph | (cyclohexyl ring) | EMP | Me | Me |
| 173 | H | Ph | (cyclohexyl ring) | DIPP | Me | Me |
| 174 | H | Ph | (cyclohexyl ring) | IPP | Me | Me |
| 175 | H | 2-isopropoxyphenyl | (cyclohexyl ring) | 2-Me-C$_6$H$_5$ | Me | Me |
| 176 | H | 2-isopropoxyphenyl | (cyclohexyl ring) | Mes | Me | Me |
| 177 | H | 2-isopropoxyphenyl | (cyclohexyl ring) | Mipp | Me | Me |
| 178 | H | 2-isopropoxyphenyl | (cycloheptyl ring) | EMP | Me | Me |

TABLE 3-continued

Olefin Metathesis Catalysts of Formula (7)

| Catalyst | R¹ | R² | $R^a$ | $R^b$ | R³ | $R^{3,4}$ | R⁴ |
|---|---|---|---|---|---|---|---|
| 179 | H | (2-isopropoxyphenyl) | (cyclohexylidene) | DIPP | Me | | Me |
| 180 | H | (2-isopropoxyphenyl) | (cyclohexylidene) | IPP | Me | | Me |
| 181 | H | (2-methylpropenyl) | (cyclohexylidene) | 2-Me-C₆H₅ | Me | | Me |
| 182 | H | (2-methylpropenyl) | (cyclohexylidene) | Mes | Me | | Me |
| 183 | H | (2-methylpropenyl) | (cyclohexylidene) | Mipp | Me | | Me |
| 184 | H | (2-methylpropenyl) | (cyclohexylidene) | EMP | Me | | Me |
| 185 | H | (2-methylpropenyl) | (cyclohexylidene) | DIPP | Me | | Me |
| 186 | H | (2-methylpropenyl) | (cyclohexylidene) | IPP | Me | | Me |
| 187 | H | (3-phenylindenylidene) | (cyclohexylidene) | 2-Me-C6H5 | Me | | Me |

TABLE 3-continued

Olefin Metathesis Catalysts of Formula (7)

| Catalyst | R¹ | R² | Rᵃ | Rᵇ | R³ | R³,⁴ | R⁴ |
|---|---|---|---|---|---|---|---|
| 188 | | 1-Ph-indenylidene | -(CH₂)₄- (cyclopentyl ring) | | Mes | Me | Me |
| 189 | | 1-Ph-indenylidene | -(CH₂)₄- | | Mipp | Me | Me |
| 190 | | 1-Ph-indenylidene | -(CH₂)₄- | | EMP | Me | Me |
| 191 | | 1-Ph-indenylidene | -(CH₂)₄- | | DIPP | Me | Me |
| 192 | | 1-Ph-indenylidene | -(CH₂)₄- | | IPP | Me | Me |
| 193 | H | Ph | n-Bu | n-Bu | 2-Me-C₆H₅ | Me | Me |
| 194 | H | Ph | n-Bu | n-Bu | Mes | Me | Me |
| 195 | H | Ph | n-Bu | n-Bu | Mipp | Me | Me |
| 196 | H | Ph | n-Bu | n-Bu | EMP | Me | Me |
| 197 | H | Ph | n-Bu | n-Bu | DIPP | Me | Me |
| 198 | H | Ph | n-Bu | n-Bu | IPP | Me | Me |
| 199 | H | CH=C(CH₃)₂ | n-Bu | n-Bu | 2-Me-C₆H₅ | Me | R⁴ |
| 200 | H | CH=C(CH₃)₂ | n-Bu | n-Bu | Mes | Me | Me |
| 201 | H | CH=C(CH₃)₂ | n-Bu | n-Bu | Mipp | Me | Me |
| 202 | H | CH=C(CH₃)₂ | n-Bu | n-Bu | EMP | Me | Me |
| 203 | H | CH=C(CH₃)₂ | n-Bu | n-Bu | DIPP | Me | Me |

TABLE 3-continued

Olefin Metathesis Catalysts of Formula (7)

| Catalyst | R¹ | R² | $R^a$ | $R^b$ | R³ | $R^{3A}$ | R⁴ |
|---|---|---|---|---|---|---|---|
| 204 | H | (2-methylprop-1-en-1-yl) | n-Bu | n-Bu | IPP | Me | Me |
| 205 | H | (2-isopropoxyphenyl) | n-Bu | n-Bu | 2-Me-C₆H₅ | Me | Me |
| 206 | H | (2-isopropoxyphenyl) | n-Bu | n-Bu | Mes | Me | Me |
| 207 | H | (2-isopropoxyphenyl) | n-Bu | n-Bu | Mipp | Me | Me |
| 208 | H | (2-isopropoxyphenyl) | n-Bu | n-Bu | EMP | Me | Me |
| 209 | H | (2-isopropoxyphenyl) | n-Bu | n-Bu | DIPP | Me | Me |
| 210 | H | (2-isopropoxyphenyl) | n-Bu | n-Bu | IPP | Me | Me |
| 211 | | (3-phenyl-1H-inden-1-ylidene) | n-Bu | n-Bu | 2-Me-C₆H₅ | Me | Me |

TABLE 3-continued

Olefin Metathesis Catalysts of Formula (7)

| Catalyst | $R^1$ | $R^2$ | $R^a$ | $R^b$ | $R^3$ | $R^{3,4}$ | $R^4$ |
|---|---|---|---|---|---|---|---|
| 212 | | Ph (indene) | n-Bu | n-Bu | Mes | Me | Me |
| 213 | | Ph (indene) | n-Bu | n-Bu | Mipp | Me | Me |
| 214 | | Ph (indene) | n-Bu | n-Bu | EMP | Me | Me |
| 215 | | Ph (indene) | n-Bu | n-Bu | DIPP | Me | Me |
| 216 | | Ph (indene) | n-Bu | n-Bu | IPP | Me | Me | wherein EMP is

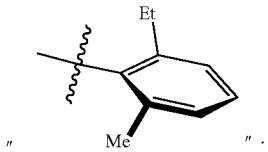

When, $L^1$ is a CAAC ligand of formula:

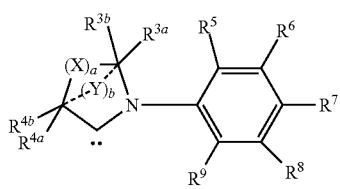

m is 0, and M is ruthenium then, the olefin metathesis catalyst of Formula (1), is represented by the structure of Formula (7A)

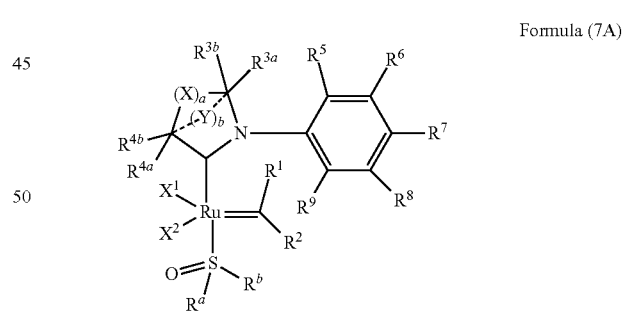

Formula (7A)

wherein $X^1$, $X^2$, $R^1$, $R^2$, $R^a$ and $R^b$ are as defined herein;
X is —$CR^{1a}R^{2a}$—;
a is 1 or 2;
$R^{1a}$ is H, optionally substituted $C_{1-24}$ alkyl, optionally substituted $C_3$-$C_{10}$ cycloalkyl, halogen, optionally substituted $C_5$-$C_{24}$ aryl, optionally substituted $C_6$-$C_{24}$ aralkyl, optionally substituted $C_1$-$C_{20}$ heteroalkyl, —C(O)$R^{21}$, —$OR^{22}$, CN, —$NR^{23}R^{24}$, $NO_2$, —$CF_3$, —$S(O)_xR^{25}$, —P(O)(OH)$_2$, —OP(O)(OH)$_2$, —$SR^{27}$, or together with $R^{2a}$ forms an optionally substituted spiro monocyclic or spiro polycyclic $C_3$-$C_{10}$ cycloalkyl or spiro heterocyclic ring, with the carbon atom to which they are attached, or together with $R^3$ or together with $R^4$ forms an optionally substituted polycyclic ring;

$R^{2a}$ is H, optionally substituted $C_{1-24}$ alkyl, optionally substituted $C_3$-$C_{10}$ cycloalkyl, halogen, optionally substituted $C_5$-$C_{24}$ aryl, optionally substituted $C_6$-$C_{24}$ aralkyl, optionally substituted $C_1$-$C_{20}$ heteroalkyl, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, or together with $R^{1a}$ forms a spiro monocyclic or spiro polycyclic $C_{3-10}$ cycloalkyl or spiro heterocyclic ring, with the carbon atom to which they are attached, or together with $R^3$ or together with $R^4$ forms an optionally substituted polycyclic ring;

Y is —CR$^{1b}$R$^{2b}$—;

b is 0, 1 or 2;

$R^{1b}$ is H, optionally substituted $C_{1-24}$ alkyl, optionally substituted $C_3$-$C_{10}$ cycloalkyl, halogen, optionally substituted $C_5$-$C_{24}$ aryl, optionally substituted $C_6$-$C_{24}$ aralkyl, optionally substituted $C_1$-$C_{20}$ heteroalkyl, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, or together with $R^{2b}$ forms a five-, six-, or ten-membered cycloalkyl or heterocyclic ring, with the carbon atom to which they are attached;

$R^{2b}$ is H, optionally substituted $C_{1-24}$ alkyl, optionally substituted $C_3$-$C_{10}$ cycloalkyl, halogen, optionally substituted $C_5$-$C_{24}$ aryl, optionally substituted $C_6$-$C_{24}$ aralkyl, optionally substituted $C_1$-$C_{20}$ heteroalkyl, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, or together with $R^{1b}$ forms a five-, six-, or ten-membered cycloalkyl or heterocyclic ring, with the carbon atom to which they are attached;

$R^{3a}$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^{1a}$ or together with $R^{2a}$ can form an optionally substituted polycyclic ring, or together with $R^{3a}$ can form an optionally substituted spiro monocyclic or spiro polycyclic $C_3$-$C_{10}$ cycloalkyl;

$R^{3b}$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^{1a}$ or together with $R^{2a}$ can form an optionally substituted polycyclic ring, or together with $R^3$ can form an optionally substituted spiro monocyclic or spiro polycyclic $C_3$-$C_{10}$ cycloalkyl;

$R^{4a}$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^{1a}$ or together with $R^{2a}$ can form an optionally substituted polycyclic ring, or together with $R^{4a}$ can form an optionally substituted spiro monocyclic or spiro polycyclic $C_3$-$C_{10}$ cycloalkyl;

$R^{4b}$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^{1a}$ or together with $R^{2a}$ can form an optionally substituted polycyclic ring, or together with $R^4$ can form an optionally substituted spiro monocyclic or spiro polycyclic $C_3$-$C_{10}$ cycloalkyl;

$R^5$ is H, optionally substituted $C_{1-24}$ alkyl, halogen-C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl or together with $R^5$ or together with $R^7$ can form an optionally substituted polycyclic ring;

$R^7$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^6$ or together with $R^8$ can form an optionally substituted polycyclic ring;

$R^8$ is H, optionally substituted $C_{1-24}$ alkyl, halogen-C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O)$R^{21}$, —OR$^{22}$, CN, —NR$^{23}$R$^{24}$, NO$_2$, —CF$_3$, —S(O)$_x$R$^{25}$, —P(O)(OH)$_2$, —OP(O)(OH)$_2$, —SR$^{27}$, optionally substituted heterocycle, optionally substituted $C_{3-10}$ cycloalkyl, optionally substituted $C_{5-24}$ aryl, optionally substituted $C_{3-8}$ cycloalkenyl, or together with $R^8$ can form a polycyclic ring;

$R^{21}$ is OH, OR$^{26}$, NR$^{23}$R$^{24}$, optionally substituted $C_{1-24}$ alkyl, optionally substituted $C_3$-$C_{10}$ cycloalkyl, optionally substituted heterocycle, optionally substituted $C_{5-24}$ aryl or optionally substituted $C_{3-8}$ cycloalkenyl;

$R^{22}$ is H, optionally substituted $C_{1-24}$ alkyl, optionally substituted $C_3$-$C_{10}$ cycloalkyl, optionally substituted heterocycle, optionally substituted $C_{5-24}$ aryl or optionally substituted $C_{3-8}$ cycloalkenyl;

$R^{23}$ is H, optionally substituted $C_{1-24}$ alkyl, optionally substituted $C_3$-$C_{10}$ cycloalkyl, optionally substituted heterocycle, optionally substituted $C_{5-24}$ aryl or optionally substituted $C_{3-8}$ cycloalkenyl;

$R^{24}$ is H, optionally substituted $C_{1-24}$ alkyl, optionally substituted $C_3$-$C_{10}$ cycloalkyl, optionally substituted heterocycle, optionally substituted $C_{5-24}$ aryl or optionally substituted $C_{3-8}$ cycloalkenyl;

$R^{25}$ is H, optionally substituted $C_{1-24}$ alkyl, OR$^{22}$, —NR$^{23}$R$^{24}$, optionally substituted heterocycle, optionally substituted $C_3$-$C_{10}$ cycloalkyl, optionally substituted $C_{5-24}$ aryl or optionally substituted $C_{3-8}$ cycloalkenyl;

$R^{26}$ is optionally substituted $C_{1-24}$ alkyl, optionally substituted $C_3$-$C_{10}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_3$-$C_{10}$ cycloalkyl, optionally substituted heterocycle, optionally substituted $C_{5-24}$ aryl or optionally substituted $C_{3-8}$ cycloalkenyl;

x is 1 or 2; and with the provisos a. when a is 2, then the "X-X" bond can be saturated or unsaturated;

b. when b is 2, the "Y-Y" bond can be saturated or unsaturated;

c. when a is 2, and the "X-X" bond is unsaturated, then $R^{2a}$ is nil;

d. when b is 1, then $R^{3a}$ and $R^{4a}$ are both nil;

e. when b is 2, then $R^{3a}$ and $R^{4a}$ are both nil; and f. when b is 2, and the "Y-Y" bond is unsaturated, then $R^{2b}$ is nil.

Depending on the values of a, b, X and Y, Moiety (A) of the CAAC ligand

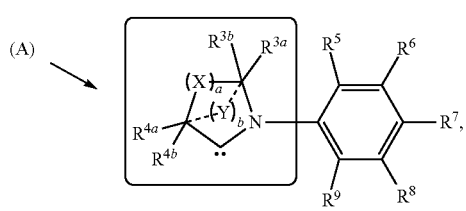

is represented by structures selected from Table (4).

TABLE 4

Structures of Moiety (A) of the CAAC ligands

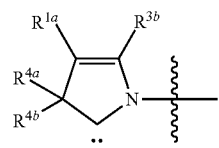

(A1)

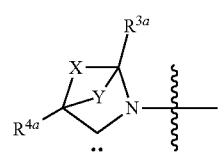

(A2)

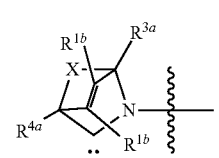

(A3)

TABLE 4-continued

Structures of Moiety (A) of the CAAC ligands

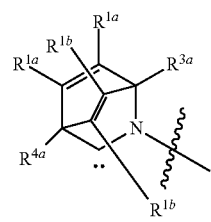

(A4)

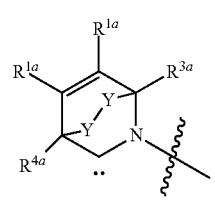

(A5)

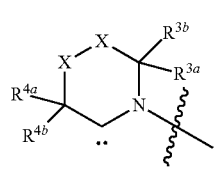

(A6)

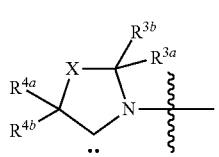

(A7)

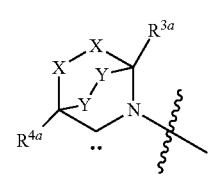

(A8)

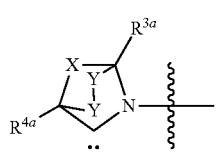

(A9)

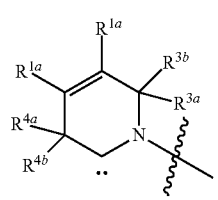

(A10)

TABLE 4-continued

Structures of Moiety (A) of the CAAC ligands (A11)

(A12)

(A13)

wherein: $R^1$, $R^2$, $R^a$, $R^b$ $R^{3a}$, $R^{3b}$, $R^{4a}$, $R^{4b}$, $R^5$, $R^6$, $R^7$, $R^8$ $R^9$, $R^{1a}$, $R^{1b}$, $X^1$, $X^2$, X, and Y are as defined herein.

The nomenclature of the structures of Formula (7A) is determined by the Moiety (A) structures selected from Table (4). For example, the structure below is assigned Formula (7A2), since Moiety (A2) is present in the CAAC ligand.

Formula (7A2)

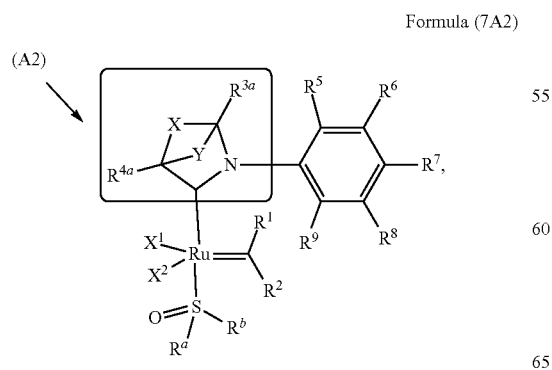

TABLE 5

Olefin Metathesis Catalysts of Formula (7A)

Formula (7A10)

Formula (7A13)

Formula (7A12)

Formula (7A6)

TABLE 5-continued
Olefin Metathesis Catalysts of Formula (7A)
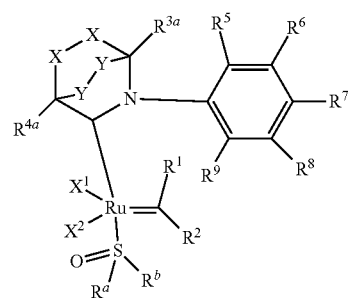
Formula (7A11)
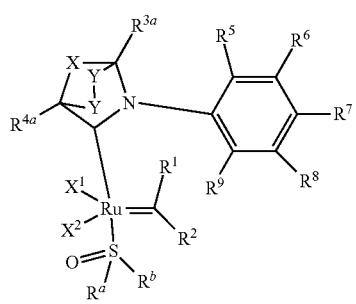
Formula (7A8)
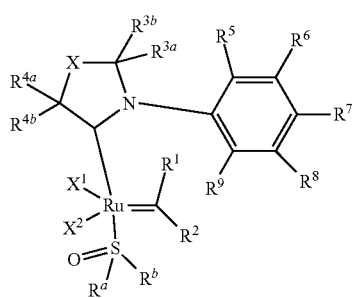
Formula (7A9)
Formula (7A7)
TABLE 5-continued
Olefin Metathesis Catalysts of Formula (7A)
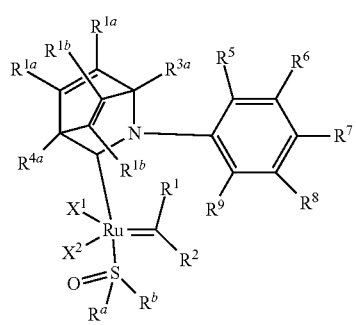
Formula (7A5)
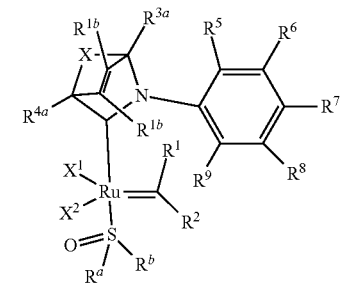
Formula (7A4)
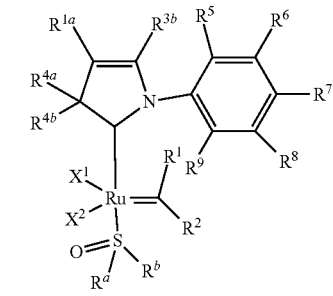
Formula (7A3)
Formula (7A1)
wherein: $R^1$, $R^2$, $R^a$, $R^b$ $R^{3a}$, $R^{3b}$, $R^{4a}$, $R^{4b}$, $R^5$, $R^6$, $R^7$, $R^8$ $R^9$, $R^{1a}$, $R^{1b}$, $X^1$, $X^2$, X, and Y are as defined herein.

When, $L^1$ is a N-heterocyclic carbene ligand represented by

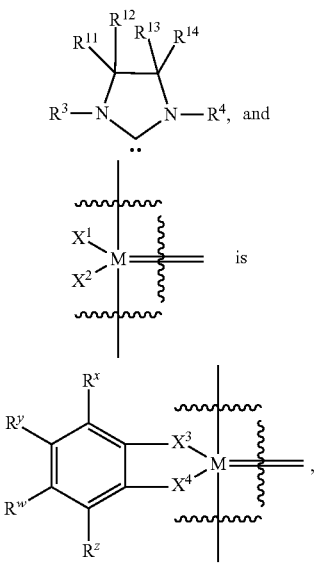

and $X^3$ and $X^4$ are independently S, and M is ruthenium then, the olefin metathesis catalyst of Formula (2), is represented by the structure of Formula (8)

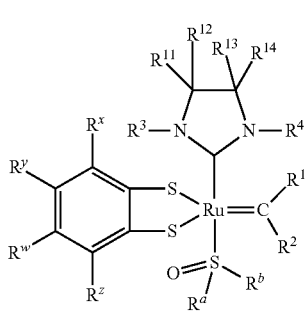

Formula (8)

wherein:
$R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^a$ is methyl, ethyl, n-propyl, iso-propyl, n-butyl, tert-butyl, cyclohexyl or phenyl;

$R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically, $R^b$ is methyl, ethyl, n-propyl, iso-propyl, n-butyl, tert-butyl, cyclohexyl or phenyl; or $R^a$ and $R^b$ are linked together to form a five or a six-heterocyclic membered ring with the sulfoxide group;

$R^3$ is unsubstituted $C_3$-$C_{10}$ cycloalkyl, substituted $C_3$-$C_{10}$ cycloalkyl, unsubstituted $C_5$-$C_{24}$ aryl, $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^3$ is adamantyl, 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 2,6-difluorophenyl, 3,5-di-tert-butylphenyl, 2,4-dimethylphenyl or 2-methyl-phenyl;

$R^4$ is unsubstituted $C_3$-$C_{10}$ cycloalkyl, substituted $C_3$-$C_{10}$ cycloalkyl, unsubstituted $C_5$-$C_{24}$ aryl, $C_5$-$C_{24}$ aryl substituted with up to three substituents selected from unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; typically, $R^4$ is 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 2,6-difluorophenyl, 3,5-di-tert-butylphenyl, 2,4-dimethylphenyl or 2-methyl-phenyl;

$R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene;

$R^{11}$, $R^{12}$, $R^{13}$, and $R^{14}$ are independently $C_1$-$C_6$ alkyl, or hydrogen; generally, $R^{11}$ is hydrogen or methyl, $R^{12}$ is hydrogen or methyl, $R^{13}$ is hydrogen and $R^{14}$ is hydrogen; typically, $R^{11}$, $R^{12}$, $R^{13}$, and $R^{14}$ are independently hydrogen; and $R^x$, $R^y$, $R^w$ and $R^z$ are independently $C_1$-$C_6$ alkyl, hydrogen, halogen, unsubstituted phenyl or substituted phenyl; generally $R^x$ is methyl, hydrogen or Cl, $R^y$ is hydrogen, $R^w$ is hydrogen, $R^z$ is Cl, t-butyl, hydrogen or phenyl; or $R^x$ and $R^y$ are linked together to form an unsubstituted bicyclic or polycyclic aryl or a substituted bicyclic or polycyclic aryl; or $R^w$ and $R^z$ are linked together to form an unsubstituted bicyclic or polycyclic aryl or a substituted bicyclic or polycyclic aryl; or $R^y$ and $R^w$ are linked together to form an unsubstituted bicyclic or polycyclic aryl or a substituted bicyclic or polycyclic aryl.

Non-limiting examples of olefin metathesis catalysts represented by the structure of Formula (8) are described in Table (6), wherein $R^a$ is methyl, $R^b$ is methyl, $R^{11}$ is hydrogen, $R^{12}$ is hydrogen, $R^{13}$ is hydrogen, $R^{14}$ is hydrogen, $R^y$ is hydrogen and $R^w$ is hydrogen.

TABLE 6

Olefin Metathesis Catalysts of Formula (8)

| Catalyst | $R^1$ | $R^2$ | $R^3$ | $R^4$ | $R^x$ | $R^z$ |
|---|---|---|---|---|---|---|
| 217 | H | Ph | 2-Me-$C_6H_5$ | 2-Me-$C_6H_5$ | Cl | Cl |
| 218 | H | Ph | Mes | Mes | Cl | Cl |
| 219 | H | Ph | Mipp | Mipp | Cl | Cl |
| 220 | H | Ph | DIPP | DIPP | Cl | Cl |
| 221 | H | Ph | IPP | IPP | Cl | Cl |
| 222 | H | 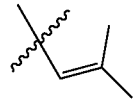 | 2-Me-$C_6H_5$ | 2-Me-$C_6H_5$ | Cl | Cl |

TABLE 6-continued

Olefin Metathesis Catalysts of Formula (8)

| Catalyst | R¹ | R² | R³ | R⁴ | $R^x$ | $R^z$ |
|---|---|---|---|---|---|---|
| 223 | H | (2-methylpropenyl) | Mes | Mes | Cl | Cl |
| 224 | H | (2-methylpropenyl) | Mipp | Mipp | Cl | Cl |
| 225 | H | (2-methylpropenyl) | DIPP | DIPP | Cl | Cl |
| 226 | H | (2-methylpropenyl) | IPP | IPP | Cl | Cl |
| 227 | H | (2-isopropoxyphenyl) | 2-Me-C₆H₅ | 2-Me-C₆H₅ | Cl | Cl |
| 228 | H | (2-isopropoxyphenyl) | Mes | Mes | Cl | Cl |
| 229 | H | (2-isopropoxyphenyl) | Mipp | Mipp | Cl | Cl |
| 230 | H | (2-isopropoxyphenyl) | DIPP | DIPP | Cl | Cl |
| 231 | H | (2-isopropoxy-3-phenyl-phenyl) | 2-Me-C₆H₅ | 2-Me-C₆H₅ | Cl | Cl |
| 232 | H | (2-isopropoxy-3-phenyl-phenyl) | Mes | Mes | Cl | Cl |
| 233 | H | (2-isopropoxy-3-phenyl-phenyl) | Mipp | Mipp | Cl | Cl |
| 234 | H | (2-isopropoxy-3-phenyl-phenyl) | DIPP | DIPP | Cl | Cl |
| 235 | H | (2-isopropoxy-3-phenyl-phenyl) | IPP | IPP | Cl | Cl |
| 236 | H | (2-isopropoxy-phenyl) | IPP | IPP | Cl | Cl |
| 237 | (3-phenyl-indenylidene) | | Ph 2-Me-C₆H₅ | 2-Me-C₆H₅ | Cl | Cl |
| 238 | (3-phenyl-indenylidene) | | Ph Mes | Mes | Cl | Cl |
| 239 | (3-phenyl-indenylidene) | | Ph Mipp | Me | Cl | Cl |
| 240 | (3-phenyl-indenylidene) | | Ph DIPP | DIPP | Cl | Cl |
| 241 | (3-phenyl-indenylidene) | | Ph IPP | Me | Cl | Cl |

TABLE 6-continued

Olefin Metathesis Catalysts of Formula (8)

| Catalyst | R¹ | R² | R³ | R⁴ | Rˣ | R^z |
|---|---|---|---|---|---|---|
| 242 | H | Ph | 2-Me-C₆H₅ | 2-Me-C₆H₅ | H | Ph |
| 243 | H | Ph | Mes | Mes | H | Ph |
| 244 | H | Ph | Mipp | Mipp | H | Ph |
| 245 | H | Ph | DIPP | DIPP | H | Ph |
| 246 | H | Ph | IPP | IPP | H | Ph |
| 247 | H | 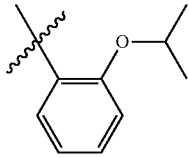 [SMILES: *c1ccccc1OC(C)C] | 2-Me-C₆H₅ | 2-Me-C₆H₅ | H | Ph |
| 248 | H | 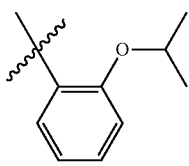 [SMILES: *c1ccccc1OC(C)C] | Mes | Mes | H | Ph |
| 249 | H | 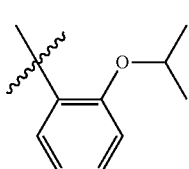 | Mipp | Mipp | H | Ph |
| 250 | H | 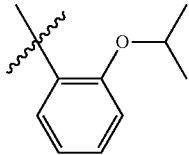 [SMILES: *c1ccccc1OC(C)C] | DIPP | DIPP | H | Ph |
| 251 | H | 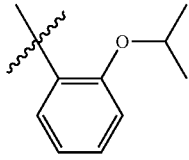 [SMILES: *c1ccccc1OC(C)C] | IPP | IPP | H | Ph |
| 252 | H | 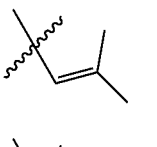 | 2-Me-C₆H₅ | 2-Me-C₆H₅ | H | Ph |
| 253 | H | 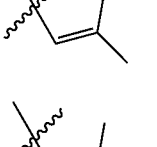 | Mes | Mes | H | Ph |
| 254 | H |  | Mipp | Mipp | H | Ph |
| 255 | H |  | DIPP | DIPP | H | Ph |
| 256 | H | 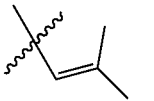 [SMILES: *C=C(C)C] | IPP | IPP | H | Ph |
| 257 | H | 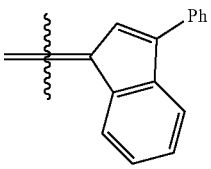 [SMILES: *=C1C=C(c2ccccc2)c2ccccc21] Ph | 2-Me-C₆H₅ | 2-Me-C₆H₅ | H | Ph |
| 258 | H | 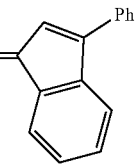 Ph | Mes | Mes | H | Ph |
| 259 | H | 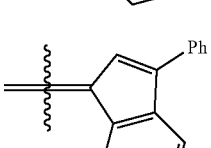 Ph | Mipp | Mipp | H | Ph |
| 260 | H | 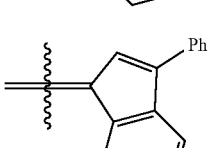 Ph | DIPP | DIPP | H | Ph |
| 261 | H | 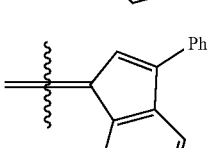 Ph | IPP | IPP | H | Ph |
| 262 | H | Ph | 2-Me-C₆H₅ | 2-Me-C₆H₅ | Me | t-Bu |
| 263 | H | Ph | Mes | Mes | Me | t-Bu |
| 264 | H | Ph | Mipp | Mipp | Me | t-Bu |
| 265 | H | Ph | DIPP | DIPP | Me | t-Bu |
| 266 | H | Ph | IPP | IPP | Me | t-Bu |
| 267 | H | 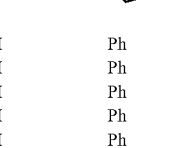 | 2-Me-C₆H₅ | 2-Me-C₆H₅ | Me | t-Bu |
| 268 | H | 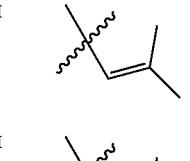 | Mes | Mes | Me | t-Bu |
| 269 | H |  | Mipp | Mipp | Me | t-Bu |

TABLE 6-continued

Olefin Metathesis Catalysts of Formula (8)

| Catalyst | R¹ | R² | R³ | R⁴ | Rˣ | Rᶻ |
|---|---|---|---|---|---|---|
| 270 | H | 2-methylpropenyl | DIPP | DIPP | Me | t-Bu |
| 271 | H | 2-methylpropenyl | IPP | IPP | Me | t-Bu |
| 272 | H | 2-isopropoxyphenyl | 2-Me-C₆H₅ | 2-Me-C₆H₅ | Me | t-Bu |
| 273 | H | 2-isopropoxyphenyl | Mes | Mes | Me | t-Bu |
| 274 | H | 2-isopropoxyphenyl | Mipp | Mipp | Me | t-Bu |
| 275 | H | 2-isopropoxyphenyl | DIPP | DIPP | Me | t-Bu |
| 276 | H | 2-isopropoxyphenyl | IPP | IPP | Me | t-Bu |
| 277 | Ph | 3-phenylindenylidene | 2-Me-C₆H₅ | 2-Me-C₆H₅ | Me | t-Bu |
| 278 | Ph | 3-phenylindenylidene | Mes | Mes | Me | t-Bu |
| 279 | Ph | 3-phenylindenylidene | Mipp | Mipp | Me | t-Bu |
| 280 | Ph | 3-phenylindenylidene | DIPP | DIPP | Me | t-Bu |
| 281 | Ph | 3-phenylindenylidene | IPP | IPP | Me | t-Bu |

Non-limiting examples of catalysts used in the present invention are represented by the structures:

C591

C731

C625

-continued
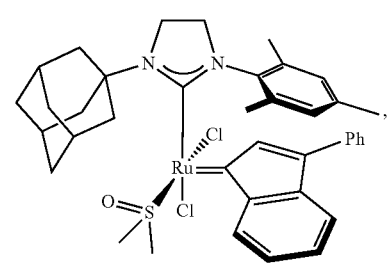
C763
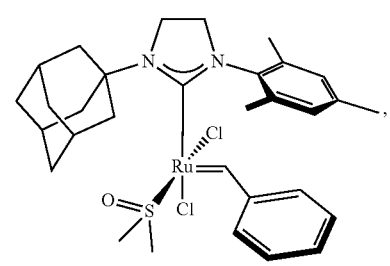
C663
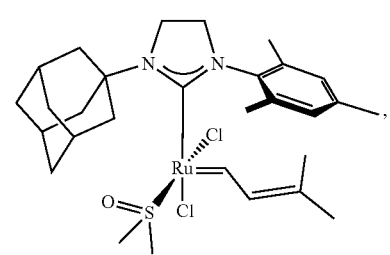
C641
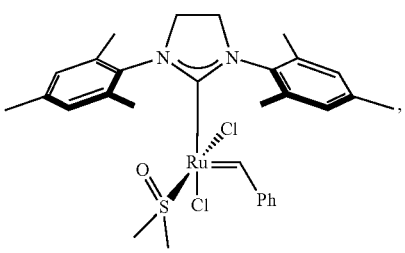
C647$_m$
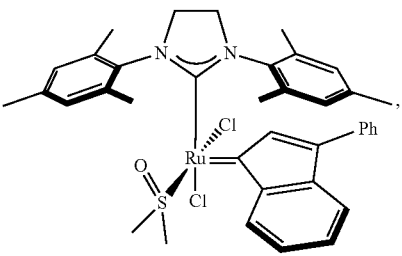
C747
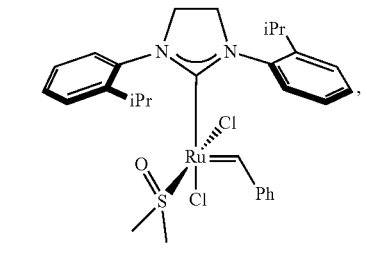
C647
-continued
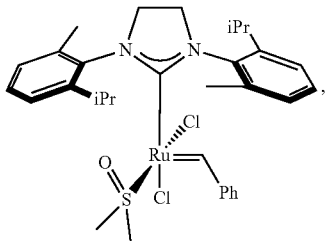
C676
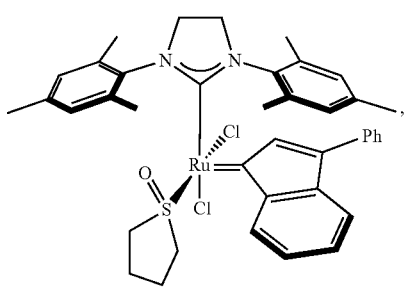
C773
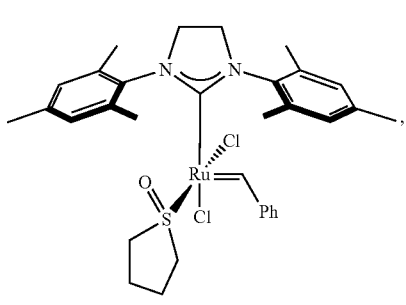
C673
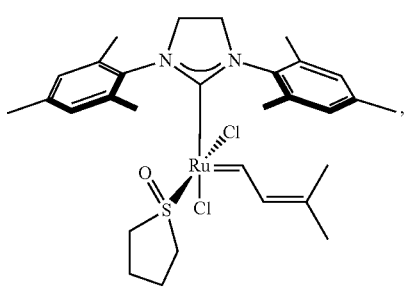
C651
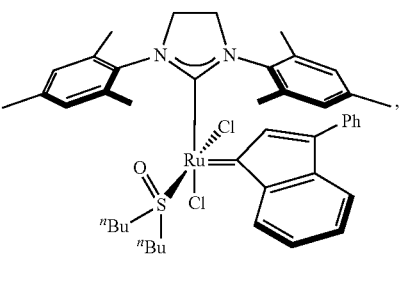
C831$_m$
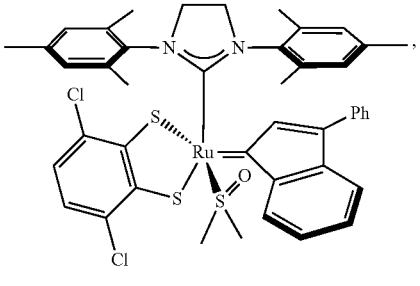
C885$_{ss}$ -continued

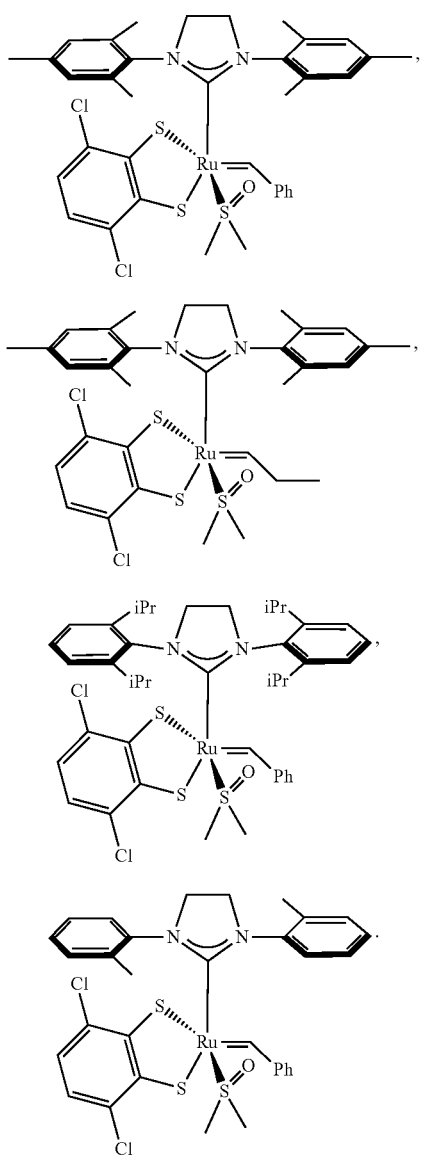

When L¹ is a CAAC ligand and

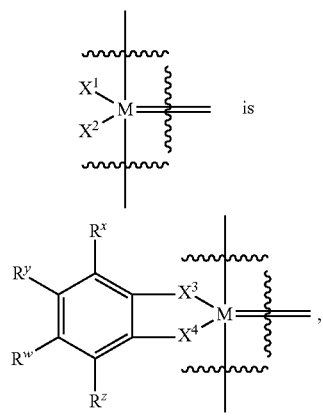

and, X³ and X⁴ are independently S, and M is ruthenium then, the olefin metathesis catalyst of Formula (2), is represented by the structure of Formula (8A)

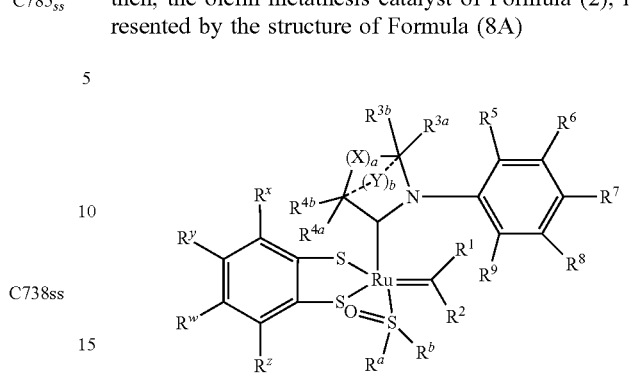

wherein: $R^1, R^2, R^a, R^b R^{3a}, R^{3b}, R^{4a}, R^{4b} R^5, R^6, R^7, R^8 R^9, R^x, R^y, R^z, R^w$, X, Y, a and b are as defined herein.

The nomenclature of the structures of Formula (8A) is determined by the Moiety (A) structures selected from Table (4). For example, the structure below is assigned Formula (8A10), since Moiety (A10) is present in the CAAC ligand.

Formula (8A10)

TABLE 7

Olefin Metathesis Catalysts of Formula (8A)

Formula (8A5)

TABLE 7-continued
Olefin Metathesis Catalysts of Formula (8A)
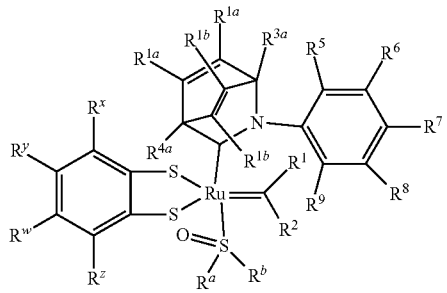
Formula (8A4)
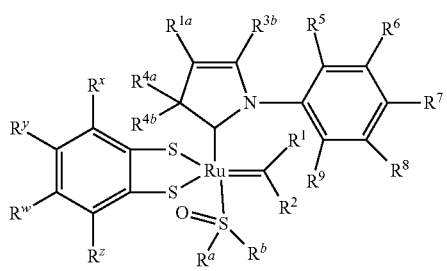
Formula (8A1)
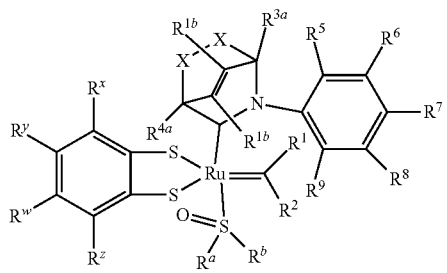
Formula (8A11)
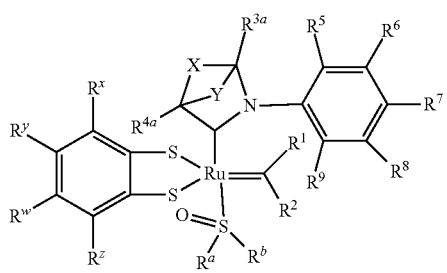
Formula (8A2)
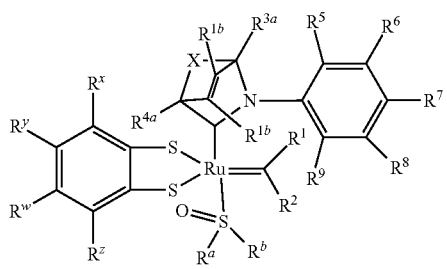
Formula (8A3)
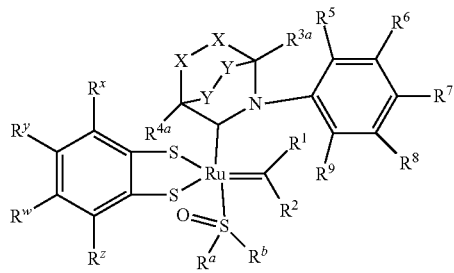
Formula (8A8)
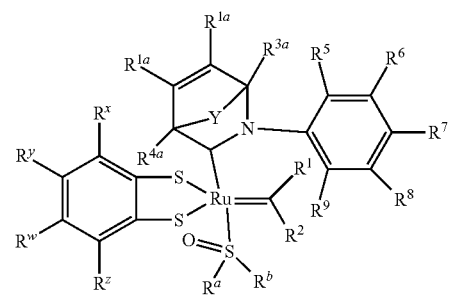
Formula (8A13)
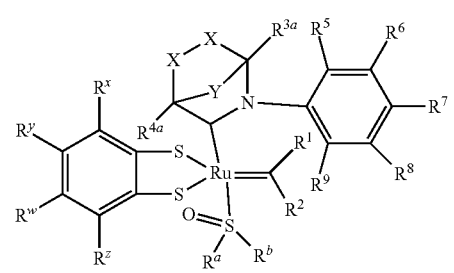
Formula (8A12)
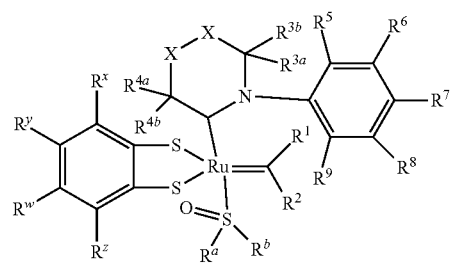
Formula (8A6)
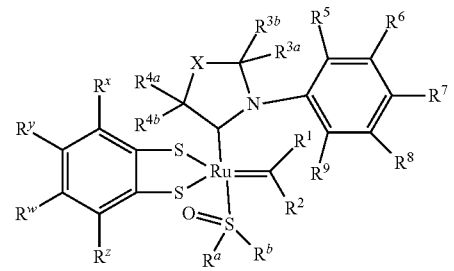
Formula (8A7)

TABLE 7-continued

Olefin Metathesis Catalysts of Formula (8A)

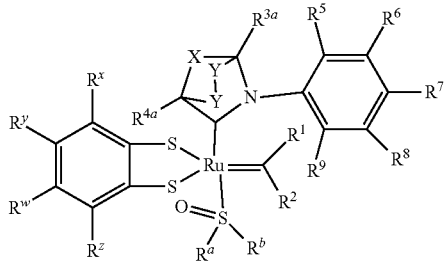

Formula (8A9)

wherein: $R^1$, $R^{1a}$, $R^{1b}$, $R^2$, $R^a$, $R^b$ $R^{3a}$, $R^{3b}$, $R^{4a}$, $R^{4b}$, $R^5$, $R^6$, $R^7$, $R^8$ $R^9$, $R^x$, $R^y$, $R^z$, $R^w$, X, Y, a and b are as defined herein.

In other embodiments of the invention, the Group 8 metal olefin metathesis catalysts of the invention are represented by the general structure of Formula (9)

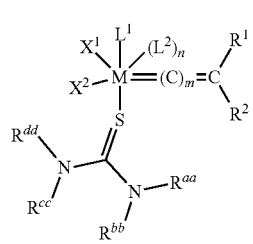

Formula (9)

wherein: M is a Group 8 transition metal; generally, M is ruthenium or osmium; typically, M is ruthenium;

$L^1$ and $L^2$ are independently neutral electron donor ligands;

n is 0 or 1; typically, n is 0;

m is 0, 1 or 2; generally, m is 0 or 1; typically, m is 0;

$R^{aa}$ is unsubstituted hydrocarbyl, substituted hydrocarbyl, unsubstituted heteroatom-containing hydrocarbyl, or substituted heteroatom-containing hydrocarbyl; generally $R^{aa}$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^{aa}$ is methyl, ethyl, n-propyl, iso-propyl, n-butyl, tert-butyl, cyclohexyl, benzyl or phenyl;

$R^{bb}$ is unsubstituted hydrocarbyl, substituted hydrocarbyl, unsubstituted heteroatom-containing hydrocarbyl, or substituted heteroatom-containing hydrocarbyl; generally $R^{bb}$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^{bb}$ is methyl, ethyl, n-propyl, iso-propyl, n-butyl, tert-butyl, cyclohexyl, benzyl or phenyl;

$R^{aa}$ and $R^{bb}$ can be linked to form a five-, six- or seven-membered heterocycle ring with the nitrogen atom they are linked to;

$R^{cc}$ is unsubstituted hydrocarbyl, substituted hydrocarbyl, unsubstituted heteroatom-containing hydrocarbyl, or substituted heteroatom-containing hydrocarbyl; generally $R^{cc}$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^{cc}$ is methyl, ethyl, n-propyl, iso-propyl, n-butyl, tert-butyl, cyclohexyl, benzyl or phenyl;

$R^{dd}$ is unsubstituted hydrocarbyl, substituted hydrocarbyl, unsubstituted heteroatom-containing hydrocarbyl, or substituted heteroatom-containing hydrocarbyl; generally $R^d$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; typically $R^{dd}$ is methyl, ethyl, n-propyl, iso-propyl, n-butyl, tert-butyl, cyclohexyl, benzyl or phenyl;

$R^{cc}$ and $R^{dd}$ can be linked to form a five-, six- or seven-membered heterocycle ring with the nitrogen atom they are linked to;

$R^{bb}$ and $R^{cc}$ can be linked to form a five-, six- or seven-membered heterocycle ring with the nitrogen atoms they are linked to;

$X^1$ and $X^2$ are independently anionic ligands; generally, $X^1$ and $X^2$ are independently halogen, trifluoroacetate, per-fluorophenols or nitrate; typically, $X^1$ and $X^2$ are independently chlorine, bromine, iodine or fluorine;

$R^1$ and $R^2$ are independently hydrogen, unsubstituted hydrocarbyl, substituted hydrocarbyl, unsubstituted heteroatom-containing hydrocarbyl, or substituted heteroatom-containing hydrocarbyl; typically, $R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene.

In some embodiments of Formula (9),

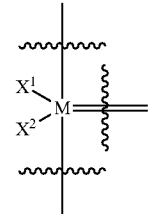

is represented by

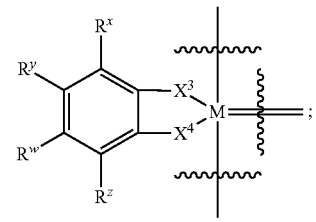

wherein: M, $X^1$, $X^2$, $X^3$, $X^4$, $R^x$, $R^y$, $R^w$ and $R^z$ are as defined herein.

In some embodiments of Formula (9), $L^1$ is

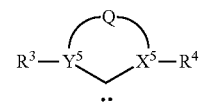

represented by

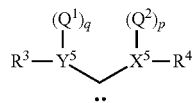

or by or L¹ is a CAAC ligand represented by

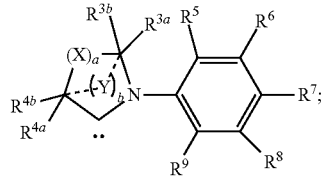

wherein Q¹, Q², p, q, R$^{3a}$, R$^{3b}$, R$^{4a}$, R$^{4b}$, R³, R⁴, R⁵ R⁶, R⁷, R⁸, R⁹, X⁵, Y⁵, a and b are as defined herein.

When M is Ru, n is 0, m is 0 and L¹ is a NHC ligand of structures

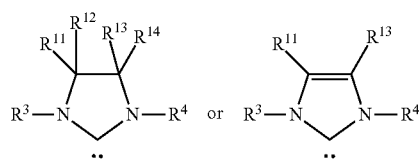

then the invention provides a catalyst represented by structures

Formula (10)

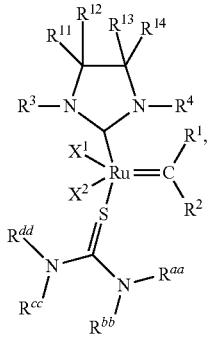

Formula (11)

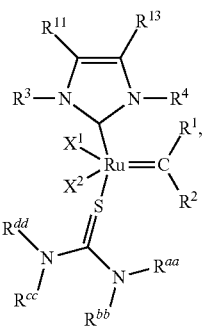

and when

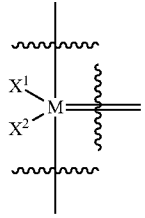

is represented by

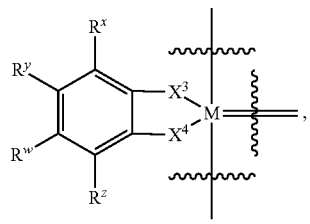

then the invention provides a catalyst represented by structures

Formula (12)

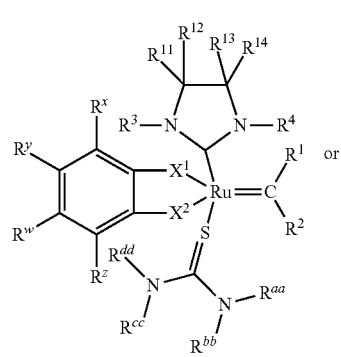

or

Formula (13)

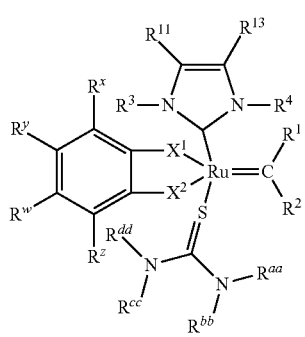

wherein R¹, R², R³, R⁴, R$^{aa}$, R$^{bb}$ R$^{cc}$, R$^{dd}$, X¹, X², X³, X⁴, R¹¹, R¹², R¹³, R¹⁴, R$^x$, R$^y$, R$^w$ and R$^z$ are as defined herein.

When M is Ru, n is 0, m is 0 and L¹ is a CAAC ligand then the invention provides a catalyst represented by the structure of Formula (10A)

Formula (10A)

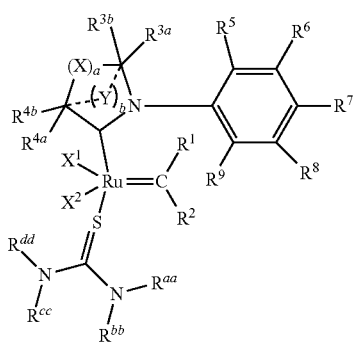

wherein: $R^1$, $R^2$, $X^1$, $X^2$, $R^{3a}$, $R^{3b}$, $R^{4a}$, $R^{4b}$, $R^{aa}$, $R^{bb}$, $R^{cc}$, $R^{dd}$, $R^5$, $R^6$, $R^7$, $R^8$ $R^9$, X, Y, a and b are as defined herein.

The nomenclature of the structures of Formula (10A) is determined by the Moiety (A) structures selected from Table (4). For example, the structure below is assigned Formula (10A10), since Moiety (A10) is present in the CAAC ligand.

Formula (10A10)

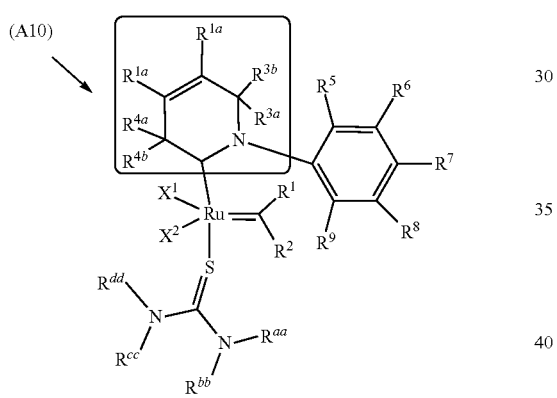

TABLE 8

Olefin Metathesis Catalysts of Formula (10A)

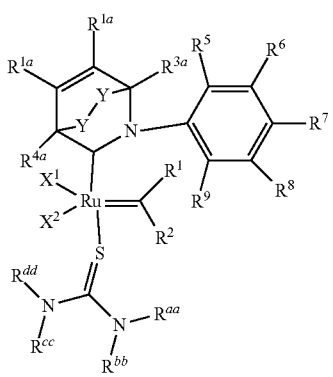

Formula (10A5)

TABLE 8-continued

Olefin Metathesis Catalysts of Formula (10A)

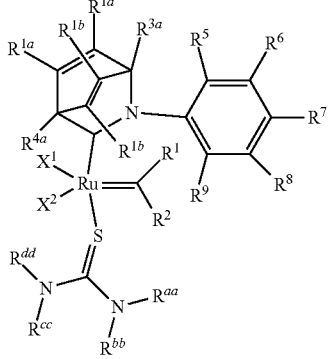

Formula (10A4)

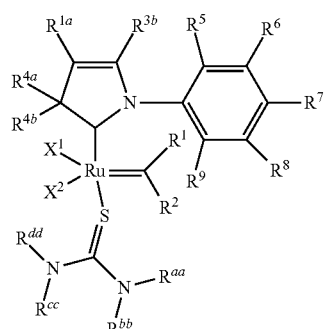

Formula (10A1)

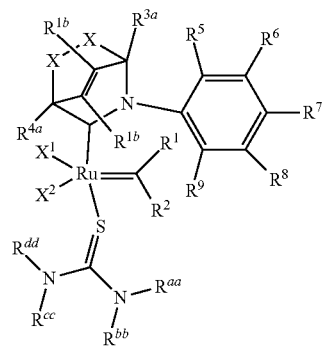

Formula (10A11)

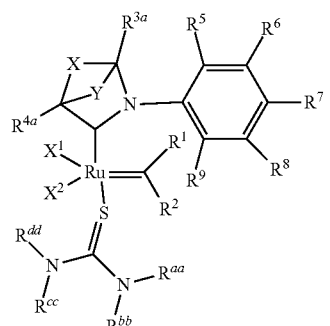

Formula (10A2)

TABLE 8-continued

Olefin Metathesis Catalysts of Formula (10A)

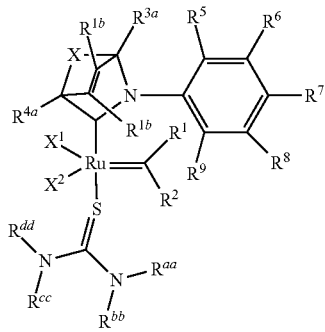

Formula (10A3)

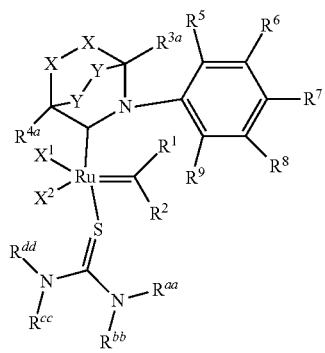

Formula (10A8)

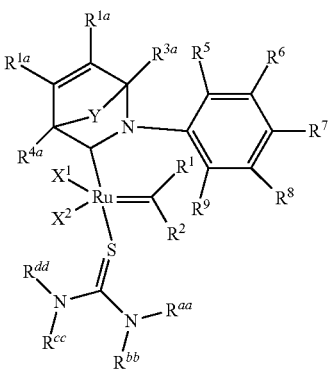

Formula (10A13)

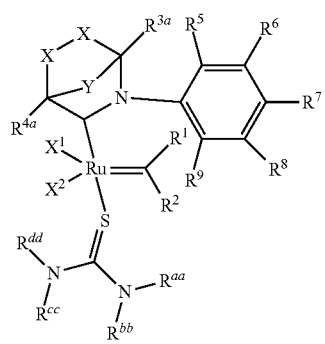

Formula (10A12)

TABLE 8-continued

Olefin Metathesis Catalysts of Formula (10A)

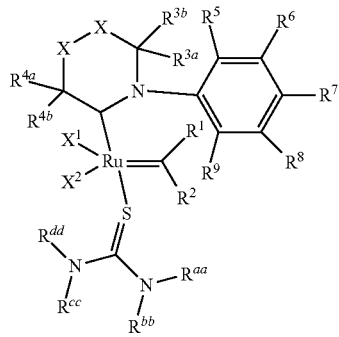

Formula (10A6)

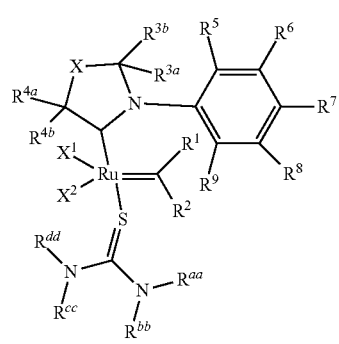

Formula (10A7)

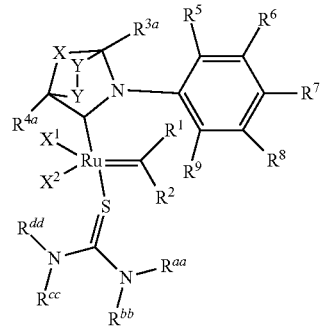

Formula (10A9)

wherein: $R^1$, $R^{1a}$, $R^{1b}$, $R^2$, $R^a$, $R^b$ $R^{3a}$, $R^{3b}$, $R^{4a}$, $R^{4b}$, $R^{aa}$, $R^{bb}$, $R^{cc}$, $R^{dd}$, $R^5$, $R^6$, $R^7$, $R^8$ $R^9$, $R^x$, $R^y$, $R^z$, $R^w$, X, Y, a and b are as defined herein.

When M is Ru, n is 0, m is 0,

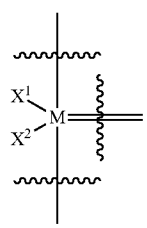

is represented by

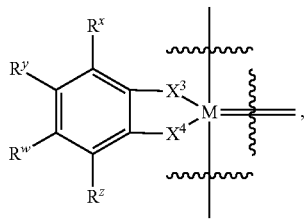

X³ and X⁴ are S, and L¹ is a CAAC ligand then the invention provides a catalyst represented by the structure of Formula (12A)

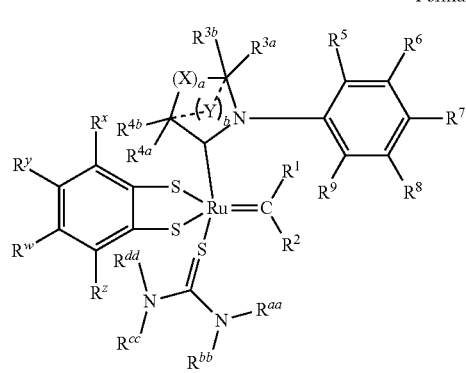

Formula (12A)

wherein: $R^1$, $R^2$, $R^{3a}$, $R^{3b}$, $R^{4a}$, $R^{4b}$, $R^{aa}$, $R^{bb}$, $R^{cc}$, $R^{dd}$, $R^5$, $R^6$, $R^7$, $R^8$ $R^9$, $R^x$, $R^y$, $R^w$, $R^z$, X, Y, a and b are as defined herein.

The nomenclature of the structures of Formula (12A) is determined by the Moiety (A) structures selected from Table (4). For example, the structure below is assigned Formula (12A5), since Moiety (A5) is present in the CAAC ligand.

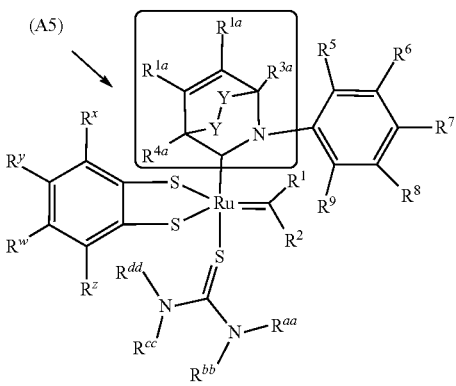

Formula (12A5)

TABLE 9

Olefin Metathesis Catalysts of Formula (12A)

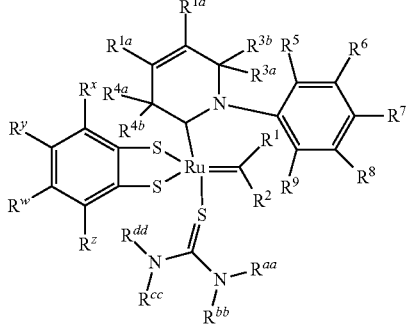

Formula (12A10)

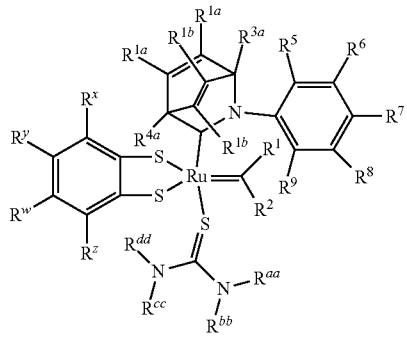

Formula (12A4)

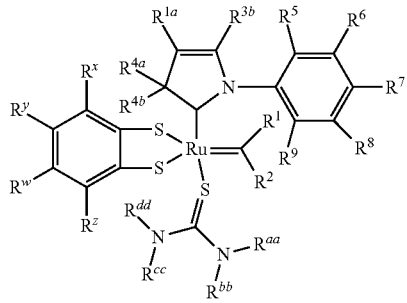

Formula (12A1)

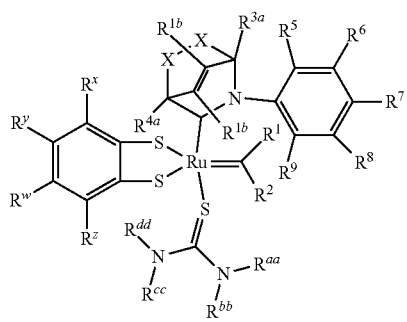

Formula (12A11)

TABLE 9-continued

Olefin Metathesis Catalysts of Formula (12A)

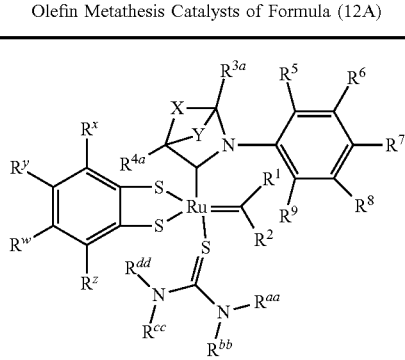

Formula (12A2)

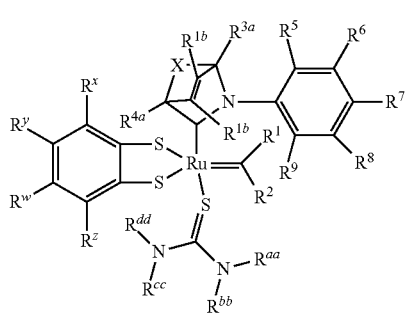

Formula (12A3)

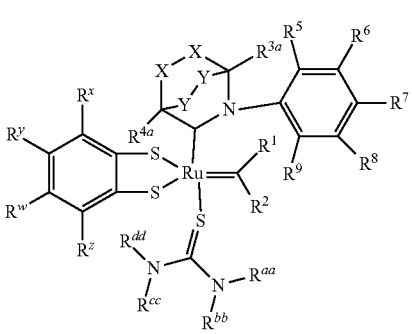

Formula (12A8)

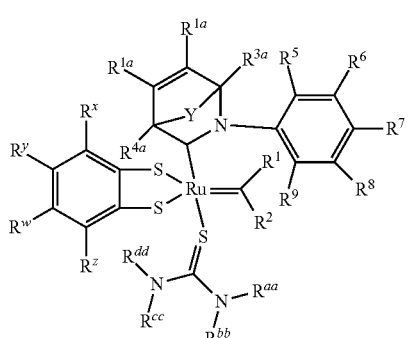

Formula (12A13)

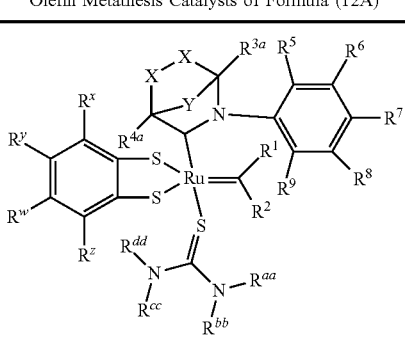

Formula (12A12)

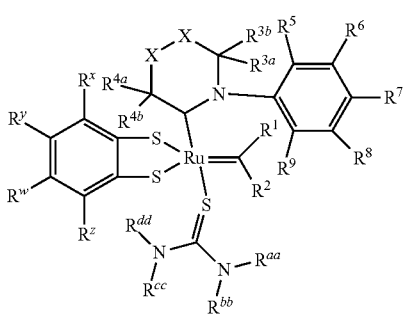

Formula (12A6)

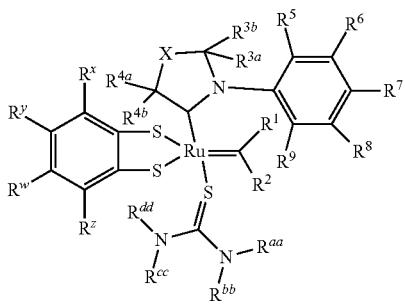

Formula (12A7)

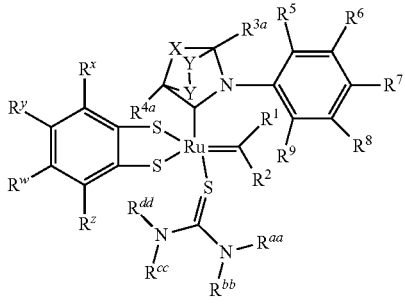

Formula (12A9)

wherein: $R^1$, $R^2$, $R^{1a}$, $R^{1b}$, $R^{3a}$, $R^{3b}$, $R^{4a}$, $R^{4b}$, $R^{aa}$, $R^{bb}$, $R^{cc}$, $R^{dd}$, $R^5$, $R^6$, $R^7$, $R^8$ $R^9$, $R^x$, $R^y$, $R^w$, $R^z$ X, Y, a and b are as defined herein.

Non-limiting examples of catalysts used in the present invention are represented by the structures:

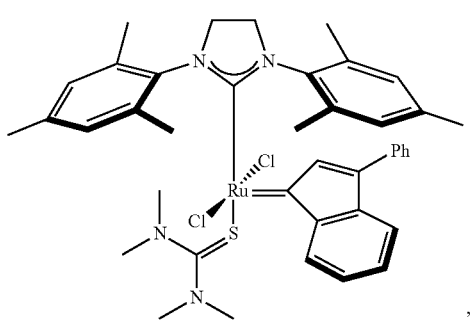

C801TU,

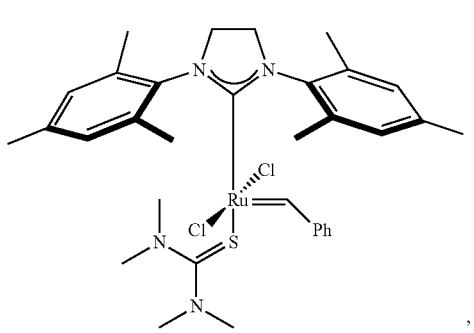

C701TU,

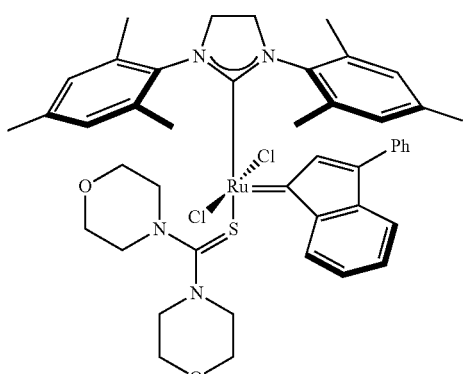

C885TU,

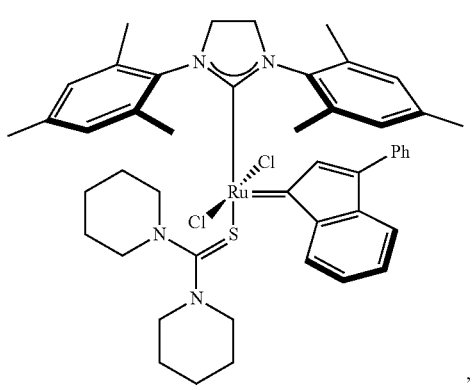

C881TU,

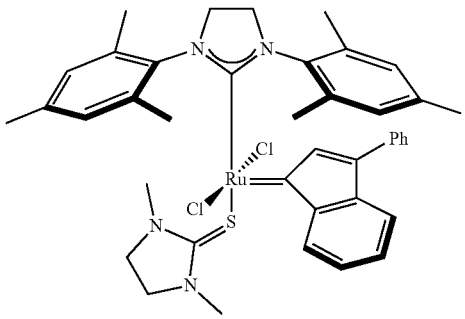

C799TU,

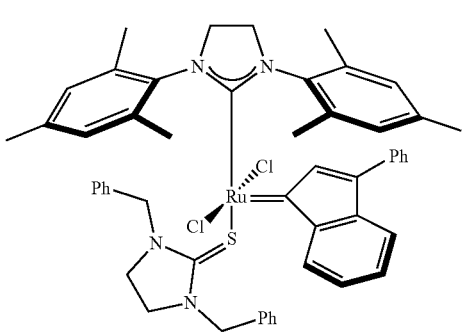

C951TU,

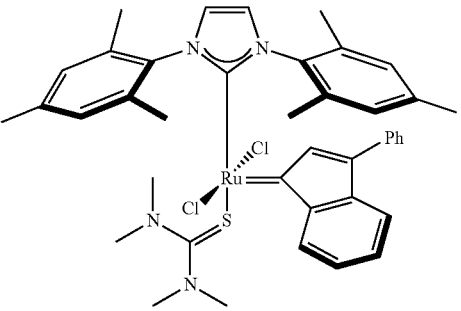

C799uTU.

Description of the Macrocyclic Embodiments

In one embodiment, the ring-close metathesis macrocyclic product comprises a product internal olefin, wherein the product internal olefin is in a Z-configuration.

In some embodiments, the invention provides a method that produces a compound (i.e., a product, olefin product; e.g., ring-close metathesis product) having a carbon-carbon double bond (e.g., a product internal olefin) in a Z:E ratio greater than 95:5, greater than 96:4, greater than 97:3, greater than 98:2, or in some cases, greater than 99:1. In some cases, about 100% of the carbon-carbon double bond produced in the metathesis reaction may have a Z configuration. The Z or cis selectivity may also be expressed as a percentage of product formed (e.g., ring-close metathesis product). In some cases, the product (e.g., ring-close metathesis product) may be greater than 50% Z, greater than 60% Z, greater than 70% Z, greater than 80% Z, greater than 90% Z, greater than 95% Z, greater than 96% Z, greater than 97% Z, greater than about 98% Z, greater than 99% Z, or in some cases greater than 99.5% Z.

In one embodiment, the ring-closing metathesis reaction product has a carbon-carbon double bond in a Z configuration and is represented by the structure of Formula (A):

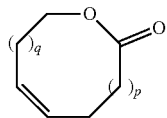

Formula (A)

wherein:
q is 1, 2, 3, or 4; and
p is 4, 5, 6, or 7.

In another embodiment, the at least one ring-close metathesis product is represented by the structure of Formula (A), wherein q is 2 and p is 4 or 6.

In another embodiment, the at least one ring-close metathesis product is represented by the structure of Formula (A), wherein q is 1, 2, 3 or 4 and p is 6 or 7.

In another embodiment, the at least one ring-close metathesis product is represented by the structure of Formula (A), wherein, q is 1 or 2 and p is 6.

In another embodiment, the at least one ring-close metathesis product is represented by the structure of Formula (A), wherein q is 1, 2, 3 or 4 and p is 7.

In another embodiment, the at least one ring-close metathesis product is represented by the structure of Formula (A), wherein, q is 1 and p is 6.

In another embodiment, the ring-closing metathesis reaction product has a carbon-carbon double bond in a Z configuration and is represented by the structure of Formula (B):

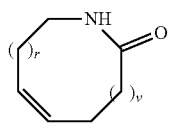

Formula (B)

wherein:
r is 1, 2, 3, or 4; and
v is 4, 5, 6, or 7.

In another embodiment, the at least one ring-close metathesis product is represented by the structure of Formula (B), wherein r is 2 and v is 4 or 6.

In another embodiment, the at least one ring-close metathesis product is represented by the structure of Formula (B), wherein r is 1, 2, 3 or 4 and v is 6 or 7.

In another embodiment, the at least one ring-close metathesis product is represented by the structure of Formula (B), wherein, r is 1 or 2 and v is 6.

In another embodiment, the at least one ring-close metathesis product is represented by the structure of Formula (B), wherein r is 1, 2, 3 or 4 and v is 7.

In another embodiment, the at least one ring-close metathesis product is represented by the structure of Formula (B), wherein, r is 1 and v is 6.

In one embodiment, the diene starting material bearing a Z-olefin moiety can be represented by Formula (E):

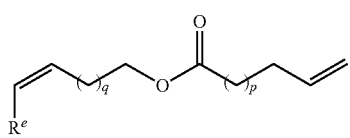

Formula (E)

wherein:
$R^e$ is H, methyl, ethyl, or propyl;
q is 1, 2, 3, or 4;
p is 4, 5, 6, or 7.

In one embodiment, the diene starting material bearing a Z-olefin moiety can be represented by Formula (E), wherein $R^e$ is methyl, q is 2 and p is 4 or 6.

In one embodiment, the diene starting material bearing a Z-olefin moiety can be represented by Formula (E), wherein $R^e$ is ethyl, q is 1, 2, 3 or 4 and p is 6 or 7.

In one embodiment, the diene starting material bearing a Z-olefin moiety can be represented by Formula (E), wherein $R^e$ is ethyl, q is 1 or 2 and p is 6.

In one embodiment, the diene starting material bearing a Z-olefin moiety can be represented by Formula (E), wherein $R^e$ is ethyl, q is 1, 2, 3 or 4 and p is 7.

In one embodiment, the diene starting material bearing a Z-olefin moiety can be represented by Formula (E), wherein $R^e$ is ethyl, q is 1 and p is 6.

In another embodiment, the invention relates to a method for performing a ring-closing metathesis reaction, comprising: contacting a diene starting material bearing a Z-olefin moiety of Formula (E), with at least one olefin metathesis catalyst of Formula (5), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one olefin metathesis catalyst of Formula (6), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one olefin metathesis catalyst of Formula (7), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (8), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (8A), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (9), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (10), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (10A), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (11), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (12), under conditions effective to promote the formation of at least one Z-macrocycle product of Formula (A), with a Z-configuration greater than 80% Z.

In another embodiment, the invention relates to a method for performing a ring-closing metathesis reaction, comprising: contacting a diene starting material bearing a Z-olefin moiety of Formula (E), with at least one Z-stereoretentive olefin metathesis catalyst of Formula (12A), under conditions effective to promote the formation of at least one Z-macrocycle product of Formula (A), with a Z-configuration greater than 80% Z.

In one embodiment, the invention provides for a method of synthesizing a musk macrocycle, represented by Formula (A), comprising, a ring closing metathesis reaction on a diene of Formula (E), in the presence of at least one metathesis catalyst under conditions sufficient to form a metathesis product, wherein the at least one metathesis catalyst is represented by the structure of Formula (5), and wherein $R^e$, q, p, $R^1$, $R^2$, $R^a$, $R^b$, $X^1$, $X^2$, $R^3$ and $R^4$ are as defined herein.

In one embodiment, the invention provides for a method of synthesizing a musk macrocycle, represented by Formula (A), comprising, a ring closing metathesis reaction on a diene of Formula (E), in the presence of at least one metathesis catalyst under conditions sufficient to form a metathesis product, wherein the at least one metathesis catalyst is represented by the structure of Formula (8), and wherein $R^e$, q, p, $R^1$, $R^2$, $R^a$, $R^b$, $R^{11}$, $R^{12}$, $R^{13}$, $R^{14}$, $R^3$, $R^4$, $R^x$, $R^y$, $R^z$ and $R^w$ are as defined herein.

In one embodiment a Z-olefin moiety represented by Formula (E), wherein R is methyl, q is 2 and p is 4 or 6; is reacted in the presence of a catalyst represented by of Formula (8), wherein $R^1$ is hydrogen, $R^2$ is phenyl, ethyl or together with $R^1$ can form a phenylindenylidene, $R^a$ is methyl, $R^b$ is methyl, $R^{11}$ is hydrogen, $R^{12}$ is hydrogen, $R^{13}$ is hydrogen, $R^{14}$ is hydrogen, $R^3$ is 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 2,6-difluorophenyl, 3,5-di-tert-butylphenyl, 2,4-dimethylphenyl or 2-methyl-phenyl $R^4$ is 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 2,6-difluorophenyl, 3,5-di-tert-butylphenyl, 2,4-dimethylphenyl or 2-methyl-phenyl, $R^x$ is Cl, $R^y$ is hydrogen, $R^z$ is Cl and $R^w$ is hydrogen, to give a musk macrocycle of Formula (A) with a Z-configuration greater than 80% Z.

In one embodiment, the invention provides for a method of synthesizing a musk macrocycle of Formula (A) comprising, performing a ring closing metathesis reaction on a diene of Formula (E) wherein $R^e$ is H, methyl, ethyl, or propyl; q is 1, 2, 3, or 4; p is 4, 5, 6, or 7; in the presence of at least one metathesis catalyst under conditions sufficient to form a metathesis product, wherein the at least one metathesis catalyst is represented by the structure of Formula (5), wherein the catalyst is selected from: C591, C731, C625, C763, C663, C641, C647m, C747, C647, C676, C773, C673, C651 and C831m.

In one embodiment, the invention provides for a method of synthesizing a musk macrocycle of Formula (A) comprising, performing a ring closing metathesis reaction on a diene of Formula (E) wherein $R^e$ is H, methyl, ethyl, or propyl; q is 1, 2, 3, or 4; p is 4, 5, 6, or 7; in the presence of at least one metathesis catalyst under conditions sufficient to form a metathesis product, wherein the at least one metathesis catalyst is represented by the structure of Formula (8), wherein the catalyst is selected from: C885ss, C785ss, C738ss, C869ss, and C725ss.

In one embodiment, the invention provides for a method of synthesizing a musk macrocycle of Formula (B) comprising, performing a ring closing metathesis reaction on a diene of Formula (E) wherein $R^e$ is H, methyl, ethyl, or propyl; r is 1, 2, 3, or 4; v is 4, 5, 6, or 7; in the presence of at least one metathesis catalyst under conditions sufficient to form a metathesis product, wherein the at least one metathesis catalyst is represented by the structure of Formula (12), wherein the catalyst is selected from: $C801_{TU}$, $C701_{TU}$, $C885_{TU}$, $C881_{TU}$, $C799_{TU}$, $C951_{TU}$ and $C799u_{TU}$.

In one embodiment, the invention provides for a method of synthesizing dilactones, such as ethylene brassylate (x=9) and ethylene undecanedioate (x=7), both used in perfumery, wherein the starting material can be obtained from a cross metathesis reaction in the presence of at least one metal olefin metathesis catalyst of the invention. The olefin is further reduced and cyclized using known procedures.

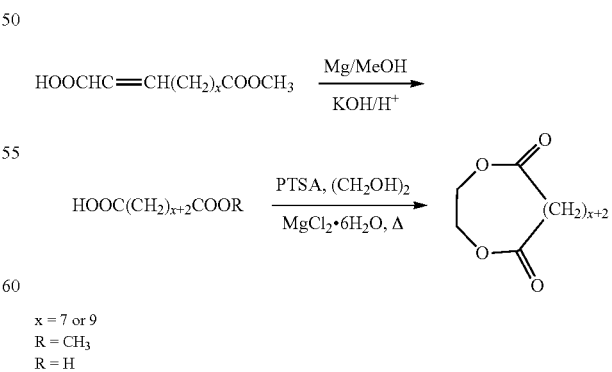

x = 7 or 9
R = CH₃
R = H

In one embodiment, the diene starting material bearing a Z-olefin moiety can be represented by Formula (F):

Formula (F)

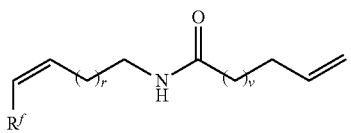

wherein:
R$^f$ is H, methyl, ethyl, or propyl;
r is 1, 2, 3, or 4;
v is 4, 5, 6, or 7.

In one embodiment, the diene starting material bearing a Z-olefin moiety can be represented by Formula (F), wherein R$^f$ is methyl, r is 2 and v is 4 or 6.

In one embodiment, the diene starting material bearing a Z-olefin moiety can be represented by Formula (F), wherein R$^f$ is ethyl, r is 1, 2, 3 or 4 and v is 6 or 7.

In one embodiment, the diene starting material bearing a Z-olefin moiety can be represented by Formula (F), wherein R$^f$ is ethyl, r is 1 or 2 and v is 6.

In one embodiment, the diene starting material bearing a Z-olefin moiety can be represented by Formula (F), wherein R$^f$ is ethyl, r is 1, 2, 3 or 4 and v is 7.

In one embodiment, the diene starting material bearing a Z-olefin moiety can be represented by Formula (F), wherein R$^f$ is ethyl, r is 1 and v is 6.

In one embodiment, the invention provides for a method of synthesizing a musk macrocycle of Formula (B) comprising, performing a ring closing metathesis reaction on a diene of Formula (F) wherein R$^f$ is H, methyl, ethyl, or propyl; r is 1, 2, 3, or 4; v is 4, 5, 6, or 7; in the presence of at least one metathesis catalyst under conditions sufficient to form a metathesis product, wherein the at least one metathesis catalyst is represented by the structure of Formula (5), wherein the catalyst is selected from: C591, C731, C625, C763, C663, C641, C647m, C747, C647, C676, C773, C673, C651 and C831m.

In one embodiment, the invention provides for a method of synthesizing a musk macrocycle of Formula (B) comprising, performing a ring closing metathesis reaction on a diene of Formula (F) wherein R$^f$ is H, methyl, ethyl, or propyl; r is 1, 2, 3, or 4; v is 4, 5, 6, or 7; in the presence of at least one metathesis catalyst under conditions sufficient to form a metathesis product, wherein the at least one metathesis catalyst is represented by the structure of Formula (8), wherein the catalyst is selected from: C885ss, C785ss, C738ss, C869ss, and C725ss.

In one embodiment the invention, provides for a method for synthesizing a musk macrocycle, represented by Formula (K)

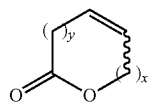

the method comprising:
a) contacting an olefin represented by Formula (G)

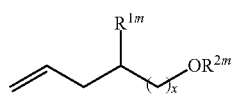

with at least one metathesis reaction partner represented by Formula (H)

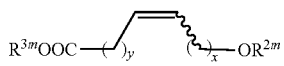

in the presence of at least one olefin metathesis catalyst of Formula (4), Formula (5), Formula (6), or Formula (7), under conditions sufficient to form a metathesis product represented by the structure of Formula (J):

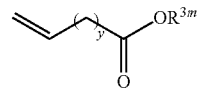

wherein R$^{1m}$ is H or methyl; OR$^{2m}$ is a protected hydroxyl group, which may be selected from an alkyl ether group; an ester group; a silyl ether group; or a carbonate group; R$^{3m}$ is branched or straight C$_1$-C$_5$ alkyl; x is 2, 3, 4 or 5; and y is 5, 6, 7, or 8.

In one embodiment the invention, provides for a method for synthesizing a musk macrocycle, represented by Formula (K)

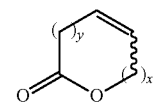

the method comprising:
a) contacting an olefin represented by Formula (G)

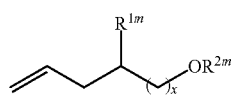

with at least one metathesis reaction partner represented by Formula (H)

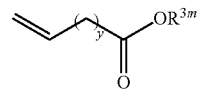

in the presence of at least one olefin metathesis catalyst of Formula (8), Formula (8A), Formula (9), Formula (10), Formula (10A), Formula (11), Formula (12), Formula (12A) or Formula (13) under conditions sufficient to form a metathesis product represented by the structure of Formula (J):

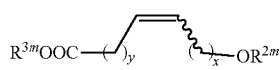

wherein R$^{1m}$ is H or methyl; OR$^{2m}$ is a protected hydroxyl group, which may be selected from an alkyl ether group; an ester group; a silyl ether group; or a carbonate group; R$^{3m}$ is branched or straight C$_1$-C$_5$ alkyl; x is 2, 3, 4 or 5; and y is 5, 6, 7, or 8.

In one embodiment of the invention, one or both of first and second olefins may be olefins with a terminal double bond.

In one embodiment of the invention one of the first or second olefin may be represented by the Formula (G), wherein: $R^{1m}$ is H or methyl; $OR^{2m}$ is a protected hydroxyl group, which may be selected from an alkyl ether group; an ester group; a silyl ether group; or a carbonate group; and x is 2, 3, 4 or 5.

In one embodiment of the invention one of the first or second olefin may be represented by the Formula (H), wherein: $R^{3m}$ is branched or straight $C_1$-$C_5$ alkyl; and y is 5, 6, 7, or 8.

In one embodiment of the invention, the intermediate formed during the cross-metathesis reaction between the first olefin of Formula (G), and the second olefin, of Formula (H), in the presence of at least one ruthenium olefin metathesis catalyst, can be represented by the Formula (J), wherein: $R^{1m}$ is H or methyl; $OR^{2m}$ is a protected hydroxyl group, which may be selected from an alkyl ether group, an ester group, a silyl ether group and a carbonate group; $R^{3m}$ is branched or straight $C_1$-$C_5$ alkyl; x is 2, 3, 4 or 5; $R^{3m}$ is branched or straight $C_1$-$C_5$ alkyl; and y is 5, 6, 7, or 8.

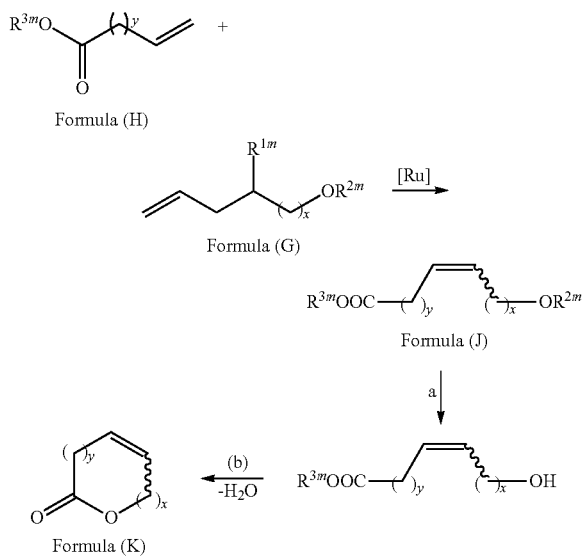

TABLE 10

Musk Macrocycles

| name | y | x |
|---|---|---|
| E/Z ambrettolide | 7 | 6 |
| 7- ambrettolide | 5 | 8 |
| habanolide | 9 | 3 |
| 9-hexadecen-16-olide | 7 | 5 |

The intermediate of Formula (J) can be formed in the presence of any of the ruthenium metathesis catalysts represented by Formula (1), Formula (2), Formula (3), Formula (4), Formula (5), Formula (6), Formula (7), Formula (8), Formula (8A), Formula (9), Formula (10), Formula (10A), Formula (11), Formula (12), Formula (12A) or Formula (13). The ruthenium catalyst can be selected from any of the structures defined, represented or exemplified herein.

Macrocyclic Products

Common macrocyclic musk compounds include ambrettolide (9-ambrettolide and 7-ambrettolide), nirvanolide, habanolide, cosmone, muscenone, velvione, civetone and globanone.

For example, the first and second olefin compounds that can be used to form 7-ambrettolide may be selected from 10-(tert-butoxy)dec-1-ene and methyl oct-7-enoate or dec-9-en-1-yl acetate and methyl oct-7-enoate. The first and second olefin compounds that can be used to form Habanolide may be selected from trimethyl (pent-4-en-1-yloxy) silane and ethyl dodec-11-enoate. The first and second olefin compounds that can be used to form Nirvanolide may be selected from 4-methyl-6-(tert-butoxy)hex-1-ene and methyl 9-decenoate, or 4-methy 1-6-(tert-butoxy)hex-1-ene and ethyl-9-decenoate, or 3-methylhex-5-en-1-yl propionate and methyl 9-decenoate.

As such, the method of the present invention, whereby a hetero-dimer is first formed by metathesis, and then ring-closed by a macrocyclization step, represents a considerably simpler and cheaper process than RCM to form macrocyclic musk compounds, which is industrially scalable in an economic manner.

As described above, a number of the macrocyclic derivatives obtained via the methods of the invention can be used in the fragrance and flavor industry. The macrocyclic derivatives include, for example, the compounds listed in Table (11).

TABLE 11

Macrocyclic Products

| Name | Structure |
|---|---|
| (R)-(+)-Muscopyridine | 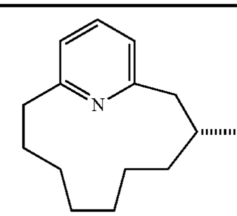 |
| (R)-(−)-Muscone | 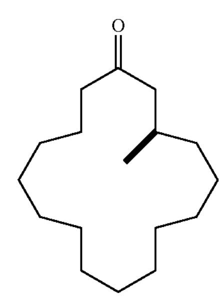 [SMILES: C[C@@H]1CCCCCCCCCCCCCC(=O)C1] |
| (Z)-oxacyclododec-8-en-2-one | 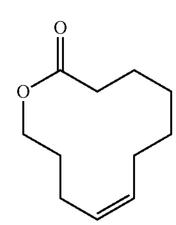 [SMILES: O=C1CCCCC/C=C\CCCO1] |

TABLE 11-continued

| Macrocyclic Products | |
|---|---|
| Name | Structure |
| Ethylene undecanedioate | |
| Civetone | |
| (E/Z)-oxacyclohexadec-11-en-2-one | |
| (Z)-oxacyclotridec-10-en-2-one | |
| (E/Z)-oxacycloheptadec-11-en-2-one | |
| (Z)-oxacyclotetradec-11-en-2-one | |
| 7-Ambrettolide | |
| (Z)-oxacyclotetradec-10-en-2-one | |
| Habanolide | |
| (Z)-oxacyclopentadec-11-en-2-one | |
| Nirvanolide | |
| (Z)-oxacyclohexadec-11-en-2-one | |
| Cyclopentadecanolide (exaltolide) | |
| (Z)-oxacycloheptadec-11-en-2-one | |

TABLE 11-continued

Macrocyclic Products

| Name | Structure |
|---|---|
| Cyclopentadecanone (exaltone) | 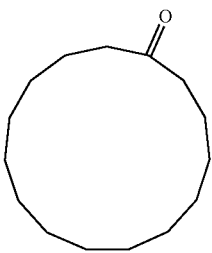 [SMILES: O=C1CCCCCCCCCCCCCC1] |
| (E/Z)-oxacyclotetradec-10-en-2-one | 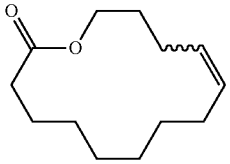 [SMILES: O=C1CCCCCCCC=CCCCO1] |
| Ethylene brassylate | 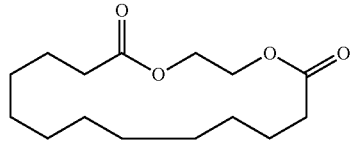 [SMILES: O=C1CCCCCCCCCCCC(=O)OCCO1] |
| (E/Z)-oxacyclopentadec-11-en-2-one | 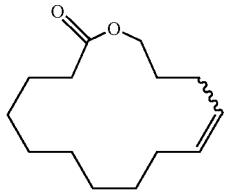 [SMILES: O=C1CCCCCCCCC=CCCCO1] |
| Cyclohexadecanone | 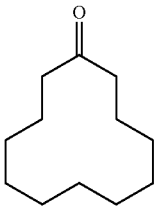 [SMILES: O=C1CCCCCCCCCCC1] |

EXPERIMENTAL

General Information—Materials and Methods

Exemplary embodiments provided in accordance with the presently disclosed subject matter include, but are not limited to, the claims and the following embodiments.

Unless otherwise specified, all manipulations were carried out under air-free conditions in dry glassware in a Vacuum Atmospheres Glovebox filled with $N_2$. General solvents were purified by passing through solvent purification columns. Commercially available substrates were used as received. All solvents and substrates were sparged with Ar before bringing into the glovebox and filtered over neutral alumina (Brockmann I) prior to use. The olefin metathesis catalysts used in the following examples, were synthesized according to the procedures described in International Patent Applications PCT/US2017/046283 and PCT/US2018/027098.

Kinetic NMR experiments were performed on a Varian 600 MHz spectrometer with an AutoX probe. Spectra were analyzed using MestReNova Ver. 8.1.2. $^1$H and $^{13}$C NMR characterization data were obtained on a Bruker 400 with Prodigy broadband cryoprobe and referenced to residual protio-solvent.

All reactions involving metal complexes were conducted in oven-dried glassware under an argon or nitrogen atmosphere using standard Schlenk techniques. Chemicals and solvents were obtained from Sigma-Aldrich, Strem, Alfa Aesar, Nexeo, Brenntag, AG Layne and TCI. Commercially available reagents were used as received unless otherwise noted. Silica gel was purchased from Fisher (0.040-0.063 µm, EMD Millipore).

The following abbreviations are used in the examples:

| | |
|---|---|
| mL | milliliter |
| L | liter |
| ° C. | degrees Celsius |
| $CD_2Cl_2$ | deuterated dichloromethane |
| $CDCl_3$ | deuterated chloroform |
| $C_6D_6$ | deuterated benzene |
| Ar | argon |
| HCl | hydrochloric acid |
| KHMDS | potassium bis(trimethylsilyl)amide |
| r.t. | room temperature |
| THF | tetrahydrofuran |
| $NaHCO_3$ | sodium bicarbonate |
| $Et_2O$ | diethylether |
| HCl | hydrochloric acid |
| $MgSO_4$ | magnesium sulfate |
| DCM | dichloromethane |

Example 1

Synthesis of C738ss

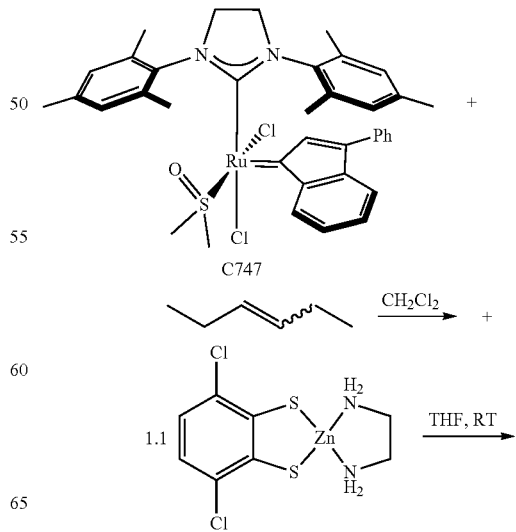

-continued

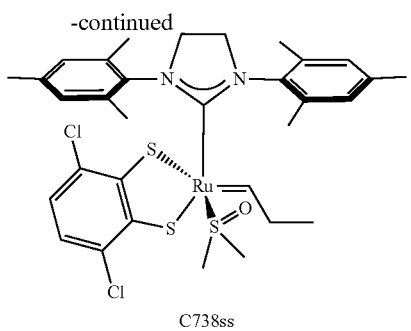

C738ss

To a 20 mL scintillation vial equipped with a magnetic stir bar was added C747 (0.200 g, 0.268 mmol), dichloromethane (5 mL), and 3-hexene (0.066 mL, 0.536 mmol). The reaction was stirred for 30 minutes then (3,6-dichlorobenzene-1,2-dithiolato) (ethylenediamine)zinc(II) (0.099 g, 0.295 mmol) and THF (5 mL) were added and the reaction stirred for an additional 30 minutes before removing all volatiles in vacuo. The resulting residue was extracted with dichloromethane (5 mL), passed through a syringe filter, then slowly combined with diethyl ether (30 mL) to afford a brown microcrystalline solid. The solid was isolated by filtration, washed with diethyl ether (1×10 mL) followed by hexanes (1×10 mL) then dried in vacuo to afford C738ss (0.132 g, 66.9% yield).

$^1$H NMR (400 MHz, CD$_2$Cl$_2$) δ 14.77 (dd, J=7.1, 3.6 Hz, 1H), 7.06 (d, J=8.2 Hz, 1H), 7.05 (br s, 1H), 7.03 (br s, 1H), 6.96 (d, J=8.2 Hz, 1H), 6.92 (br s, 1H), 6.83 (br s, 1H), 4.05-3.90 (m, 6H), 2.85 (s, 3H), 2.76 (s, 3H), 2.58 (s, 3H), 2.53 (s, 3H), 2.28 (br s, 6H), 2.24 (s, 3H), 2.08 (s, 3H), 0.35 (t, J=7.5 Hz, 3H).

Example 2

Synthesis of (Z)-4-Hexen-7-octenoate

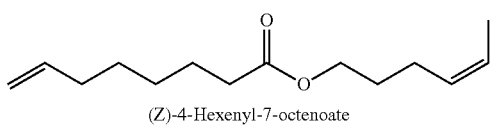 [SMILES: C=CCCCCCC(=O)OCCC/C=C\C]

(Z)-4-Hexenyl-7-octenoate

To a 100 mL round-bottom flask charged with a stir bar were added 50 mL dichloromethane, 7-octenoic acid (1.54 mL, 10.0 mmol) and pyridine (80.7 μL, 1.00 mmol). Oxalyl chloride (1.00 mL, 11.8 mmol) was added dropwise, and the reaction was stirred for overnight. Solvents were then removed in vacuum. 20 mL dichloromethane and pyridine (0.81 mL, 10.0 mmol) were added, and cis-4-hexenol (1.09 mL, 9.3 mmol) was subsequently added dropwise at 0° C. After bringing the reaction to room temperature, it was stirred for an additional 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (1.58 g, 76% yield). The $^1$H NMR and $^{13}$C NMR data correspond to the data found in the literature.

Example 3

Synthesis of (Z)-3-Hexenyl 9-decenoate

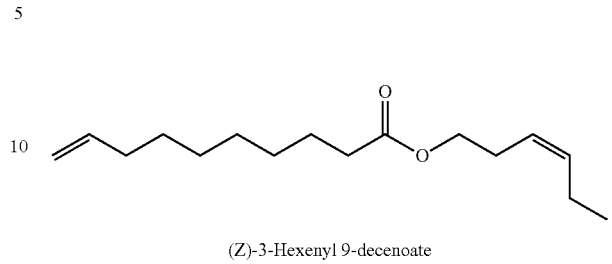

(Z)-3-Hexenyl 9-decenoate

To a 100 mL round-bottom flask charged with a stir bar were added 50 mL dichloromethane, 9-decenoic acid (1.85 mL, 10.0 mmol) and pyridine (80.7 μL, 1.00 mmol). Oxalyl chloride (1.00 mL, 11.8 mmol) was added dropwise, and the reaction was stirred for overnight. Solvents were then removed in vacuum. 20 mL dichloromethane and pyridine (0.81 mL, 10.0 mmol) were added, and cis-3-hexenol (1.10 mL, 9.3 mmol) was subsequently added dropwise at 0° C. After bringing the reaction to room temperature, it was stirred for an additional 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (2.02 g, 86% yield). The $^1$H NMR and $^{13}$C NMR data correspond to the data found in the literature.

Example 4

Synthesis of (Z)-3-Hexenyl 10-undecenoate

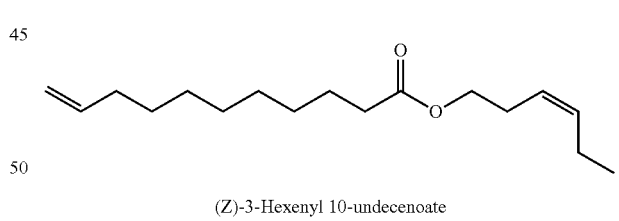

(Z)-3-Hexenyl 10-undecenoate

To a 100 mL round-bottom flask charged with a stir bar were added 20 mL dichloromethane, undecenoyl chloride (2.37 mL, 11.0 mmol), and pyridine (0.89 mL, 11.0 mmol). Cis-3-hexenol (1.18 mL, 10.0 mmol) was then added dropwise at 0° C. The reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (2.53 g, 95% yield). The $^1$H NMR and $^{13}$C NMR data correspond to the data found in the literature.

Example 5

Synthesis of (Z)-4-Hexenyl 9-decenoate

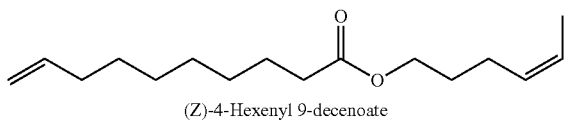 [SMILES: C=CCCCCCCCC(=O)OCCC/C=C\C]

(Z)-4-Hexenyl 9-decenoate

To a 100 mL round-bottom flask charged with a stir bar were added 50 mL dichloromethane, 9-decenoic acid (1.85 mL, 10.0 mmol) and pyridine (80.7 µL, 1.00 mmol). Oxalyl chloride (1.00 mL, 11.8 mmol) was added dropwise, and the reaction was stirred for overnight. Solvents were then removed in vacuum. 20 mL dichloromethane and pyridine (0.81 mL, 10.0 mmol) were added, and cis-4-hexenol (1.09 mL, 9.3 mmol) was subsequently added dropwise at 0° C. After bringing the reaction to room temperature, it was stirred for an additional 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (2.05 g, 87% yield). The $^1$H NMR and $^{13}$C NMR data correspond to the data found in the literature.

Example 6

Synthesis of (Z)-4-Hexenyl 10-undecenoate

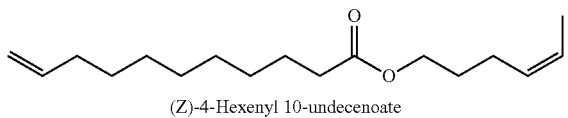 [SMILES: C=CCCCCCCCCC(=O)OCCC/C=C\C]

(Z)-4-Hexenyl 10-undecenoate

To a 100 mL round-bottom flask charged with a stir bar were added 20 mL dichloromethane, undecenoyl chloride (2.37 mL, 11.0 mmol), and pyridine (0.89 mL, 11.0 mmol). Cis-4-hexenol (1.17 mL, 10.0 mmol) was then added dropwise at 0° C. The reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (2.45 g, 92% yield). The $^1$H NMR and $^{13}$C NMR data correspond to the data found in the literature.

Example 7

Synthesis of (Z)-5-Octenyl 10-undecenoate

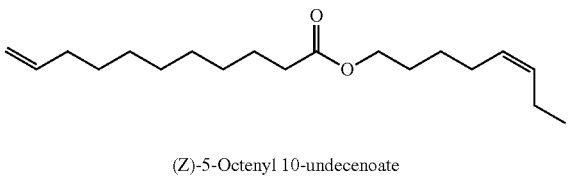 [SMILES: C=CCCCCCCCCC(=O)OCCCC/C=C\CC]

(Z)-5-Octenyl 10-undecenoate

To a 100 mL round-bottom flask charged with a stir bar were added 20 mL dichloromethane, undecenoyl chloride (2.37 mL, 11.0 mmol), and pyridine (0.89 mL, 11.0 mmol). Cis-5-octenol (1.51 mL, 10.0 mmol) was then added dropwise at 0° C.; the reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (2.82 g, 96% yield). The $^1$H NMR and $^{13}$C NMR data correspond to the data found in the literature.

Example 8

Synthesis (Z)-6-Nonenyl 10-undecenoate

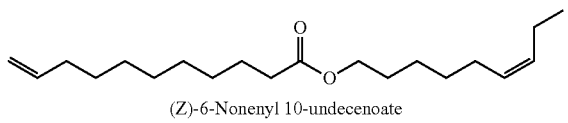 [SMILES: C=CCCCCCCCCC(=O)OCCCCC/C=C\CC]

(Z)-6-Nonenyl 10-undecenoate

To a 100 mL round-bottom flask charged with a stir bar were added 20 mL dichloromethane, undecenoyl chloride (2.37 mL, 11.0 mmol), and pyridine (0.89 mL, 11.0 mmol). Cis-6-nonenol (1.67 mL, 10.0 mmol) was then added dropwise at 0° C. The reaction mixture was brought to room temperature and stirred for 4 h. The reaction mixture was extracted with 1M aq. HCl (200 mL) and sat. aq. NaHCO$_3$ (200 mL). The organic layer was dried over anhydrous MgSO$_4$, filtered, and solvents were removed in vacuum. The product was purified by column chromatography on silica gel (5:95 Et$_2$O:pentane) to yield a colorless oil (2.74 g, 89% yield). The $^1$H NMR and $^{13}$C NMR data correspond to the data found in the literature.

Example 9

Synthesis of (Z)-Oxacyclododec-8-en-2-one

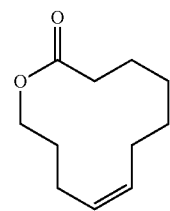

(Z)-Oxacyclododec-8-en-2-one

To a 150 mL Schlenk tube equipped with a stir bar is added (Z)-4-hexenyl-7-octenoate (21.0 mg, 0.0938 mmol) in 30.3 mL DCM and a solution of C785ss (4.4 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel

Example 10

Synthesis of (Z)-Oxacyclotridec-10-en-2-one

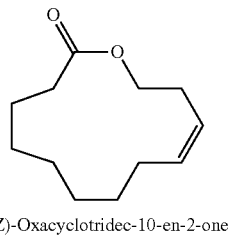

(Z)-Oxacyclotridec-10-en-2-one

To a 150 mL Schlenk tube equipped with a stir bar is added (Z)-3-hexenyl 9-decenoate (23.7 mg, 0.0938 mmol) in 30.3 mL DCM and a solution of C869ss (4.9 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel (1:49 Et$_2$O:pentane) to yield a colorless oil (12.5 mg, 68% yield). The $^1$H NMR and $^{13}$C NMR data correspond to the data found in the literature.

Example 11

Synthesis of (Z)-Oxacyclotetradec-11-en-2-one

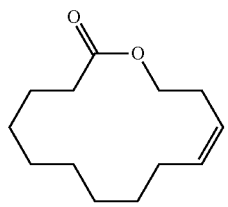

(Z)-Oxacyclotetradec-11-en-2-one

To a 150 mL Schlenk tube equipped with a stir bar is added (Z)-3-hexenyl 10-undecenoate (25.0 mg, 0.0938 mmol) in 30.3 mL DCM and a solution of C725ss (4.1 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel (1:49 Et$_2$O:pentane) to yield a colorless oil (13.2 mg, 67% yield). The $^1$H NMR and $^{13}$C NMR data correspond to the data found in the literature.

Example 12

Synthesis of (Z)-Oxacyclotetradec-10-en-2-one

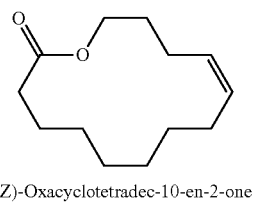

(Z)-Oxacyclotetradec-10-en-2-one

To a 150 mL Schlenk tube equipped with a stir bar is added a solution of (Z)-4-hexenyl 9-decenoate (23.7 mg, 0.0938 mmol) in 30.3 mL DCM and a solution of C738ss (4.2 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel (1:49 Et$_2$O:pentane) to yield a colorless oil (14.2 mg, 72% yield). The $^1$H NMR and $^{13}$C NMR data correspond to the data found in the literature.

Example 13

Synthesis of (Z)-Oxacyclopentadec-11-en-2-one

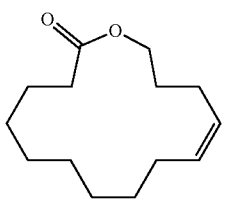

(Z)-Oxacyclopentadec-11-en-2-one

To a 150 mL Schlenk tube equipped with a stir bar is added a solution of (Z)-4-hexenyl 10-undecenoate (25.0 mg, 0.0938 mmol) in 30.3 mL DCM and a solution of C785ss (4.4 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel (1:49 Et$_2$O:pentane) to yield a colorless oil (15.6 mg, 70% yield). The $^1$H NMR and $^{13}$C NMR data correspond to the data found in the literature.

Example 14

Synthesis of (Z)-Oxacyclohexadec-11-en-2-one

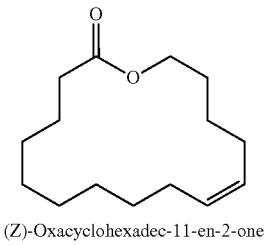 [SMILES: O=C1CCCCCCCC/C=C\CCCCO1]

(Z)-Oxacyclohexadec-11-en-2-one

To a 150 mL Schlenk tube equipped with a stir bar is added a solution of (Z)-5-octenyl 10-undecenoate (27.6 mg, 0.0938 mmol) in 30.3 mL DCM and a solution of C869ss (4.9 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel (1:49 Et$_2$O:pentane) to yield a colorless oil (17.7 mg, 79% yield). The $^1$H NMR and $^{13}$C NMR data correspond to the data found in the literature.

Example 15

Synthesis of (Z)-Oxacycloheptadec-11-en-2-one

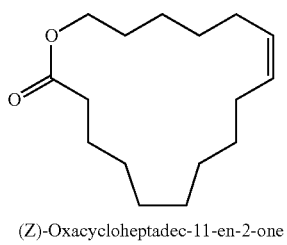 [SMILES: O=C1CCCCCCCC/C=C\CCCCCO1]

(Z)-Oxacycloheptadec-11-en-2-one

To a 150 mL Schlenk tube equipped with a stir bar is added a solution of (Z)-6-nonenyl 10-undecenoate (28.9 mg, 0.0938 mmol) in 30.3 mL DCM and a solution of C725ss (4.1 mg, 0.00563 mmol) in 1 mL DCM. The tube is sealed and taken out of the glovebox. After one freeze, pump, thaw cycle, the reaction flask is heated at 40° C. for 1 h and then quenched with 1 mL butyl vinyl ether. Solvents are removed in vacuum, and the product is purified by column chromatography on silica gel (1:49 Et$_2$O:pentane) to yield a colorless oil (17.8 mg, 75% yield). The $^1$H NMR and $^{13}$C NMR data correspond to the data found in the literature.

For determining selectivity, Z/E mixtures of lactones were synthesized using C647m as references for GC and $^{13}$C NMR studies for comparison. The macrocyclic lactones synthesized herein are obtained in Z/E ratios from 95/5 to 99/1.

Example 16

Synthesis of (E/Z)-Oxacyclotetradec-10-en-2-one

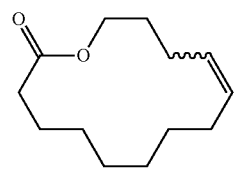

(E/Z)-Oxacyclotradec-10-en-2-one

To a 150 mL Schlenk tube equipped with a stir bar is added a solution of (Z)-4-hexenyl 9-decenoate (23.7 mg, 0.0938 mmol) in 30.3 mL DCM and a solution of C647m (4.6 mg, 0.00563 mmol) in 1 mL DCM. The tube is sealed and taken out of the glovebox. After one freeze, pump, thaw cycle, the reaction flask is heated at 40° C. for 4 h and then quenched with 1 mL butyl vinyl ether. Solvents are removed in vacuum, and the product is purified by column chromatography on silica gel (1:49 Et$_2$O:pentane) to yield a colorless oil (13.0 mg, 67% yield). The $^1$H NMR and $^{13}$C NMR data correspond to the data found in the literature.

Example 17

Synthesis of (E/Z)-Oxacyclopentadec-11-en-2-one

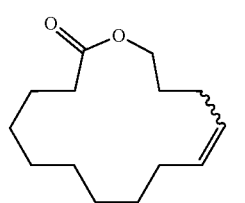

(E/Z)-Oxacyclopentadec-11-en-2-one

To a 150 mL Schlenk tube equipped with a stir bar is added a solution of (Z)-4-hexenyl 10-undecenoate (25.0 mg, 0.0938 mmol) in 30.3 mL DCM and a solution of C647m (3.6 mg, 0.00563 mmol) in 1 mL DCM. The tube is sealed and taken out of the glovebox. After one freeze, pump, thaw cycle, the reaction flask is heated at 40° C. for 4 h and then quenched with 1 mL butyl vinyl ether. Solvents are removed in vacuum, and the product is purified by column chromatography on silica gel (1:49 Et$_2$O:pentane) to yield a colorless oil (11.7 mg, 52% yield). The $^1$H NMR and $^{13}$C NMR data correspond to the data found in the literature.

Example 18

Synthesis of (E/Z)-oxacyclohexadec-11-en-2-one

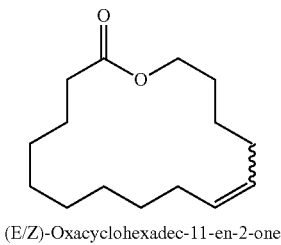 [SMILES: O=C1CCCCCCCCC=CCCCCO1]

(E/Z)-Oxacyclohexadec-11-en-2-one

To a 150 mL Schlenk tube equipped with a stir bar is added a solution of (Z)-5-octenyl 10-undecenoate (27.6 mg, 0.0938 mmol) in 30.3 mL DCM and a solution of C647m (3.6 mg, 0.00563 mmol) in 1 mL DCM. The tube is sealed and taken out of the glovebox. After one freeze, pump, thaw cycle, the reaction flask is heated at 40° C. for 4 h and then quenched with 1 mL butyl vinyl ether. Solvents are removed in vacuum, and the product is purified by column chromatography on silica gel (1:49 Et$_2$O:pentane) to yield a colorless oil (16.8 mg, 75% yield). The $^1$H NMR and $^{13}$C NMR data correspond to the data found in the literature.

Example 19

Synthesis of (E/Z)-Oxacycloheptadec-11-en-2-one

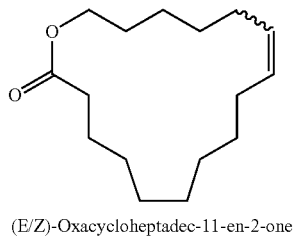 [SMILES: O=C1CCCCCCCCC=CCCCCCO1]

(E/Z)-Oxacycloheptadec-11-en-2-one

To a 150 mL Schlenk tube equipped with a stir bar is added a solution of (Z)-6-nonenyl 10-undecenoate (28.9 mg, 0.0938 mmol) in 30.3 mL DCM and a solution of C647m (3.6 mg, 0.00563 mmol) in 1 mL DCM. The tube is sealed and taken out of the glovebox. After one freeze, pump, thaw cycle, the reaction flask is heated at 40° C. for 4 h and then quenched with 1 mL butyl vinyl ether. Solvents are removed in vacuum, and the product is purified by column chromatography on silica gel (1:49 Et$_2$O:pentane) to yield a colorless oil (16.4 mg. 69% yield). The $^1$H NMR and $^{13}$C NMR data correspond to the data found in the literature.

The invention claimed is:
1. A method for synthesizing a musk macrocycle, represented by Formula (K)

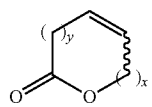

the method comprising:
a) contacting an olefin represented by Formula (G)

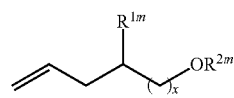

with at least one metathesis reaction partner represented by Formula (H)

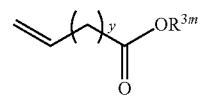

in the presence of at least one Group 8 metal olefin metathesis catalyst under conditions sufficient to form a metathesis product, wherein the at least one metathesis catalyst is represented by the structure of Formula (4):

Formula (4)

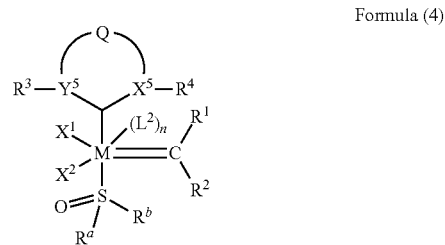

wherein:
$R^{1m}$ is H or methyl;
$OR^{2m}$ is a protected hydroxyl group;
$R^{3m}$ is branched or straight $C_1$-$C_5$ alkyl;
x is 2, 3, 4 or 5;
y is 5, 6, 7, or 8;
M is a Group 8 transition metal;
$L^2$ is a neutral electron donor ligand;
n is 0 or 1;
$R^a$ is hydrogen, unsubstituted hydrocarbyl, substituted hydrocarbyl, unsubstituted heteroatom-containing hydrocarbyl, or substituted heteroatom-containing hydrocarbyl;
$R^b$ is hydrogen, unsubstituted hydrocarbyl, substituted hydrocarbyl, unsubstituted heteroatom-containing hydrocarbyl, or substituted heteroatom-containing hydrocarbyl; or $R^a$ and $R^b$ are linked together to form a five or a six-heterocyclic membered ring with the sulfoxide group;
$X^1$ and $X^2$ are independently anionic ligands;
$R^1$ and $R^2$ are independently hydrogen, unsubstituted hydrocarbyl, substituted hydrocarbyl, unsubstituted heteroatom-containing hydrocarbyl, or substituted heteroatom-containing hydrocarbyl; or $R^1$ and $R^2$ are linked together to form an optionally substituted indenylidene;
$X^5$ and $Y^5$ are independently C, $CR^{3A}$ or N; and only one of $X^5$ or $Y^5$ can be C or $CR^{3A}$;
$R^{3A}$ is hydrogen, unsubstituted hydrocarbyl, unsubstituted heteroatom-containing hydrocarbyl, or substituted heteroatom-containing hydrocarbyl;

Q is a two-atom linkage having the structure or —[CR$^{11}$R$^{12}$]$_s$—[CR$^{13}$R$^{14}$]$_t$— or —[CR$^{11}$=CR$^{13}$]—;

R$^{11}$, R$^{12}$, R$^{13}$ and R$^{14}$ are independently hydrogen, unsubstituted hydrocarbyl, substituted hydrocarbyl, unsubstituted heteroatom-containing hydrocarbyl, or substituted heteroatom-containing hydrocarbyl;

"s" and "t" are independently 1 or 2;

R$^3$ is unsubstituted hydrocarbyl, substituted hydrocarbyl, unsubstituted heteroatom-containing hydrocarbyl, or substituted heteroatom-containing hydrocarbyl; and R$^4$ is unsubstituted hydrocarbyl, substituted hydrocarbyl, unsubstituted heteroatom-containing hydrocarbyl, or substituted heteroatom-containing hydrocarbyl.

2. The method according to claim 1, wherein:

M is Ru;

n is 0;

m is 0;

R$^a$ is unsubstituted C$_1$-C$_{10}$ alkyl, substituted C$_1$-C$_{10}$ alkyl, unsubstituted C$_3$-C$_{10}$ cycloalkyl, substituted C$_3$-C$_{10}$ cycloalkyl, unsubstituted C$_5$-C$_{24}$ aryl or substituted C$_5$-C$_{24}$ aryl;

R$^b$ is unsubstituted C$_1$-C$_{10}$ alkyl, substituted C$_1$-C$_{10}$ alkyl, unsubstituted C$_3$-C$_{10}$ cycloalkyl, substituted C$_3$-C$_{10}$ cycloalkyl, unsubstituted C$_5$-C$_{24}$ aryl or substituted C$_5$-C$_{24}$ aryl; or R$^a$ and R$^b$ are linked together to form a five or a six-heterocyclic membered ring with the sulfoxide group;

X$^1$ and X$^2$ are independently halogen;

R$^1$ is hydrogen;

R$^2$ is unsubstituted phenyl, substituted phenyl, C$_1$-C$_6$ alkyl or substituted 1-propenyl; or R$^1$ and R$^2$ are linked together to form an optionally substituted indenylidene;

X$^5$ and Y$^5$ are independently N;

Q is a two-atom linkage having the structure —[CR$^{11}$R$^{12}$]$_s$—[CR$^{13}$R$^{14}$]$_t$—;

R$^{11}$, R$^{12}$, R$^{13}$ and R$^{14}$ are independently hydrogen;

"s" and "t" are independently 1;

R$^3$ is unsubstituted C$_3$-C$_{10}$ cycloalkyl, substituted C$_3$-C$_{10}$ cycloalkyl, unsubstituted C$_5$-C$_{24}$ aryl, or C$_5$-C$_{24}$ aryl substituted with up to three substituents selected from: unsubstituted C$_1$-C$_{20}$ alkyl, substituted C$_1$-C$_{20}$ alkyl, unsubstituted C$_1$-C$_{20}$ heteroalkyl, substituted C$_1$-C$_{20}$ heteroalkyl, unsubstituted C$_5$-C$_{24}$ aryl, substituted C$_5$-C$_{24}$ aryl, unsubstituted C$_5$-C$_{24}$ heteroaryl, substituted C$_5$-C$_{24}$ heteroaryl, unsubstituted C$_6$-C$_{24}$ aralkyl, substituted C$_6$-C$_{24}$ aralkyl, unsubstituted C$_6$-C$_{24}$ alkaryl, substituted C$_6$-C$_{24}$ alkaryl and halide; and R$^4$ is unsubstituted C$_3$-C$_{10}$ cycloalkyl, substituted C$_3$-C$_{10}$ cycloalkyl, unsubstituted C$_5$-C$_{24}$ aryl, or C$_5$-C$_{24}$ aryl substituted with up to three substituents selected from: unsubstituted C$_1$-C$_{20}$ alkyl, substituted C$_1$-C$_{20}$ alkyl, unsubstituted C$_1$-C$_{20}$ heteroalkyl, substituted C$_1$-C$_{20}$ heteroalkyl, unsubstituted C$_5$-C$_{24}$ aryl, substituted C$_5$-C$_{24}$ aryl, unsubstituted C$_5$-C$_{24}$ heteroaryl, substituted C$_5$-C$_{24}$ heteroaryl, unsubstituted C$_6$-C$_{24}$ aralkyl, substituted C$_6$-C$_{24}$ aralkyl, unsubstituted C$_6$-C$_{24}$ alkaryl, substituted C$_6$-C$_{24}$ alkaryl and halide.

3. The method according to claim 2, wherein the olefin metathesis catalyst is represented by the structure of Formula (5),

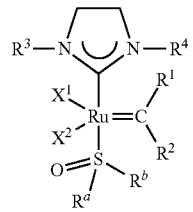

Formula (5)

wherein:

R$^1$ is hydrogen;

R$^2$ is unsubstituted phenyl, substituted phenyl, C$_1$-C$_6$ alkyl or substituted 1-propenyl; or R$^1$ and R$^2$ are linked together to form an optionally substituted indenylidene;

R$^a$ is methyl, ethyl, n-propyl, iso-propyl, n-butyl, tert-butyl, or phenyl;

R$^b$ is methyl, ethyl, n-propyl, iso-propyl, n-butyl, tert-butyl, or phenyl; or R$^a$ and R$^b$ are linked together to form a tetrahydrothiophene oxide with the sulfoxide group;

X$^1$ and X$^2$ are independently Cl, Br, F or I;

R$^3$ is adamantyl, 2,4,6-trimethylphenyl, 2,6-di-iso-propylphenyl, 2-iso-propyl-6-methylphenyl, 2-iso-propyl-phenyl or 2-methyl-phenyl; and R$^4$ is 2,4,6-trimethylphenyl, 2,6-di-iso-propylphenyl, 2-iso-propyl-6-methylphenyl, 2-iso-propyl-phenyl or 2-methyl-phenyl.

4. The method according to claim 3, wherein the olefin metathesis catalyst is selected from:

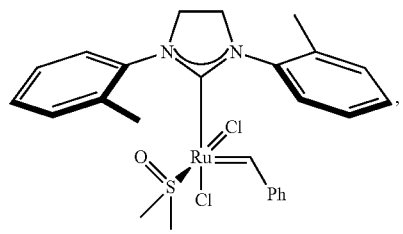

C591

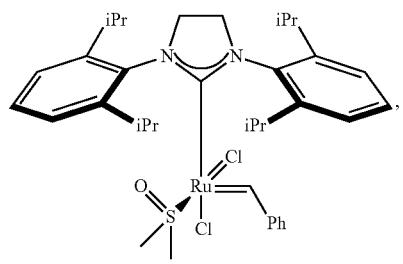

C731

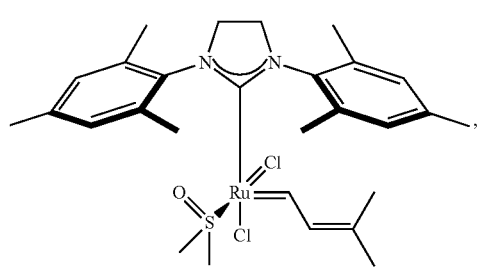

C625

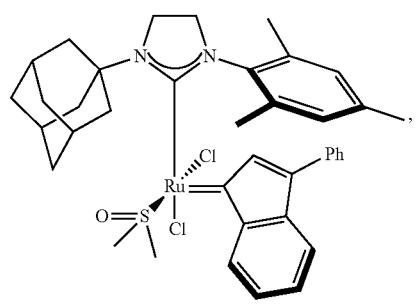
C763
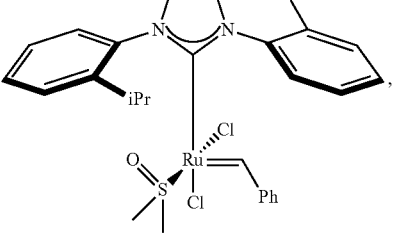
C647
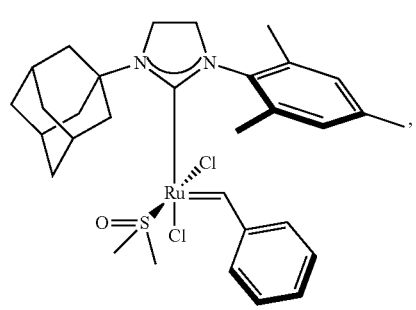
C663
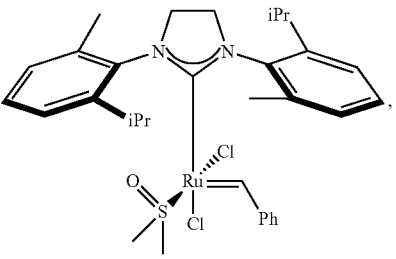
C676
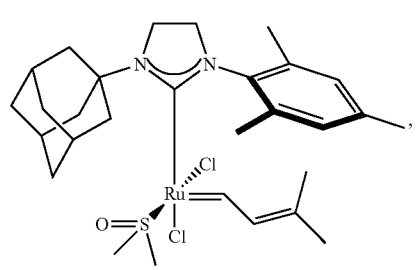
C641
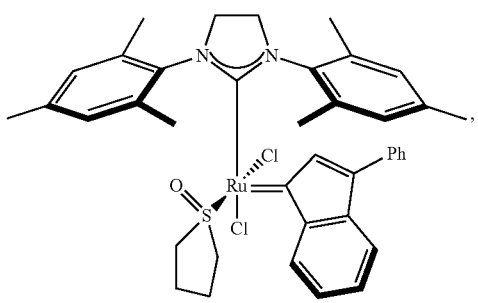
C773
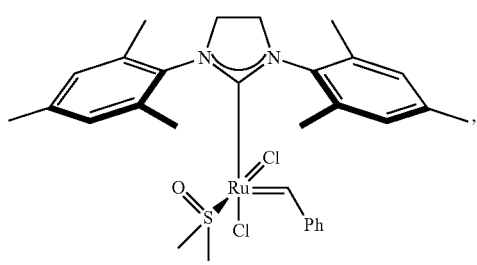
C647$_m$
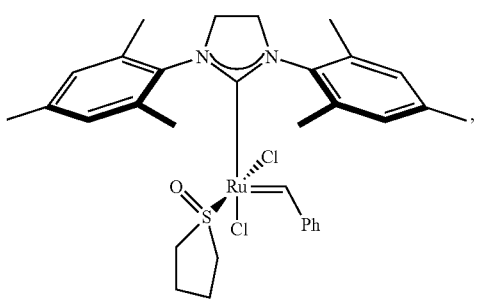
C673
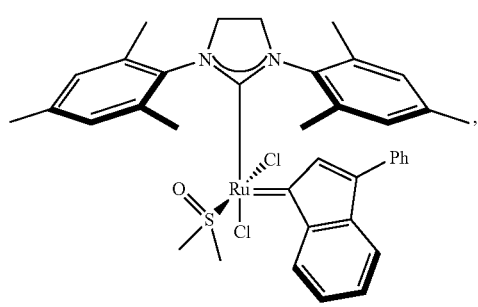
C747
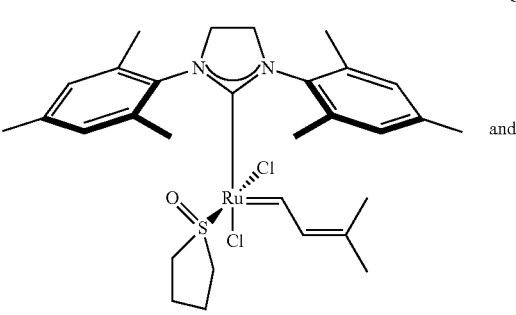
C651
and -continued C831$_m$

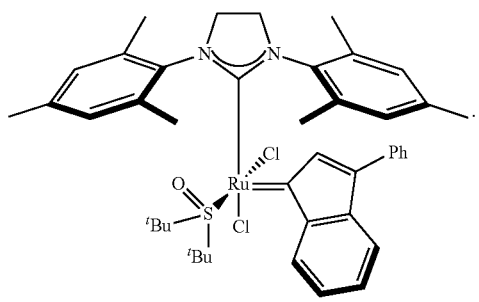

5. The method according to claim 1, wherein:
M is Ru;
n is 0;
m is 0;
$R^a$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl;
$R^b$ is unsubstituted $C_1$-$C_{10}$ alkyl, substituted $C_1$-$C_{10}$ alkyl, unsubstituted $C_3$-$C_{10}$ cycloalkyl, substituted $C_3$-$C_{10}$ cycloalkyl, unsubstituted $C_5$-$C_{24}$ aryl or substituted $C_5$-$C_{24}$ aryl; or $R^a$ and $R^b$ are linked together to form a five or a six-heterocyclic membered ring with the sulfoxide group;
$X^1$ and $X^2$ are independently halogen;

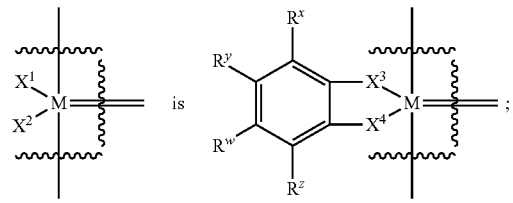

$L^1$ is

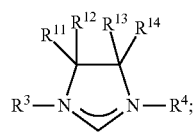

$X^3$ and $X^4$ are independently S or O;
$R^1$ is hydrogen;
$R^2$ is unsubstituted phenyl, substituted phenyl, $C_1$-$C_6$ alkyl or substituted 1-propenyl;
$X^5$ and $Y^5$ are independently N;
Q is a two-atom linkage having the structure —[$CR^{11}R^{12}$]$_s$—[$CR^{13}R^{14}$]$_t$—;
$R^{11}$, $R^{12}$, $R^{13}$ and $R^{14}$ are independently hydrogen;
"s" and "t" are independently 1;
$R^3$ is unsubstituted $C_3$-$C_{10}$ cycloalkyl, substituted $C_3$-$C_{10}$ cycloalkyl, unsubstituted $C_5$-$C_{24}$ aryl, or $C_5$-$C_{24}$ aryl substituted with up to three substituents selected from: unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide; and
$R^4$ is unsubstituted $C_3$-$C_{10}$ cycloalkyl, substituted $C_3$-$C_{10}$ cycloalkyl, unsubstituted $C_5$-$C_{24}$ aryl, or $C_5$-$C_{24}$ aryl substituted with up to three substituents selected from: unsubstituted $C_1$-$C_{20}$ alkyl, substituted $C_1$-$C_{20}$ alkyl, unsubstituted $C_1$-$C_{20}$ heteroalkyl, substituted $C_1$-$C_{20}$ heteroalkyl, unsubstituted $C_5$-$C_{24}$ aryl, substituted $C_5$-$C_{24}$ aryl, unsubstituted $C_5$-$C_{24}$ heteroaryl, substituted $C_5$-$C_{24}$ heteroaryl, unsubstituted $C_6$-$C_{24}$ aralkyl, substituted $C_6$-$C_{24}$ aralkyl, unsubstituted $C_6$-$C_{24}$ alkaryl, substituted $C_6$-$C_{24}$ alkaryl and halide.

6. The method according to claim 5, wherein the olefin metathesis catalyst is represented by the structure of Formula (8), Formula (8)

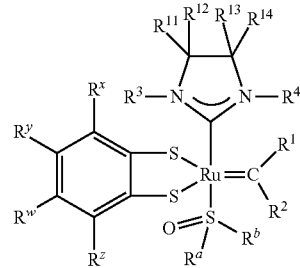

wherein:
$R^a$ is methyl, ethyl, n-propyl, iso-propyl, n-butyl, tert-butyl, cyclohexyl or phenyl;
$R^b$ is methyl, ethyl, n-propyl, iso-propyl, n-butyl, tert-butyl, cyclohexyl or phenyl; or $R^a$ and $R^b$ are linked together to form a five or a six-heterocyclic membered ring with the sulfoxide group;
$R^3$ is adamantyl, 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 2,6-difluorophenyl, 3,5-di-tert-butylphenyl, 2,4-dimethylphenyl or 2-methyl-phenyl;
$R^4$ is 2,4,6-trimethylphenyl, 2,6-di-iso-propylphenyl, 2-methyl-6-tert-butylphenyl, 2-iso-propyl-6-methylphenyl, 2-iso-propyl-phenyl, 2,6-di-ethylphenyl, 2-ethyl-6-methylphenyl, 2,4,6-trifluorophenyl, 2,6-difluorophenyl, 3, 5-di-tert-butylphenyl, 2,4-dimethylphenyl or 2-methyl-phenyl;
$R^1$ is hydrogen and $R^2$ is unsubstituted phenyl, substituted phenyl, $C_1$-$C_6$ alkyl or substituted 1-propenyl; or $R^1$ and $R^2$ are linked together to form an optionally substituted indenylidene;
$R^{11}$ is hydrogen or methyl, $R^{12}$ is hydrogen or methyl, $R^{13}$ is hydrogen and $R^{14}$ is hydrogen;
$R^x$ is methyl, hydrogen or Cl; $R^y$ is hydrogen; $R^w$ is hydrogen; $R^z$ is Cl, t-butyl, hydrogen or phenyl; or $R^x$ and $R^y$ are linked together to form an unsubstituted bicyclic or polycyclic aryl or a substituted bicyclic or polycyclic aryl; or $R^w$ and $R^z$ are linked together to form an unsubstituted bicyclic or polycyclic aryl or a substituted bicyclic or polycyclic aryl; or $R^y$ and $R^w$ are linked together to form an unsubstituted bicyclic or polycyclic aryl or a substituted bicyclic or polycyclic aryl.

7. The method according to claim 6, wherein the olefin metathesis catalyst is selected from:
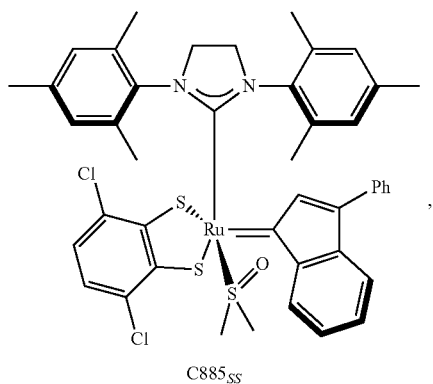
C885$_{SS}$
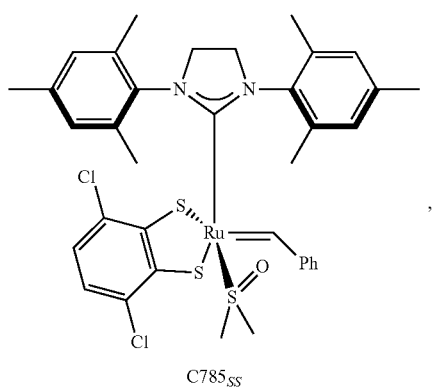
C785$_{SS}$
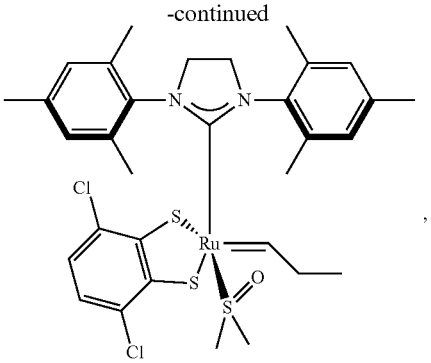
C738$_{SS}$
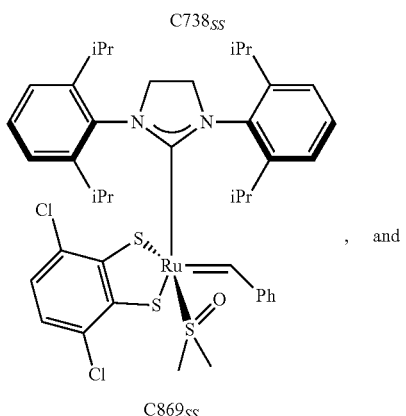
C869$_{SS}$
, and
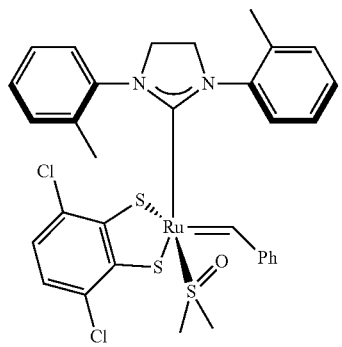
C725$_{SS}$
.
* * * * *